US011951258B2

(12) United States Patent
Guney et al.

(10) Patent No.: US 11,951,258 B2
(45) Date of Patent: Apr. 9, 2024

(54) PATIENT INTERFACE WITH AN OCCIPITAL ANCHOR

(71) Applicant: ResMed Pty Ltd, Bella Vista (AU)

(72) Inventors: Memduh Guney, Sydney (AU); Stewart Joseph Wagner, Hawkesbury (AU); Jeremy McManus, Sydney (AU); Daniel Marc Weiss, Sydney (AU); Michael Kenneth Truscott, Sydney (AU); Nwe Oo Tha, Sydney (AU); Bruce Richard Davies, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/912,815

(22) PCT Filed: Mar. 19, 2021

(86) PCT No.: PCT/AU2021/050253
§ 371 (c)(1),
(2) Date: Sep. 19, 2022

(87) PCT Pub. No.: WO2021/184079
PCT Pub. Date: Sep. 23, 2021

(65) Prior Publication Data
US 2023/0125364 A1 Apr. 27, 2023

(30) Foreign Application Priority Data
Mar. 20, 2020 (AU) ................. 2020900850

(51) Int. Cl.
*A61M 16/06* (2006.01)
*A61M 16/00* (2006.01)
(52) U.S. Cl.
CPC .... *A61M 16/0666* (2013.01); *A61M 16/0066* (2013.01); *A61M 16/0683* (2013.01)

(58) Field of Classification Search
CPC ... A61F 9/027; A61M 11/00; A61M 16/0057; A61M 16/0066; A61M 16/0069;
(Continued)

(56) References Cited

U.S. PATENT DOCUMENTS 4,782,832 A    11/1988   Trimble et al.
4,910,806 A *   3/1990   Baker .................... B63C 11/12
                                                            2/452
(Continued)

FOREIGN PATENT DOCUMENTS

WO   WO 98/004310 A1   2/1998
WO   WO 98/034665 A1   8/1998
(Continued)

OTHER PUBLICATIONS

"Respiratory Physiology", by John B. West, Lippincott Williams & Wilkins, 9th edition published 2012, 8 pages.
(Continued)

*Primary Examiner* — Annette Dixon
(74) *Attorney, Agent, or Firm* — Nixon & Vanderhye P.C.

(57) ABSTRACT

A patient interface includes a plenum chamber pressurisable to a therapeutic pressure, and a seal-forming structure constructed and arranged to seal with a region of a patient's face surrounding an entrance to a patient's airways. The seal-forming structure is constructed and arranged to maintain the therapeutic pressure in the plenum chamber throughout a patient's respiratory cycle in use. The patient interface also includes a positioning and stabilizing structure configured to hold the seal-forming structure in a therapeutically effective position on a patients head. The positioning and stabilizing structure includes a rear strap arranged to contact an occiput of the patient's head. The rear strap is constructed from a first material is arranged to contact a temporal region of the
(Continued)

patient's head, and a second material arranged to contact the occiput of the patients head. The second material is silicone.

15 Claims, 60 Drawing Sheets

(58) Field of Classification Search
CPC .. A61M 16/022; A61M 16/024; A61M 16/06; A61M 16/0611; A61M 16/0616; A61M 16/0622; A61M 16/0633; A61M 16/0666; A61M 16/0683; A61M 16/0694; A61M 16/08; A61M 16/0816; A61M 16/0825; A61M 16/0833; A61M 16/0875; A61M 16/1045; A61M 16/105; A61M 16/107; A61M 16/109; A61M 16/125; A61M 16/16; A61M 16/20; A61M 2016/0015; A61M 2016/0027; A61M 2016/003; A61M 2016/0036; A61M 2202/0085; A61M 2202/0208; A61M 2202/0225; A61M 2202/30; A61M 2205/02; A61M 2205/0238; A61M 2205/0266; A61M 2205/273; A61M 2205/3365; A61M 2205/3368; A61M 2205/3569; A61M 2205/3592; A61M 2205/42; A61M 2205/50; A61M 2205/583; A61M 2205/588; A61M 2205/59; A61M 2205/6054; A61M 2205/8206; A61M 2205/84; A61M 2209/06; A61M 2209/082; A61M 2209/088; A61M 2210/0618; A61M 2210/0625; A61M 2230/432; A61M 2250/00; A61M 39/08; A62B 18/025; A62B 18/084; A63B 33/002; B63C 11/12; B63C 11/205; B63C 2011/128; G02C 3/003; Y10S 2/909
See application file for complete search history.

(56) References Cited

U.S. PATENT DOCUMENTS

| | | | |
|---|---|---|---|
| 4,944,310 A | | 7/1990 | Sullivan |
| 5,046,200 A | * | 9/1991 | Feder ................ A63B 33/002 |
| | | | 2/452 |
| 5,464,010 A | * | 11/1995 | Byram ................ A62B 18/084 |
| | | | 128/206.17 |
| 5,687,715 A | | 11/1997 | Landis |
| 6,532,959 B1 | | 3/2003 | Berthon-Jones |
| 6,581,594 B1 | | 6/2003 | Drew et al. |
| 7,866,944 B2 | | 1/2011 | Kenyon et al. |
| 8,297,285 B2 | * | 10/2012 | Henry ............... A61M 16/0616 |
| | | | 128/207.18 |
| 8,636,479 B2 | | 1/2014 | Kenyon et al. |
| 8,638,014 B2 | | 1/2014 | Sears et al. |
| 8,733,349 B2 | | 5/2014 | Bath et al. |
| 11,338,103 B2 | * | 5/2022 | Blanch .............. A61M 16/0666 |
| 2006/0081250 A1 | | 4/2006 | Bordewick et al. |
| 2009/0044808 A1 | | 2/2009 | Guney Memduh et al. |
| 2009/0050156 A1 | | 2/2009 | Ng et al. |
| 2009/0173349 A1 | | 7/2009 | Hernandez et al. |
| 2010/0000534 A1 | | 1/2010 | Kooij et al. |
| 2013/0008449 A1 | * | 1/2013 | Busch ............... A61M 16/0683 |
| | | | 128/206.21 |
| 2014/0283843 A1 | * | 9/2014 | Eves ................. A61M 16/0616 |
| | | | 128/206.24 |
| 2015/0182719 A1 | * | 7/2015 | Grashow ........... A61M 16/0683 |
| | | | 128/205.25 |
| 2019/0125996 A1 | * | 5/2019 | Bentley ............ A61M 16/0816 |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | 2017/185140 A1 | 11/2017 |
| WO | 2020/000033 A1 | 1/2020 |
| WO | 2020/037360 A1 | 2/2020 |

OTHER PUBLICATIONS

International Search Report dated Jul. 8, 2021 in International Application No. PCT/AU2021/050253, 7 pages.
Written Opinion of the International Searching Authority dated Jul. 8, 2021 in International Application No. PCT/AU2021/050253, 10 pages.
International Preliminary Report on Patentability dated Mar. 9, 2022 issued in International Application No. PCT/AU2021/050253 (5 pages).
Extended European Search Report dated Oct. 17, 2023 issued in European Application No. 21772521.7 (5 pages).

* cited by examiner

Copyright 2012 ResMed Limited

Copyright 2012 ResMed Limited

| | |
|---|---|
| SP | Saggital Plane |
| PRO | Pronasale |
| COL | Columella |
| SUB | Subnasale |
| NA | Naris |
| MAN | Major Axis of Naris |
| UV | Upper Vermillion |
| LI | Lip Inferior |
| NLS | Naso labial Sulcus |

Copyright 2012 ResMed Limited

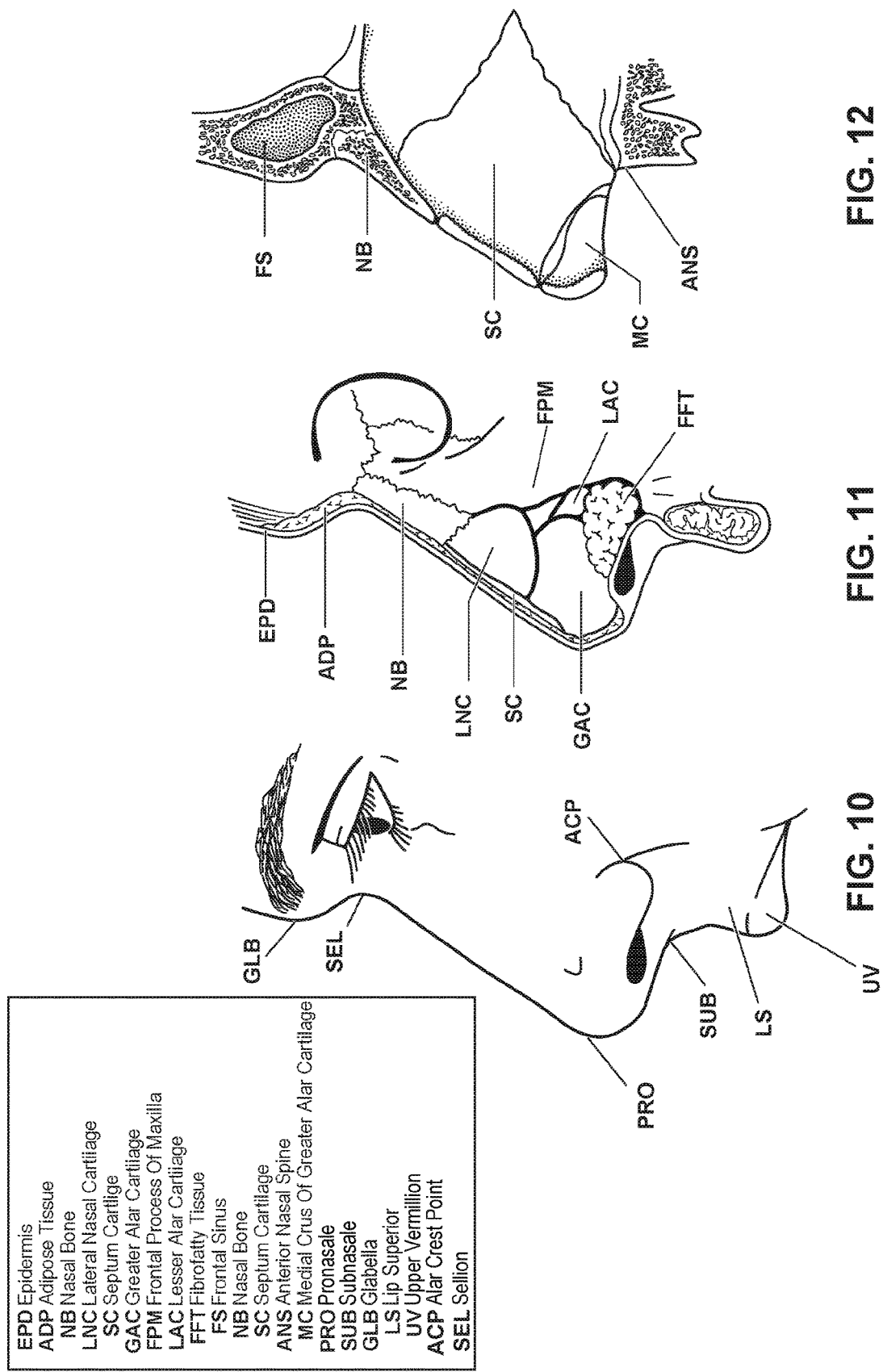

FB Frontal Bone
SOF Supraorbital Foramen
NB Nasal Bones
SC Septal Cartilage
LNC Lateral Nasal Cartilage
SES Sesamoid Cartilage
GAC Greater Alar Cartilage
MC Medial Crus Of Greater Alar Cartilage
ANS Anterior Nasal Spine
IOF Infraorbital Foramen
LSC Lesser Nasal Cartilage
AFT Alar Fibrofatty Tissue Copyright 2012 ResMed Limited

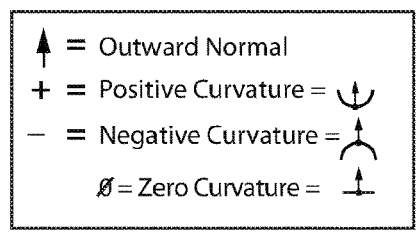
↑ = Outward Normal
+ = Positive Curvature = ⌣
− = Negative Curvature = ⌢
∅ = Zero Curvature = ⊥

| CUR | Curve |
| SRF | Surface |
| INS | Interior Surface |
| OD | Outside Diameter |
| ID | Inside Diameter |

Copyright 2015 ResMed Limited

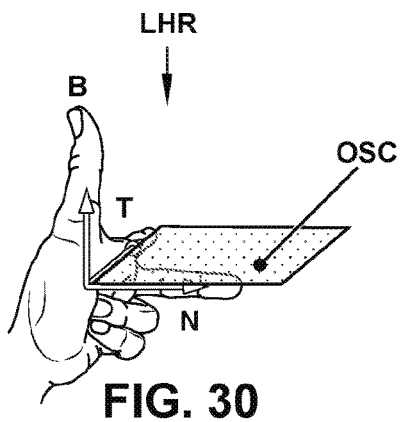
FIG. 30
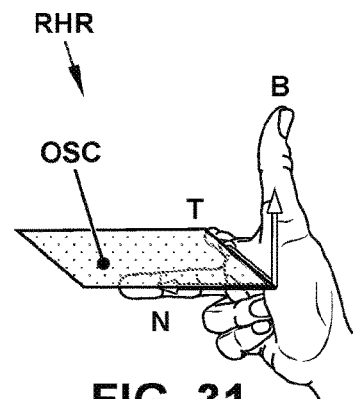
FIG. 31
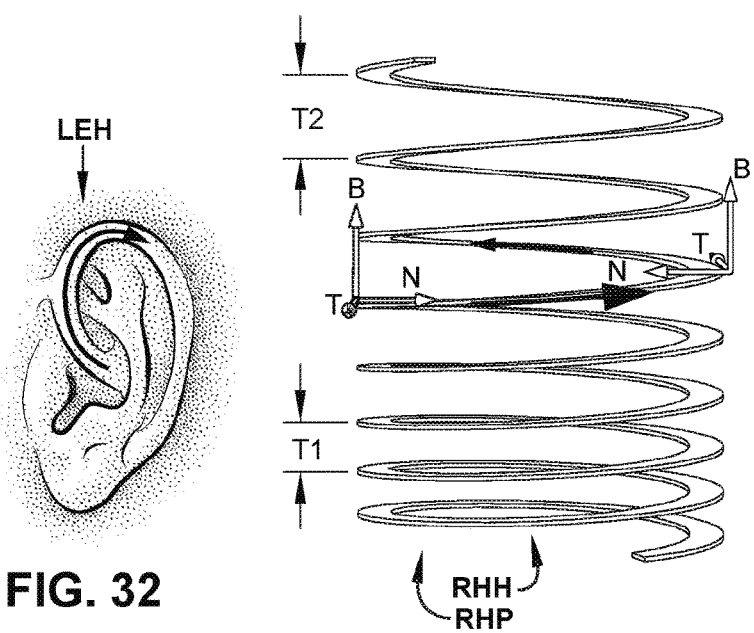
FIG. 32     FIG. 34     FIG. 33
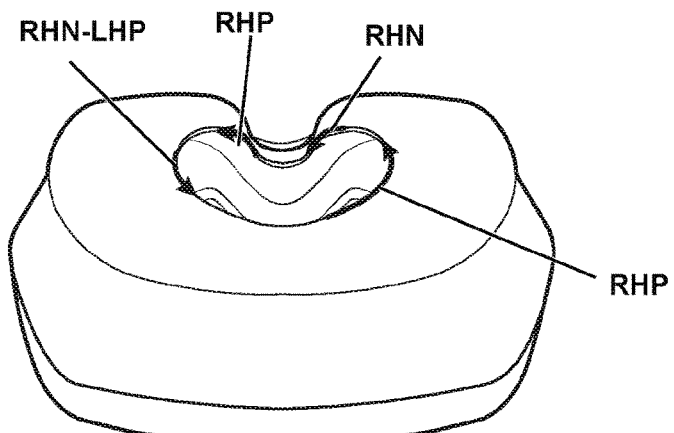
| | |
|---|---|
| LHR | Left-hand Rule |
| RHR | Right-hand Rule |
| B | Binormal |
| OSC | Osculating Plane |
| T | Tangent |
| N | Normal |
| LEH | Left Ear Helix |
| REH | Right Ear Helix |
| RHH | Right-hand Helix |
| RHP | Right-hand Positive |
| RHN | Right-hand Negative |
| RHN-LHP | Right-hand Negative (=left-hand Positive) |
FIG. 35
Copyright 2015 ResMed Limited

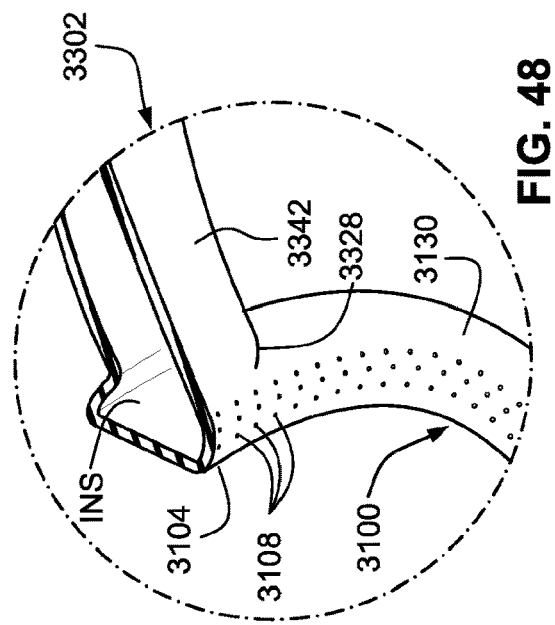
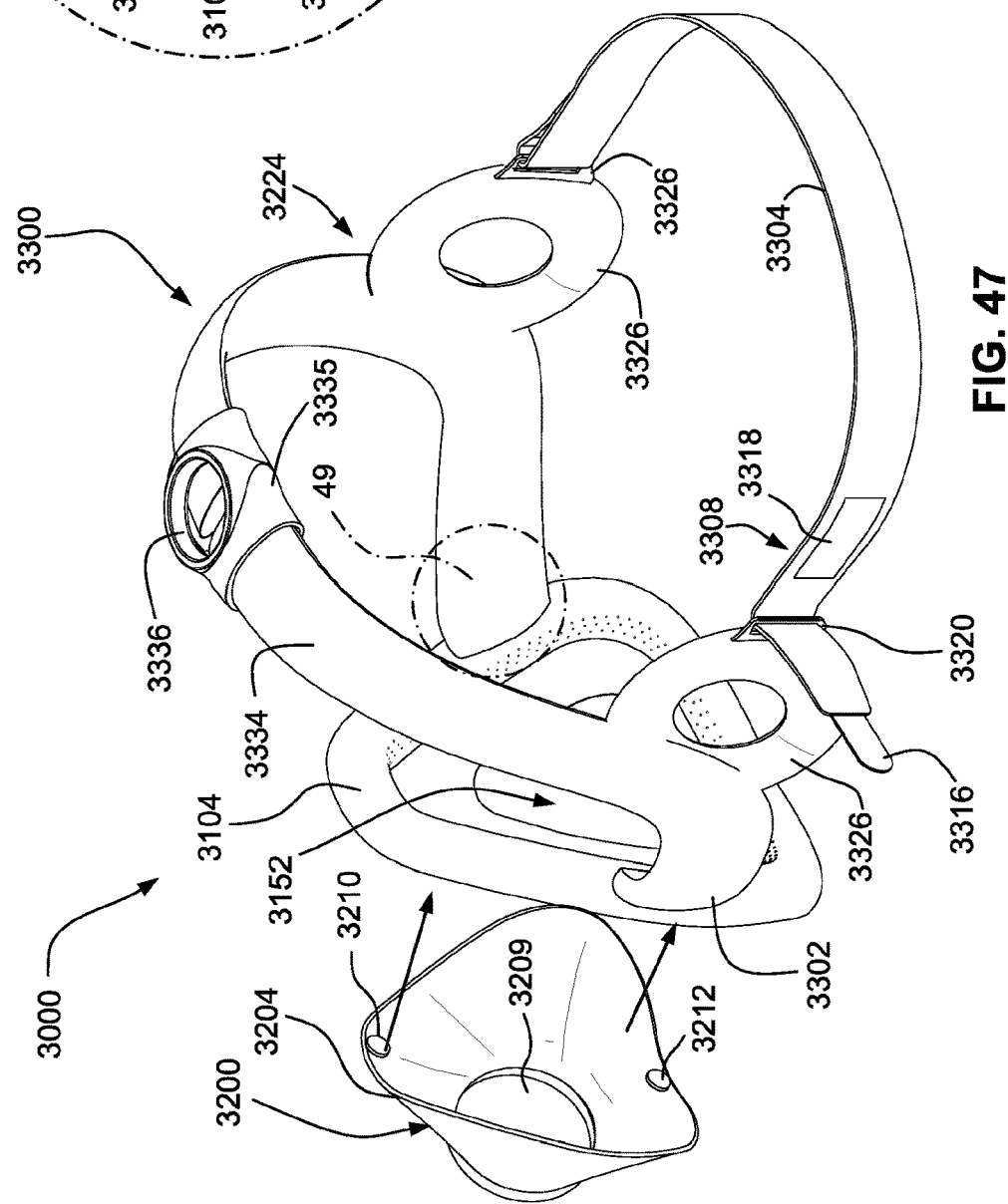

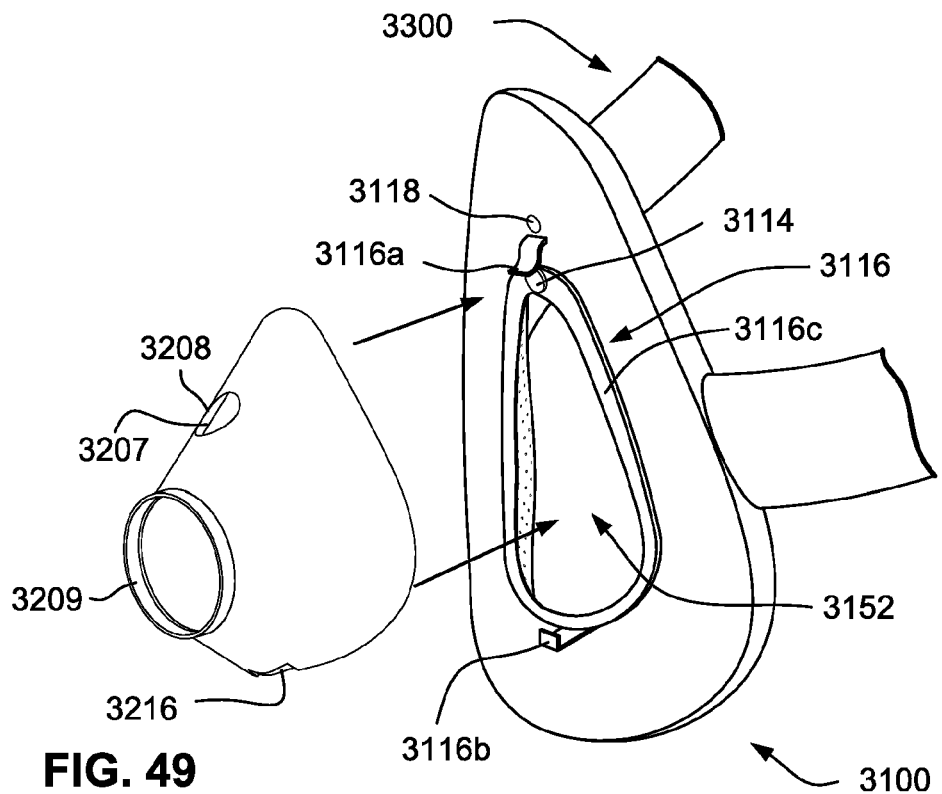
FIG. 49
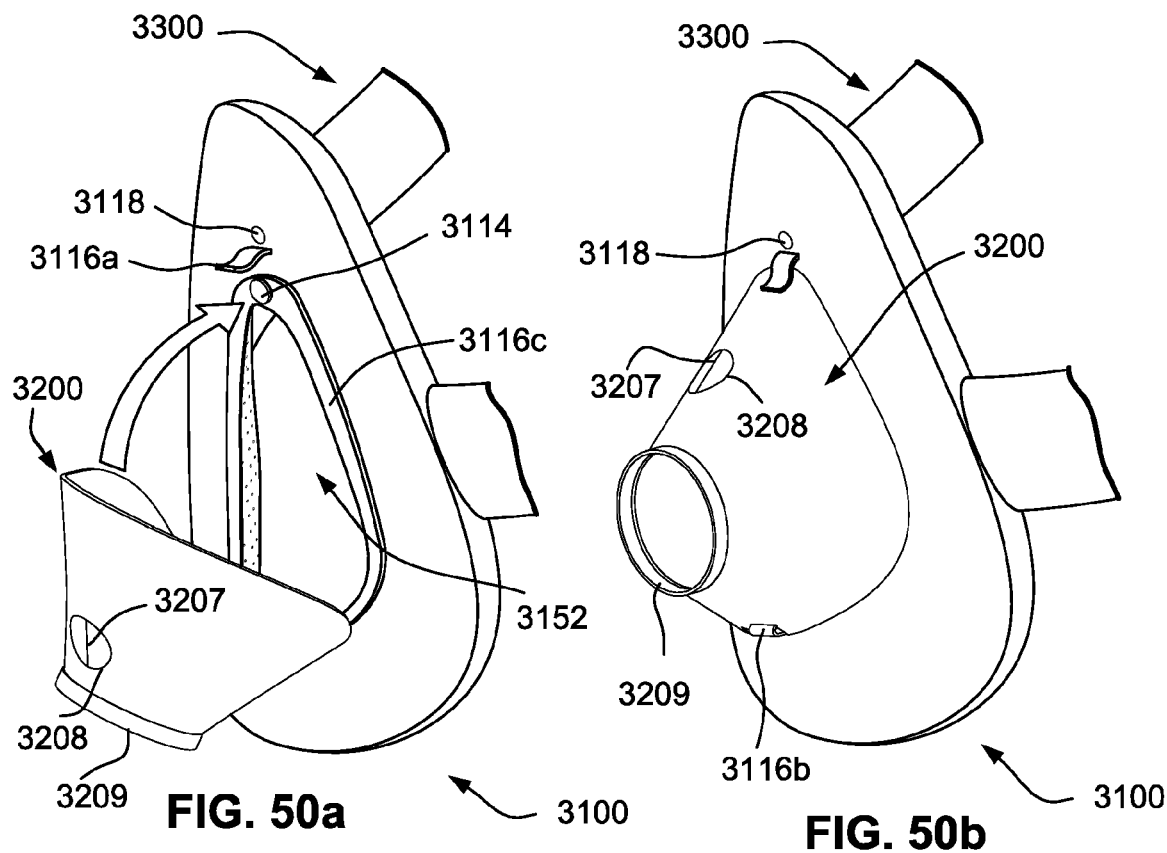
FIG. 50a  FIG. 50b

PATIENT INTERFACE WITH AN OCCIPITAL ANCHOR

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATION

This application is the U.S. national phase of International Application No. PCT/AU2021/050253 filed Mar. 19, 2021 which designated the U.S. and claims priority to Australian Provisional Application No. 2020900850 filed Mar. 20, 2020, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nares and the mouth are the entrances to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g., apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See Sullivan, U.S. Pat. No. 4,944,310.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise at least one of: a Respiratory Pressure Therapy (RPT) device, an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient.

Depending upon the therapy to be applied, the patient interface may seal, e.g., with a region of the patient's face, to facilitate the delivery of gas at a pressure at sufficient variance with ambient pressure to effect therapy, e.g., at a positive pressure of about 10 $cmH_2O$ relative to ambient pressure.

For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid complete sealing. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology, e.g., if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g., for sleeping while lying on one's side in bed with the head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable, especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g., filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable or difficult to use, a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g., aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to, for example, overlay an upper lip region and a nasal bridge region of a face. In one form of patient interface, a seal-forming structure may comprise an element that surrounds a mouth region in use, e.g., by forming a seal on a lower lip region of the face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g., because of the different shape, structure, variability and sensitivity of different regions of the patient's face. For example, a structure of swimming goggles that overlays a patient's forehead to seal therewith may not be appropriate to use on a patient's nose.

Certain seal-forming structures may be designed for mass manufacture such that one design can fit and be comfortable and effective for a wide range of different face shapes and sizes. To the extent to which there is a mismatch between the shape of the patient's face, and the seal-forming structure of the mass-manufactured patient interface, one or both must adapt in order for the seal-forming structure seal with the patient's face.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force may be required to position the patient interface against the face in order to seal therewith or leak may occur. Additional force may cause discomfort for the patient during use.

Another type of seal-forming structure incorporates a flap of relatively thin material positioned about the periphery of the mask so as to provide a self-sealing action against the face of the patient when positive pressure is applied within the mask. Like the type of seal-forming structure described in the preceding paragraph, if the size and shape of the seal-forming structure does not accurately correspond to the size and shape of the patient's face, additional force may be required to seal against the patient's face, or the mask may leak. Additional force may cause discomfort for the patient during use. Furthermore, if the size and shape of the seal-forming structure does not accurately correspond to that of the patient, then the seal-forming structure may crease or buckle in use due its relative thinness, which may result in leaking.

Another type of seal-forming structure may comprise a friction-fit element, e.g., for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited, Kwok et al., International Publication No. WO 1998/004310 A1; Davidson et al., International Publication No. WO 2006/074513 A1; Dravitzki et al., International Publication No. WO 2010/135785 A1.

One form of nasal pillow is found in the ADAM Circuit manufactured by Puritan-Bennett Corporation. Another nasal pillow, or nasal puff is the subject of Trimble et al., U.S. Pat. No. 4,782,832, assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: Gunaratnam et al., International Publication No. WO 2004/073778 A1 (describing amongst other things aspects of the ResMed Limited SWIFT™ nasal pillows); Guney et al., U.S. Publication No. 2009/0044808 A1 (describing amongst other things aspects of the ResMed Limited SWIFT™ LT nasal pillows); Davidson et al., International Publication No. WO 2005/063328 A1 and Lubke et al., International Publication No. WO 2006/130903 A1 (describing amongst other things aspects of the ResMed Limited MIRAGE LIBERTY™ full-face mask); Rummery et al., International Publication No. WO 2009/052560 A1 (describing amongst other things aspects of the ResMed Limited SWIFT™ FX nasal pillows).

2.2.3.1.2 Positioning and Stabilizing

A seal-forming structure of a patient interface used for positive air pressure therapy is subject to the corresponding force of the air pressure to disrupt a seal. Thus, a variety of techniques have been used to position the seal-forming structure, and to maintain it in sealing relation with the appropriate portion of the face.

One technique is the use of adhesives. See, for example, Kooij et al., U.S. Publication No. 2010/0000534 A1. However, the use of adhesives may be uncomfortable for some.

Another technique is the use of one or more straps and/or stabilizing harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus, RPT devices may also act as flow therapy devices. Examples of RPT devices include a CPAP device and a ventilator.

Air pressure generators are known in a range of applications, e.g., industrial-scale ventilation systems. However, air pressure generators for medical applications have particular requirements not fulfilled by more generalised air pressure generators, such as the reliability, size, and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is minimization of acoustic noise because the patient may be sleeping during operation.

| Table of noise output levels of prior RPT devices (one specimen only, measured using test method specified in ISO 3744 in CPAP mode at 10 cmH$_2$O). | | |
|---|---|---|
| RPT Device name | A-weighted sound pressure level dB(A) | Year (approx.) |
| C-Series TANGO ™ | 31.9 | 2007 |
| C-Series TANGO ™ with Humidifier | 33.1 | 2007 |
| S8 ESCAPE ™ II | 30.5 | 2005 |
| S8 ESCAPE ™ II with H4i ™ Humidifier | 31.1 | 2005 |
| S9 AUTOSET ™ | 26.5 | 2010 |
| S9 AUTOSET ™ with H5i ™ Humidifier | 28.6 | 2010 |

One known RPT device used for treating sleep disordered breathing is the S9™ Sleep Therapy System, manufactured by ResMed Limited. Another example of an RPT device is a ventilator. Ventilators such as the ResMed STELLAR™ Series of Adult and Paediatric Ventilators may provide support for invasive and non-invasive non-dependent ventilation for a range of patients for treating a number of conditions such as but not limited to NMD, OHS and COPD.

The ELISÉE™ 150 ventilator and VS III™ ventilator, manufactured by ResMed Limited, may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, warm air applied generally to the face area in and about the patient interface in cooler climates is more comfortable than cold air. Humidifiers therefore often have the capacity to heat the flow of air was well as humidifying it. Moreover, warmer air has a greater capacity for water vapor.

A range of artificial humidification devices and systems are known, however, they may not fulfil the specialised requirements of a medical humidifier.

Medical humidifiers are used to increase humidity and/or temperature of the flow of air in relation to ambient air when required, typically where the patient may be asleep or resting (e.g., at a hospital). A medical humidifier for bedside placement may be small. A medical humidifier may be configured to only humidify and/or heat the flow of air delivered to the patient without humidifying and/or heating the patient's surroundings. Room-based systems (e.g., a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, and some are difficult or inconvenient to use by patients.

2.2.3.5 Data Management

There may be clinical reasons to obtain data to determine whether the patient prescribed with respiratory therapy has been "compliant", e.g., that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Vent Technologies

Some forms of treatment systems may include a vent to allow the washout of exhaled carbon dioxide. The vent may allow a flow of gas from an interior space of a patient interface, e.g., from within the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g., through noise or focused airflow.

ResMed Limited has developed a number of improved mask vent technologies. See Kwok, International Publication No. WO 1998/034665 A1; Gunaratnam et al., International Publication No. WO 2000/078381 A1; Drew et al., U.S. Pat. No. 6,581,594 B1; Ng et al., U.S. Publication No. 2009/0050156 A1; Guney et al., U.S. Publication No. 2009/0044808 A1.

| Table of noise of prior masks (ISO 17510-2: 2007, 10 cmH$_2$O pressure at 1 m) | | | | |
|---|---|---|---|---|
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |
| RESMED ™ MIRAGE ™ (*) | nasal | 29.5 | 21.5 | 1998 |
| RESMED ™ ULTRA MIRAGE ™ | nasal | 36 (3) | 28 (3) | 2000 |
| RESMED ™ MIRAGE ACTIVA ™ | nasal | 32 (3) | 24 (3) | 2002 |
| RESMED ™ MIRAGE MICRO ™ | nasal | 30 (3) | 22 (3) | 2008 |
| RESMED ™ MIRAGE ™ SoftGel | nasal | 29 (3) | 22 (3) | 2008 |
| RESMED ™ MIRAGE ™ FX | nasal | 26 (3) | 18 (3) | 2010 |
| RESMED ™ MIRAGE SWIFT ™ (*) | nasal pillows | 37 | 29 | 2004 |
| RESMED ™ MIRAGE SWIFT ™ II | nasal pillows | 28 (3) | 20 (3) | 2005 |
| RESMED ™ MIRAGE SWIFT ™ LT | nasal pillows | 25 (3) | 17 (3) | 2008 |
| RESMED ™ AIRFIT ™ P10 | nasal pillows | 21 (3) | 13 (3) | 2014 |

((*) one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.7 Heat and Moisture Exchanger (HMX) Technology

A patient may be susceptible to drying of the internal airways passages while undergoing various forms of respiratory therapy as described above. For example, CPAP therapy entails providing the patient with a flow of air pressurized at a pressure greater than ambient continuously, and this continuous flow of air, particularly at an elevated level in conjunction with the positive air pressure, may causing drying of the patient's airways. That drying may cause discomfort, which in turn may negatively impact the patient's compliance with therapy.

To minimize the drying effect of these forms of respiratory therapy, the flow of air provided to the patient may be humidified before it reaches the patient. Certain forms of humidification technology, such as those described above, actively provide humidified air to the patient to reduce the drying effect by heating a reservoir of water and passing air over its surface to increase the absolute humidity of the air, i.e., the air absorbs water vapour from the reservoir. The humidified air is then passed to the patient via the air circuit. The air circuit may also be heated to prevent condensation, also known as rainout, of the water vapour within the air circuit during transport to the patient. These forms of technology typically involve filling the reservoir with water before therapy, and then the reservoir is provided to the RPT system so that the water can be heated to humidify the air for therapy. The reservoir typically requires regular cleaning, there is a risk of spillage, which may be particularly problematic in the context of electrical components, and the reservoir requires refilling by the patient before use.

Eliminating the need for a pre-supplied water source, such as a water-filled reservoir, and input electrical power to heat the water may provide several benefits. For example, the RPT device could be made smaller because it would not require space for the water reservoir and heating plate. Since no electrical energy is consumed in heating of the water, electricity costs may be reduced. Also, fewer electrical components may be needed in the RPT device, which reduces its cost and complexity. Also, the RPT device may be easier to use because there is no water reservoir to fill, empty, and clean. Risk of spillage may be reduced as well. Also, operation of the RPT device may be simplified because there are no humidification settings to operate.

In operation, the patient breathes out (exhalation) air that has been heated within the patient's body and that has absorbed water vapour from the patient's airways. The heat and moisture in the exhaled air is captured by the HMX material(s), i.e., the HMX material(s) are heated by the relatively warm exhaled air and the HMX material(s) adsorb water vapour from the relatively humid exhaled air, as the exhaled air passes through HMX material(s) prior to being vented to atmosphere. During inhalation, the flow of pressurized air passes through the HMX material(s) in the opposite direction to exhalation to reach the patient's airways, and the source of the incoming air is typically ambient air. Thus, the flow of pressurized air, as it passes through the HMX material(s) prior to reaching the patient's airways, absorbs moisture in the form of water vapour as it is desorbed from the HMX material(s) and the flow of pressurized air is heated by heat released from the HMX material(s).

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology is directed to a patient interface that may comprise: a plenum chamber; a seal-forming structure; and a positioning and stabilizing structure. The patient interface may further comprise a vent structure. The patient interface may further be configured to leave the patient's mouth uncovered, or if the seal-forming structure is configured to seal around the patient's nose and mouth, the patient interface may be further configured to allow the patient to breath from ambient in the absence of a flow of pressurised air through the plenum chamber inlet port.

Another aspect of the present technology is directed to a patient interface comprising: a plenum chamber pressurisable to a therapeutic pressure of at least 4 $cmH_2O$ above ambient air pressure, said plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilizing structure configured to hold the seal-forming structure in a therapeutically effective position on the patient's head, the positioning and stabilizing structure comprising a tie, the tie being constructed and arranged so that at least a portion overlies a region of the patient's head superior to an otobasion superior of the patient's head in use; and a vent structure configured to allow a continuous flow of gases exhaled by the patient from an interior of the plenum chamber to ambient, said vent structure being sized and shaped to maintain the therapeutic pressure in the plenum chamber in use; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air through the plenum chamber inlet port.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Another aspect of the present technology is a patient interface comprising: a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a top strap constructed and arranged to contact, in use, at least a region of the patient's head superior to an otobasion superior of the patient's head, a side strap coupled to the top strap, the side strap constructed and arranged, in use, to extend in an anterior and inferior direction toward the seal-forming structure, and a rear strap coupled to the top strap and the side strap, the rear strap being arranged to extend in a posterior and inferior direction on the patient's head in order to contact, in use, an occiput of the patient's head, the rear strap constructed from a first material and a second material, the first material arranged to contact, in use, a temporal region of the patient's head, and the second material arranged to contact, in use, the occiput of the patient's head, wherein the second material is not textile (e.g., silicone), and wherein the second material is configured to limit motion of the top strap and/or the side strap in an anterior and/or posterior direction while in the therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

In certain forms, the second material does not extend across the parietal bone.

In certain forms, the rear strap does not extend across the parietal bone from a left side of the patient's head to a right side of the patient's head.

In certain forms, the positioning and stabilizing structure does not extend across the Sternocleidomastoid muscle of the patient.

In certain forms, the second material has a greater coefficient of friction than the first material.

In certain forms, the first material and the second material is connected at a transition, the first material does not cross the transition and overlap the second material, and the second material does not cross the transition and overlap the first material.

In certain forms, the first material and the second material are connected along the transition using sewing, adhesive, sonic welding, magnets, and/or mechanical fasteners.

In certain forms, the top strap and the side strap are formed as a continuous structure and are not connected using a fastener.

In certain forms, the second material is included only on the occiput and nowhere else along the patient's head.

In certain forms, at least one of the plenum chamber and the seal-forming structure are constructed at least partially from the first material.

In certain forms, the first material is a textile.

In certain forms, the first material is an elastic, and is configured, in use, to increase in length as a result of a tensile force.

In certain forms, the second material does not contact the temporal region below an otobasion inferior of the patient's head.

In certain forms, the positioning and stabilizing structure includes a pad constructed from the second material, the pad configured to grip the occiput in order to provide an anchor point for the gas delivery tube.

In certain forms, the pad includes an adjustment mechanism configured to change a usable length of the pad, the usable length configured to contact the patient's head in use.

In certain forms, the adjustment mechanism is Velcro, a ladder lock buckle, and/or a snap.

In certain forms, the first material and the second material of the rear strap are permanently affixed to one another.

In certain forms, the positioning and stabilizing structure further includes a tab coupled between the top strap and the side strap, the rear strap being removably coupled to the tab.

In certain forms, the first material of the rear strap extends from the tab to the second material.

In certain forms, the positioning and stabilizing structure further comprises an extender directly coupled to the tab, the rear strap being directly coupled to the extender.

In certain forms, the extender is removably coupled to the tab.

In certain forms, the rear strap is permanently coupled to the extender.

In certain forms, the rear strap is removably coupled to the extender.

In certain forms, the extender is constructed from the second material.

In certain forms, the extender is constructed from silicone and/or hytrel.

In certain forms, the top strap and the side strap together define a gas delivery tube formed as a continuous structure to receive the flow of air from a connection port on top of the patient's head and to deliver the flow of air to the entrance of the patient's airways via the seal-forming structure.

In certain forms, the second material is silicone.

Another aspect of the present technology is a positioning and stabilizing structure configured to hold a seal-forming structure in a therapeutically effective position on a patient's head, the seal-forming structure being constructed and arranged to form a seal with a region of a patient's face surrounding an entrance to a patient's airways for sealed delivery of a flow of air at a therapeutic pressure of at least 4 cmH$_2$O with respect to ambient air pressure throughout a patient's respiratory cycle in use, the positioning and stabilizing structure comprising: a gas delivery tube configured to deliver the flow of air to the entrance of a patient's airways via the seal-forming structure, the gas delivery tube being constructed and arranged to contact, in use, the patient's head, the gas delivery tube including, a first seal end configured to connect to the seal-forming structure, a second seal end spaced apart from the first seal end, and configured to connect to the seal-forming structure, and a mid-portion disposed between the first seal end and the second seal end, the mid-portion including a port for receiving the flow of air, the mid-portion configured to contact, in use, a superior region of the patient's head; an eyelet coupled to the gas delivery tube between the first seal end and the mid-portion; and a rear strap coupled to the eyelet and configured, in use, to pass around a posterior portion of the patient's head, the rear strap including a pad configured to grip an occiput of the patient's head; wherein the rear strap includes a side portion constructed from a first material and the pad constructed from a second material different than the first material.

In certain forms, a second eyelet is coupled to the gas delivery tube between the second seal end and the mid-portion, the rear strap extending between the eyelet and the second eyelet.

In certain forms, the first material is a textile.

In certain forms, the first material is stretchable, and is configured, in use, to increase in length as a result of a tensile force.

In certain forms, wherein the rear strap is removably coupled to the eyelet.

In certain forms, an extender is coupled directly to the eyelet.

In certain forms, the extender is removably coupled to the eyelet.

In certain forms, the extender is permanently affixed to the eyelet.

In certain forms, the rear strap is removably coupled to the extender.

In certain forms, the extender is constructed from the second material.

In certain forms, the first material extends between the extender and the pad.

In certain forms, the pad is constructed from silicone.

In certain forms, the pad and the side portion are permanently coupled together.

Another aspect of the present technology is a positioning and stabilizing structure configured to hold a seal-forming structure in a therapeutically effective position on a patient's head, the seal-forming structure being constructed and arranged to form a seal with a region of a patient's face surrounding an entrance to a patient's airways for sealed delivery of a flow of air at a therapeutic pressure of at least 4 cmH$_2$O with respect to ambient air pressure throughout a patient's respiratory cycle in use, the positioning and stabilizing structure comprising: a top strap being constructed and arranged to contact, in use, the patient's head, the top strap including, a first seal end configured to connect to the seal-forming structure, a second seal end spaced apart from the first seal end, and configured to connect to the seal-forming structure, and a mid-portion disposed between the first seal end and the second seal end, the mid-portion configured to contact, in use, a superior region of the patient's head; a first eyelet coupled to the top strap between the first seal end and the mid-portion; a second eyelet coupled to the top strap between the second seal end and the mid-portion; and a rear strap coupled to the first eyelet and to the second eyelet, the rear strap configured, in use, to pass around a posterior portion of the patient's head, the rear strap includes, a first side portion coupled to the first eyelet, a second side portion coupled to the second eyelet, and a pad permanently coupled to the first side portion and to the second side portion, the pad configured to grip an occiput of the patient's head; wherein the first side portion and the second side portion are constructed from a first material and the pad constructed from a second material, the first material being a textile and the second material not being a textile.

In certain forms, the top strap is a gas delivery tube configured to deliver the flow of air to the entrance of a patient's airways via the seal-forming structure.

In certain forms, the first material is stretchable, and is configured, in use, to increase in length as a result of a tensile force.

In certain forms, the second material is rigid or semi-rigid, and is configured to maintain its shape under a tensile load.

In certain forms, the first side portion is removably coupled to the first eyelet and the second side portion is removably coupled to the second eyelet.

In certain forms, a first extender is coupled directly to the first eyelet and positioned between the first eyelet and the first side portion, the first extender being constructed from a third material; and a second extender coupled directly to the second eyelet and positioned between the second eyelet and the second side portion, the second extender being constructed from the third material; wherein the third material is not a textile.

In certain forms, the third material is rigid or semi-rigid, and is configured to maintain its shape under a tensile load.

In certain forms, the first extender is permanently coupled to the first side portion and the second extender is permanently coupled to the second side portion.

In certain forms, the first extender is removably coupled to the first eyelet and the second extender is removably coupled to the second eyelet.

In certain forms, the third material is identical to the second material.

In certain forms, the pad includes an adjustment mechanism configured to change a usable length of the pad, the usable length configured to contact the patient's head in use.

In certain forms, the adjustment mechanism is Velcro, a ladder lock buckle, a magnet, and/or a snap.

In certain forms, the second material is silicone.

Another aspect of the present technology is a positioning and stabilizing structure to provide a force to hold a seal-forming structure in a therapeutically effective position on a patient's head, the positioning and stabilizing structure comprising: a top strap constructed and arranged to contact, in use, at least a region of the patient's head superior to an otobasion superior of the patient's head, a side strap coupled to the top strap, the side strap constructed and arranged, in use, to extend in an anterior and inferior direction toward the seal-forming structure, and a rear strap coupled to the top strap and the side strap, the rear strap being arranged to contact, in use, a posterior region of the patient's head, the rear strap constructed from a first material and a second material.

Another aspect of the present technology is a patient interface comprising a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a top strap constructed and arranged to contact, in use, at least a region of the patient's head superior to an otobasion superior of the patient's head, the top strap constructed and arranged, in use, to extend in an anterior and inferior direction toward the seal-forming structure; a removable arm removably coupled to the top strap, the removable arm constructed and arranged, in use, to extend in an posterior and inferior direction, the removable arm comprising: a first end including a clip configured to removable engage the top strap, and a second end opposite to the first end; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

Another aspect of the present technology is a removable arm removably coupled to a top strap, the removable arm constructed and arranged, in use, to extend in an posterior and inferior direction, the removable arm comprising: a first end including a clip configured to removable engage the top strap, and a second end opposite to the first end.

Another aspect of the present technology is a patient interface comprising a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a gas delivery tube formed as a continuous structure to receive the flow of air from a connection port on top of the patient's head and to deliver the flow of air to the entrance of the patient's airways via the seal-forming structure, the gas delivery tube including a tab constructed and arranged to contact, in use, at least a region of the patient's head superior to an otobasion superior of the patient's head; a removable arm removably coupled to the tab, the removable arm constructed and arranged, in use, to extend in an posterior and inferior direction, the removable arm comprising: a first end including a clip configured to removable engage the top strap, and a second end opposite to the first end; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

In certain forms, the second end of each removable arm of the pair of removable arms comprises a slot.

In certain forms, the slots are arcuate.

In certain forms, a rear strap is connected to the second end of each removable arm of the pair of removable arms.

In certain forms, the rear strap is configured to be arranged to extend in a posterior and inferior direction on the patient's head in order to contact, in use, an occiput of the patient's head.

In certain forms, the rear strap is constructed from a first material and a second material.

In certain forms, the first material is arranged to contact, in use, a temporal region of the patient's head, and the second material arranged to contact, in use, the occiput of the patient's head.

In certain forms, the first material is textile and wherein the second material is silicone.

In certain forms, the rear strap is received within each slot.

In certain forms, a width of the rear strap is less than a width of the slot, the rear strap configured to move within the slot and adjust a force vector.

In certain forms, each tab includes an opening having an opening length between approximately 30 mm and approximately 50 mm.

In certain forms, the clip includes a clip length that is less than the opening length.

In certain forms, the clip is configured to move along the clip length in order to adjust a force vector.

In certain forms, the clip is configured to pivot within the opening in order to adjust a force vector.

In certain forms, each removable arm curves between the first end and the second end.

In certain forms, the second end is configured to contact the patient's head approximately 30° below the Frankfort horizontal.

In certain forms, each clip is biased toward a closed position.

In certain forms, the clip is movable to an opening position in order to connect to the respective tab.

In certain forms, the first end of each removable arm further includes a post.

In certain forms, the clip pivotably connected to the post.

In certain forms, the clip is freely rotatable about the post.

In certain forms, the clip is biased toward a surface of the removable arm.

In certain forms, the first end of each removable arm further includes a lock configured to limit rotation of the clip.

In certain forms, the lock of each removable arm is removably connected to the respective post.

In certain forms, the lock of each removable arm is integrally formed with the respective post.

In certain forms, the lock is overmolded with the post.

In certain forms, the lock of each removable arm includes a protrusion configured to selectively contact the clip and limit the clip's rotational movement.

In certain forms, each removable arm is curved between the first end and the second end.

In certain forms, each removable arm tapers toward the second end.

In certain forms, the patient interface includes a pair of textile sleeves.

In certain forms, each textile sleeve of the pair of textile sleeves is configured to receive a removable arm of the pair of removable arms.

Another aspect of the present technology is a removable arm removably coupled to a tab, the removable arm constructed and arranged, in use, to extend in an posterior and inferior direction, the removable arm comprising: a first end including a clip configured to removable engage the top strap, and a second end opposite to the first end.

Another aspect of the present technology is a patient interface comprising: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a gas delivery tube formed as a continuous structure to receive the flow of air from a connection port on top of the patient's head and to deliver the flow of air to the entrance of the patient's airways via the seal-forming structure, the gas delivery tube including a pair of tabs constructed and arranged to contact, in use, at least a region of the patient's head superior to an otobasion superior of the patient's head, wherein each tab of the pair of tabs having an opening with an opening length; a pair of removable arms removably coupled to the tabs, each removable arm constructed and arranged, in use, to extend in an posterior and inferior direction, each removable arm comprising: a first end including a clip configured to removable one tab of the pair of tabs, wherein the clip includes a clip length that is less than the opening length, wherein the clip is configured to move along the clip length and/or pivot within the opening in order to adjust a force vector, and a second end opposite to the first end; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

In certain forms, the second end of each removable arm of the pair of removable arms comprises a slot.

In certain forms, the slots are arcuate.

In certain forms, a rear strap is connected to the second end of each removable arm of the pair of removable arms.

In certain forms, the rear strap is configured to be arranged to extend in a posterior and inferior direction on the patient's head in order to contact, in use, an occiput of the patient's head, the rear strap constructed from a first material and a second material, the first material arranged to contact, in use, a temporal region of the patient's head, and the second material arranged to contact, in use, the occiput of the patient's head.

In certain forms, the first material is textile and wherein the second material is silicone.

In certain forms, the rear strap is received within each slot.

In certain forms, a width of the rear strap is less than a width of the slot, the rear strap configured to move within the slot and adjust a force vector.

In certain forms, the opening length of each tab of the pair of tabs is between approximately 30 mm and approximately 50 mm.

In certain forms, each removable arm curves between the first end and the second end.

In certain forms, the second end is configured to contact the patient's head approximately 30° below the Frankfort horizontal.

In certain forms, each clip is biased toward a closed position, and wherein the clip is movable to an opening position in order to connect to the respective tab.

In certain forms, each arm of the pair of arms includes at least one bendable section configured to allow positional adjustment between the first end and the second end In certain forms, the at least one bendable section is a plurality of bendable sections, wherein each bendable section of the plurality of bendable sections is independently adjustable.

Another aspect of the present technology is a patient interface comprising: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a gas delivery tube formed as a continuous structure to receive the flow of air from a connection port on top of the patient's head and to deliver the flow of air to the entrance of the patient's airways via the seal-forming structure, the gas delivery tube including a pair of tabs constructed and arranged to contact, in use, at least a region of the patient's head superior to an otobasion superior of the patient's head; a pair of removable arms removably coupled to the tabs, each removable arm constructed and arranged, in use, to extend in an posterior and inferior direction, each removable arm comprising: a first end including a post, a clip movable about the post and configured to removable engage the top strap, and a lock configured to selectively limit movement of the clip about the post, and a second end opposite to the first end; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

In certain forms, the clip is pivotably connected to the post.

In certain forms, the clip is freely pivotable about the post when the lock is in an unlocked position.

In certain forms, the clip is biased toward a surface of the removable arm.

In certain forms, the lock of each removable arm is removably connected to the respective post.

In certain forms, the lock of each removable arm is integrally formed with the respective post.

In certain forms, the lock is overmolded with the post.

In certain forms, the lock of each removable arm includes a protrusion configured to selectively contact the clip and limit rotational movement of the clip.

In certain forms, each removable arm is curved between the first end and the second end.

In certain forms, each removable arm tapers toward the second end.

In certain forms, a pair of textile sleeves, wherein each textile sleeve of the pair of textile sleeves is configured to receive a removable arm of the pair of removable arms.

In certain forms, a strap is not connected to the pair of removable arms.

Another aspect of the present technology is a patient interface comprising a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a gas delivery tube formed as a continuous structure to receive the flow of air from a connection port on top of the patient's head and to deliver the flow of air to the entrance of the patient's airways via the seal-forming structure, the gas delivery tube including a pair of tabs constructed and arranged to contact, in use, at least a region of the patient's head superior to an otobasion superior of the patient's head; a pair of removable arms removably coupled to the tab, the removable arm constructed and arranged, in use, to extend in an posterior and inferior direction, each removable arm comprising: a first end including a clip configured to removable engage the top strap, a second end opposite to the first end, the second end including a slot, and a rear strap extending between the pair of removable arms, the rear strap being connected to each removable arm through the slot; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

Another aspect of the present technology is a pair of removable arms removably coupled to the tab, the removable arm constructed and arranged, in use, to extend in an posterior and inferior direction, each removable arm comprising: a first end including a clip configured to removable engage the top strap, a second end opposite to the first end, the second end including a slot, and a rear strap extending between the pair of removable arms, the rear strap being connected to each removable arm through the slot.

Another aspect of the present technology is a patient interface comprising a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a gas delivery tube formed as a continuous structure to receive the flow of air from a connection port on top of the patient's head and to deliver the flow of air to the entrance of the patient's airways via the seal-forming structure, the gas delivery tube including a pair of tabs constructed and arranged to contact, in use, at least a region of the patient's head superior to an otobasion superior of the patient's head; a pair of removable arms removably coupled to the tab, the removable arm constructed and arranged, in use, to extend in an posterior and inferior direction, each removable arm comprising: a first end including a clip configured to removable engage the top strap, a second end opposite to the first end, the second end, and a lock connected to the first end for selectively limiting the movement of the clip, the lock configured to bias the clip toward a locked position; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

Another aspect of the present technology is a pair of removable arms removably coupled to the tab, the removable arm constructed and arranged, in use, to extend in an posterior and inferior direction, each removable arm comprising: a first end including a clip configured to removable engage the top strap, a second end opposite to the first end, the second end, and a lock connected to the first end for selectively limiting the movement of the clip, the lock configured to bias the clip toward a locked position.

Another example of the present technology is a patient interface comprising: a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a rear strap constructed from a first material; a pair of upper straps connected to the rear strap, the pair of upper straps constructed from a second material; a pair of lower straps connected to the pair of upper straps, the pair of upper straps constructed from a third material; a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

Another example of the present technology is a positioning and stabilizing structure comprising: a rear strap constructed from a first material; a pair of upper straps connected to the rear strap, the pair of upper straps constructed from a second material; a pair of lower straps connected to the pair of upper straps, the pair of upper straps constructed from a third material.

Another example of the present technology is a patient interface comprising: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a rear strap configured to contact the patient's head and overlay at least a portion of the occipital bone; a pair of upper straps configured to selectively apply a posterior directed tensile force, the pair of upper straps connected to the rear strap inferior to at least a portion of the rear strap; a pair of lower straps configured to selectively apply a posterior directed tensile force, the pair of lower straps connected to the pair of upper straps inferior to at least a portion of the upper straps; a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

In certain forms, the rear strap is constructed from a first material, the pair of upper straps are constructed from a second material, and the pair of lower straps are constructed from a third material.

In certain forms, the first material and the third material are the same.

In certain forms, the first material and the third material are stretchable materials.

In certain forms, the rear strap is pre-tensioned in a non-use position.

In certain forms, the first material and the second material are the same.

In certain forms, the first material and the second material are inextensible materials.

In certain forms, the rear strap is substantially triangular in shape.

In certain forms, a superior side of the rear strap is substantially horizontal.

In certain forms, an inferior end of the rear strap forms a rear strap angle between approximately 110° and approximately 150°, and specifically the rear strap angle is approximately 130°.

In certain forms, the pair of upper straps form a substantially V-shape.

In certain forms, an inferior end of the pair of upper straps forms an upper strap angle between approximately 110° and approximately 170°, and specifically the upper strap angle is approximately 150°.

In certain forms, the pair of lower straps form a substantially V-shape.

In certain forms, the pair of upper straps and the pair of lower straps together for a substantially X-shape.

In certain forms, a lower strap angle is formed between one lower strap of the pair of lower straps and an adjacent upper strap of the pair of upper straps, wherein the lower strap angle is between approximately 30° and approximately 70°, specifically the lower strap angle is approximately 50°.

In certain forms, the pair of upper straps are pre-tensioned in a non-use position.

In certain forms, the pair of lower straps are removably connected to the plenum chamber.

In certain forms, the positioning and stabilizing structure further includes a gas delivery tube formed as a continuous structure to receive the flow of air from a connection port on top of the patient's head and to deliver the flow of air to the entrance of the patient's airways via the seal-forming structure, the gas delivery tube including a pair of tabs constructed and arranged to contact, in use, at least a region of the patient's head superior to an otobasion superior of the patient's head.

In certain forms, each upper strap of the pair of upper straps is removably connected to a tab of the pair of tabs.

Another example of the present technology is a positioning and stabilizing structure comprising: a rear strap configured to contact the patient's head and overlay at least a portion of the occipital bone; a pair of upper straps configured to selectively apply a posterior directed tensile force, the pair of upper straps connected to the rear strap inferior to at least a portion of the rear strap; a pair of lower straps configured to selectively apply a posterior directed tensile force, the pair of lower straps connected to the pair of upper straps inferior to at least a portion of the upper straps.

Another example the present technology is a patient interface comprising: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head, the positioning and stabilizing structure comprising: a rear strap configured to contact the patient's head and overlay at least a portion of the occipital bone, the rear strap having a substantially triangular shape; a pair of upper straps formed in a substantially V-shape and connected to an inferior portion of the rear strap; a pair of lower straps formed in a substantially V-shape and connected to an inferior portion of the pair of upper straps, the pair of upper straps and the pair of lower straps connected in a substantially X-shaped configuration; a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breath from ambient through their mouth in the absence of a flow of pressurised air through the plenum chamber inlet port, or the patient interface is configured to leave the patient's mouth uncovered.

Another example of the present technology is a positioning and stabilizing structure comprising: a rear strap configured to contact the patient's head and overlay at least a portion of the occipital bone, the rear strap having a substantially triangular shape; a pair of upper straps formed in a substantially V-shape and connected to an inferior portion of the rear strap; a pair of lower straps formed in a substantially V-shape and connected to an inferior portion of the pair of upper straps, the pair of upper straps and the pair of lower straps connected in a substantially X-shaped configuration.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 2 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 3 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 8:
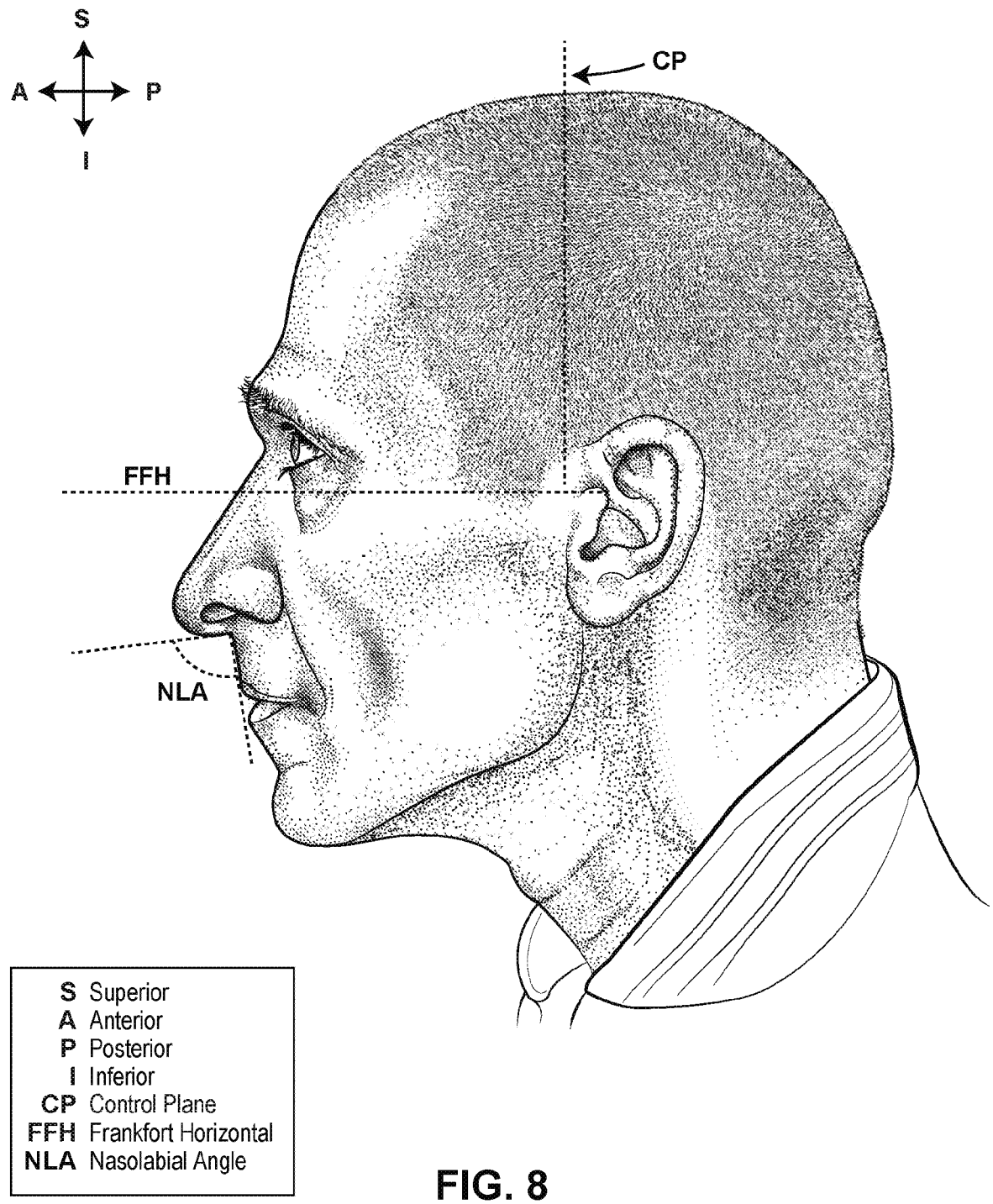

FIG. 8 is a further side view of a head. The approximate locations of the Frankfort horizontal and nasolabial angle are indicated. The coronal plane is also indicated.

Figure 9:
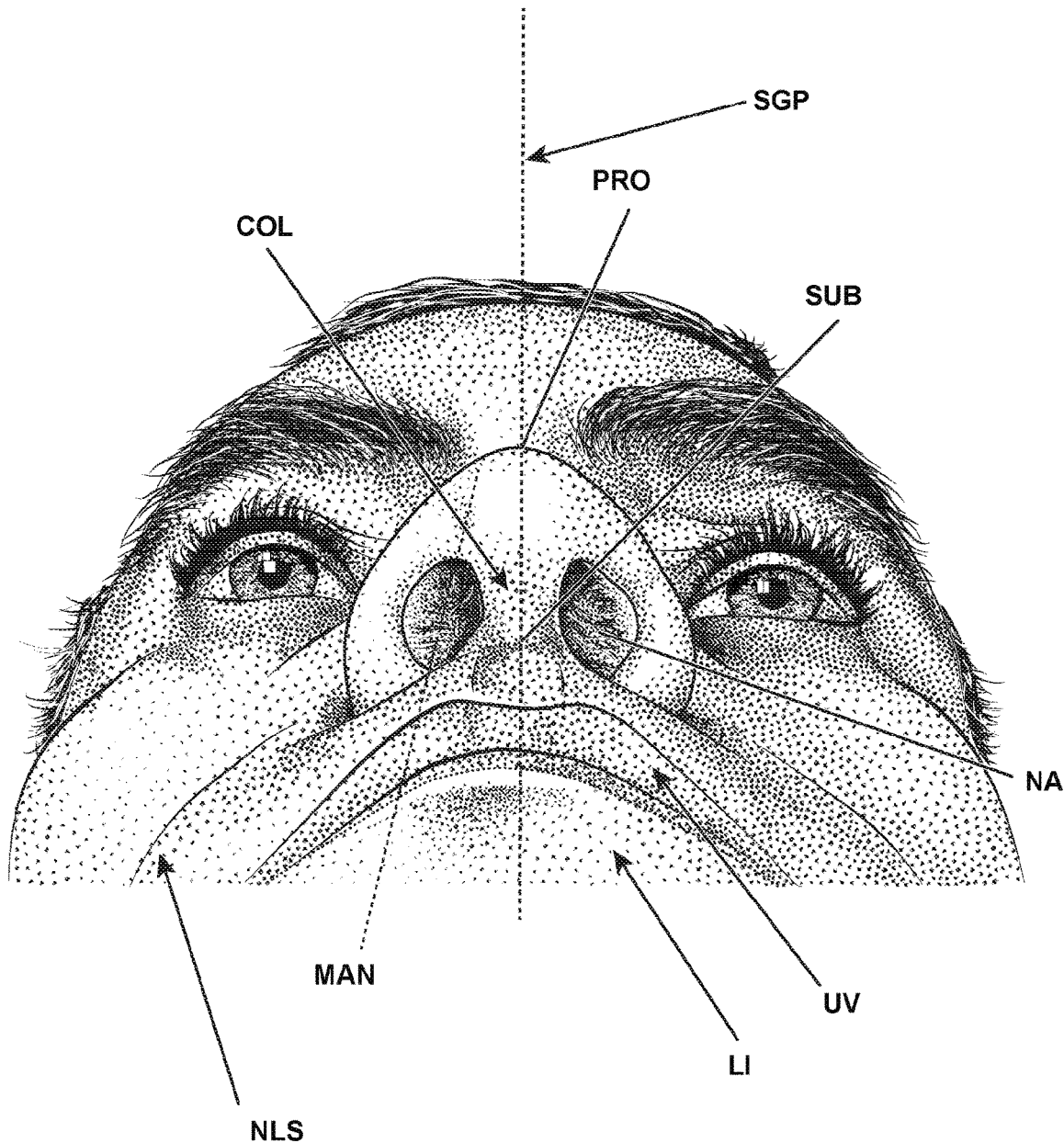

FIG. 9 shows a base view of a nose with several features identified including naso-labial sulcus, lip inferior, upper Vermilion, naris, subnasale, columella, pronasale, the major axis of a naris and the midsagittal plane.

FIG. 10 shows a side view of the superficial features of a nose.

FIG. 11 shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 12 shows a medial dissection of a nose, approximately several millimeters from the midsagittal plane, amongst other things showing the septum cartilage and medial crus of greater alar cartilage.

Figures 13, 14:
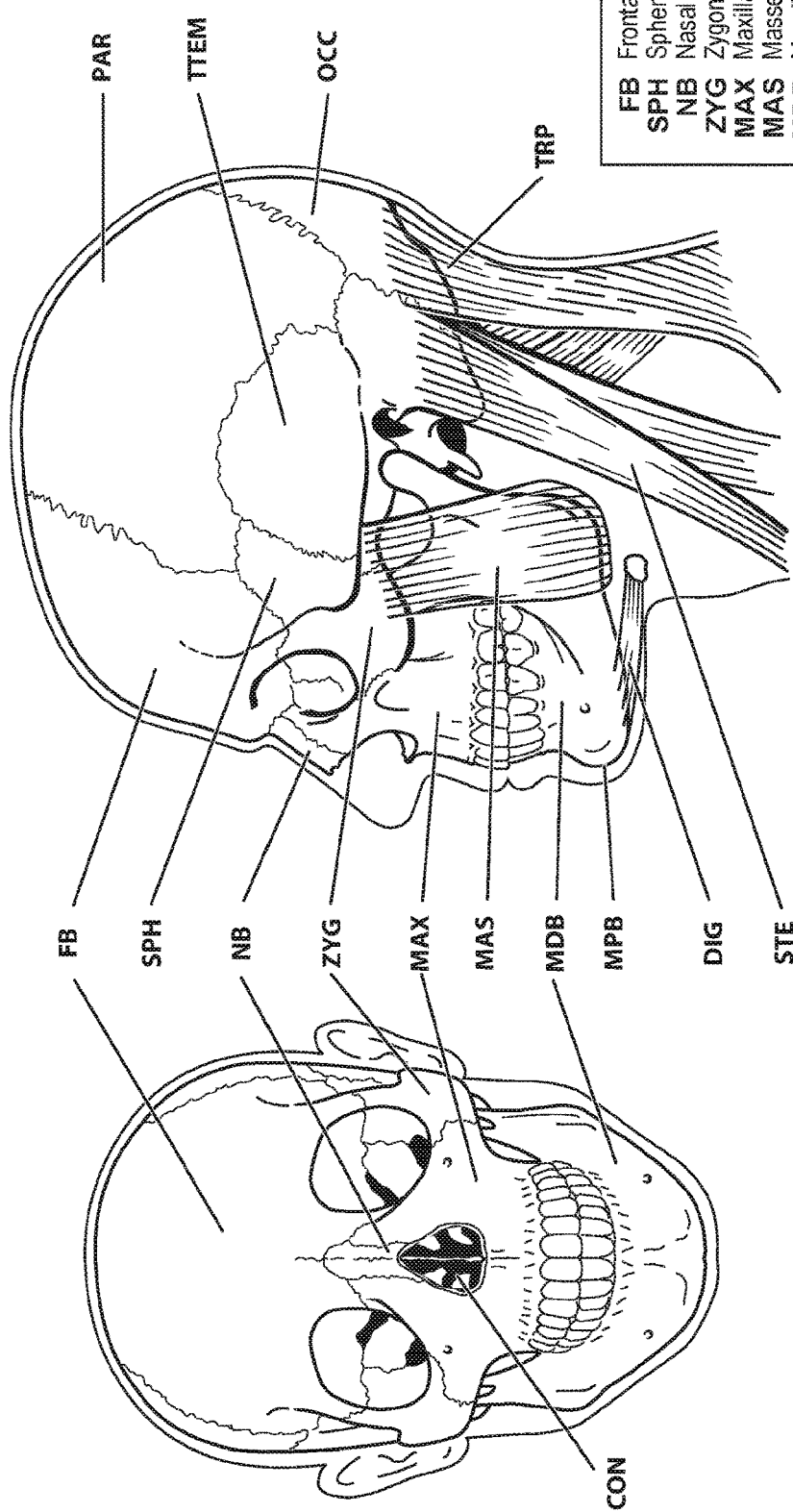

FIG. 13 shows a front view of the bones of a skull including the frontal, nasal and zygomatic bones. Nasal concha are indicated, as are the maxilla, and mandible.

FIG. 14 shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 15:
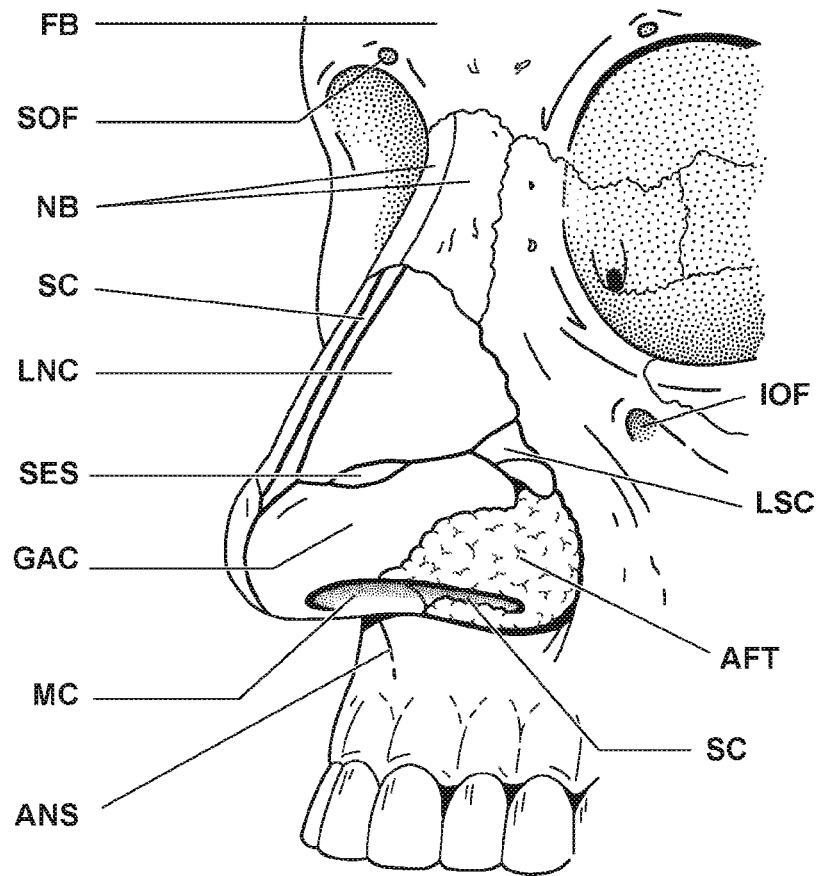

FIG. 15 shows an anterolateral view of a nose.

4.3 Patient Interface

Figure 16:
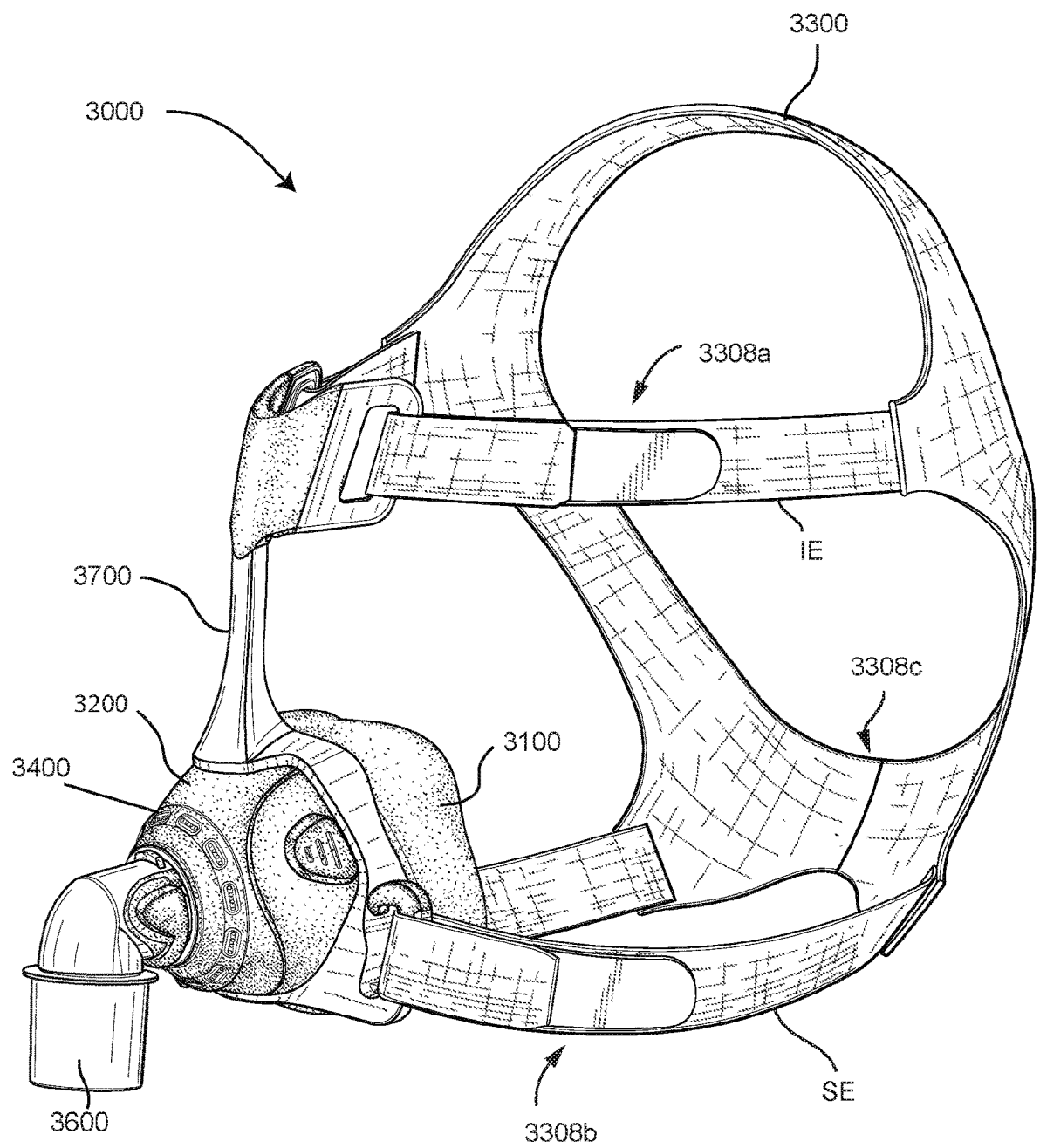

FIG. 16 shows a patient interface in the form of a nasal mask in accordance with one form of the present technology.

Figure 17:
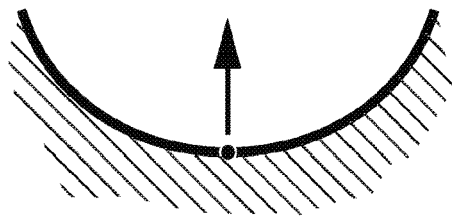

FIG. 17 shows a schematic of a cross-section through a structure at a point. An outward normal at the point is indicated. The curvature at the point has a positive sign, and a relatively large magnitude when compared to the magnitude of the curvature shown in FIG. 18.

Figure 18:
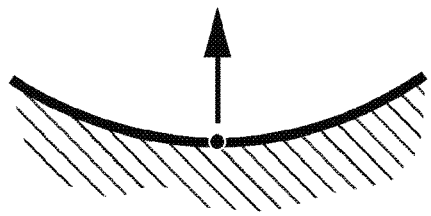

FIG. 18 shows a schematic of a cross-section through a structure at a point. An outward normal at the point is indicated. The curvature at the point has a positive sign, and a relatively small magnitude when compared to the magnitude of the curvature shown in FIG. 17.

Figure 19:
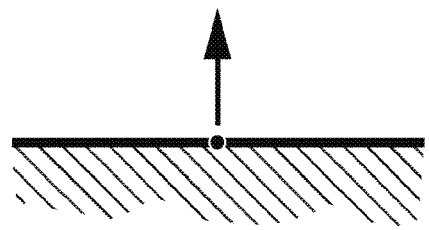

FIG. 19 shows a schematic of a cross-section through a structure at a point. An outward normal at the point is indicated. The curvature at the point has a value of zero.

Figure 20:
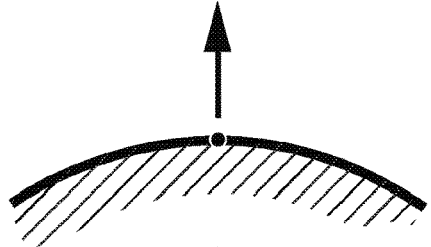

FIG. 20 shows a schematic of a cross-section through a structure at a point. An outward normal at the point is indicated. The curvature at the point has a negative sign, and a relatively small magnitude when compared to the magnitude of the curvature shown in FIG. 21.

Figure 21:
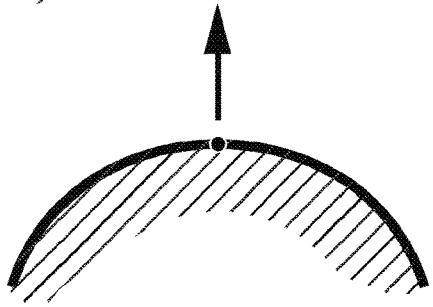

FIG. 21 shows a schematic of a cross-section through a structure at a point. An outward normal at the point is indicated. The curvature at the point has a negative sign, and a relatively large magnitude when compared to the magnitude of the curvature shown in FIG. 20.

Figure 22:
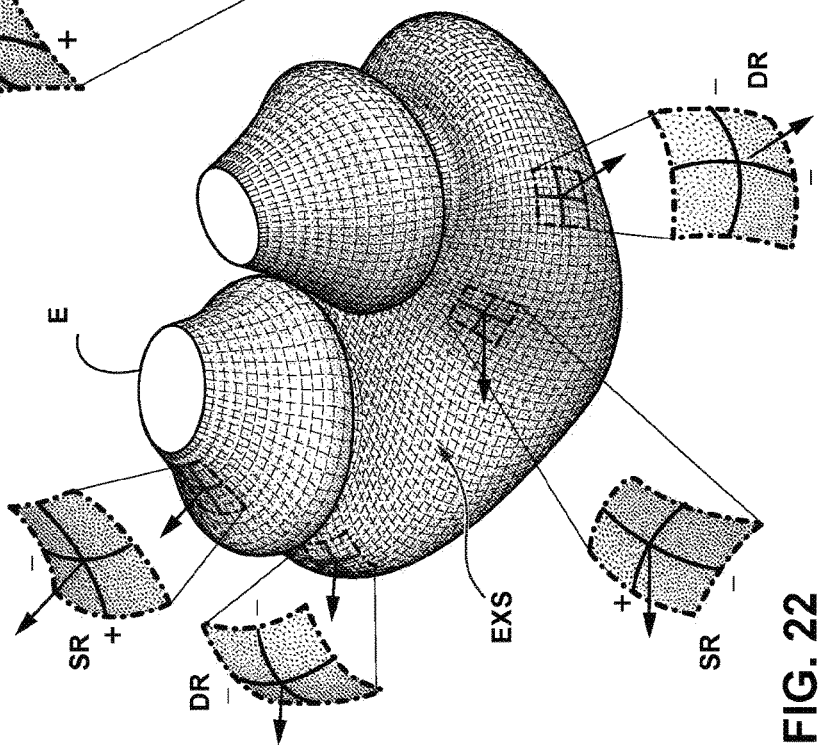

FIG. 22 shows a cushion for a mask that includes two pillows. An exterior surface of the cushion is indicated. An edge of the surface is indicated. Dome and saddle regions are indicated.

Figure 23:
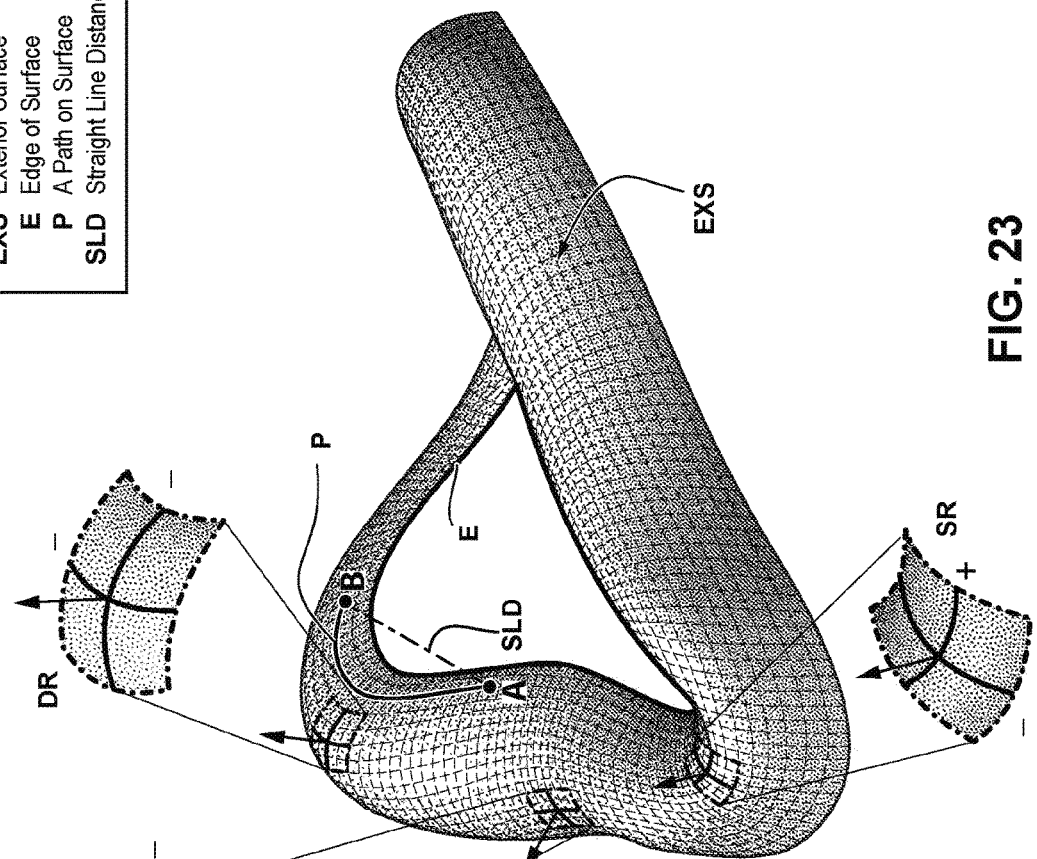

FIG. 23 shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 24:
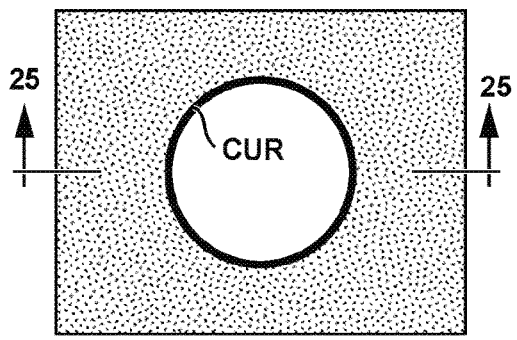

FIG. 24 shows the surface of a structure, with a one dimensional hole in the surface. The illustrated plane curve forms the boundary of a one dimensional hole.

Figure 25:
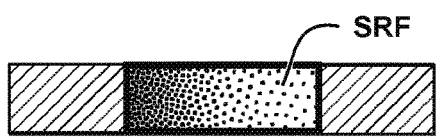

FIG. 25 shows a cross-section through the structure of FIG. 24. The illustrated surface bounds a two dimensional hole in the structure of FIG. 24.

Figure 26:
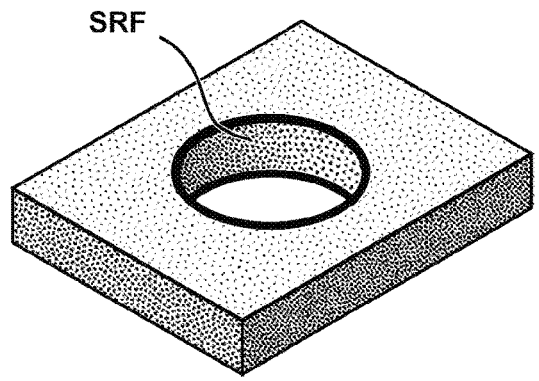

FIG. 26 shows a perspective view of the structure of FIG. 24, including the two dimensional hole and the one dimensional hole. Also shown is the surface that bounds a two dimensional hole in the structure of FIG. 24.

Figure 27:
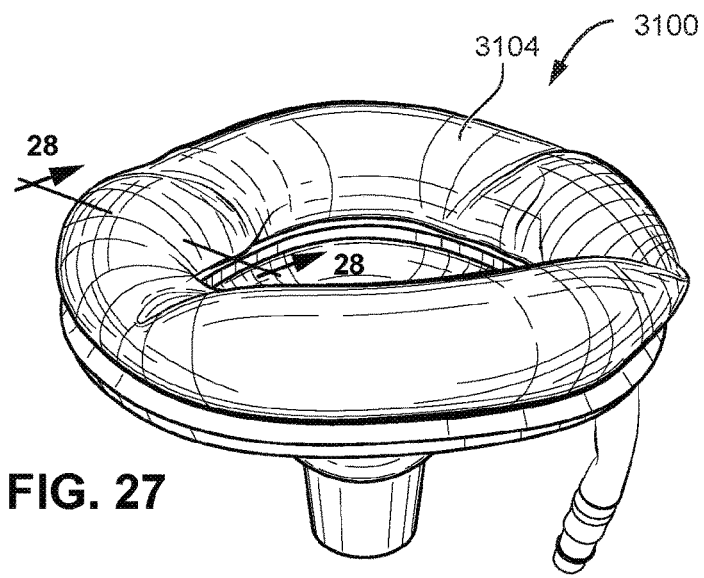

FIG. 27 shows a mask having an inflatable bladder as a cushion.

Figure 28:
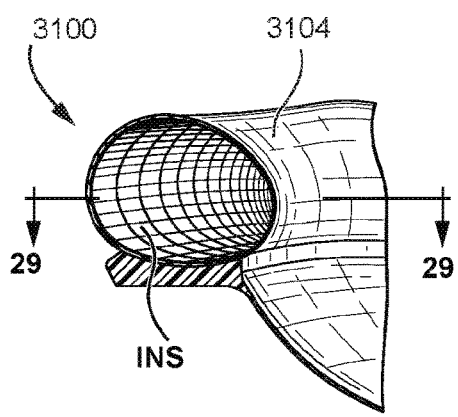

FIG. 28 shows a cross-section through the mask of FIG. 27, and shows the interior surface of the bladder. The interior surface bounds the two dimensional hole in the mask.

Figure 29:
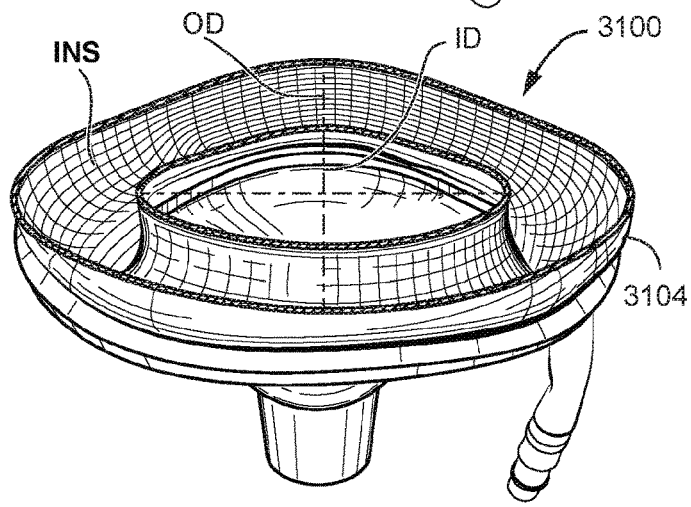

FIG. 29 shows a further cross-section through the mask of FIG. 27. The interior surface is also indicated.

FIG. 30 illustrates a left-hand rule.

FIG. 31 illustrates a right-hand rule.

FIG. 32 shows a left ear, including the left ear helix.

FIG. 33 shows a right ear, including the right ear helix.

FIG. 34 shows a right-hand helix.

FIG. 35 shows a view of a mask, including the sign of the torsion of the space curve defined by the edge of the sealing membrane in different regions of the mask.

Figure 36:
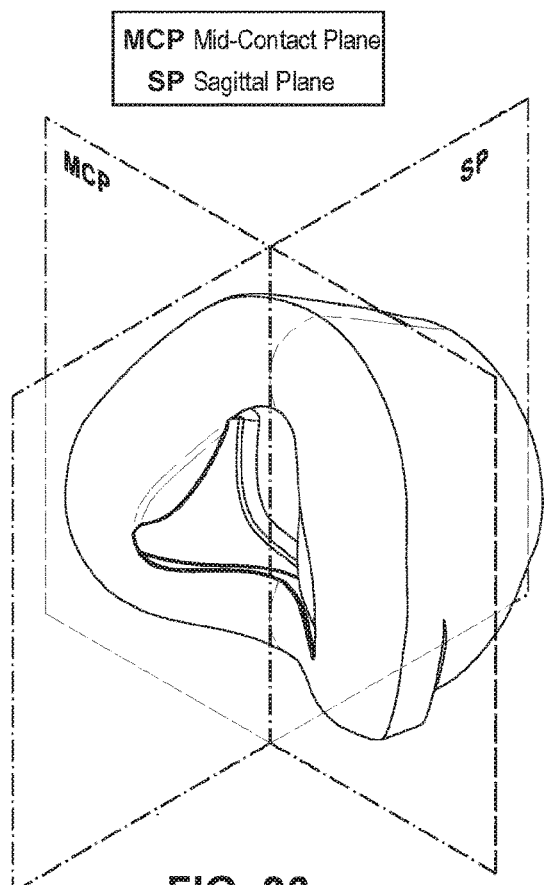

FIG. 36 shows a view of a plenum chamber 3200 showing a sagittal plane and a mid-contact plane.

Figure 37:
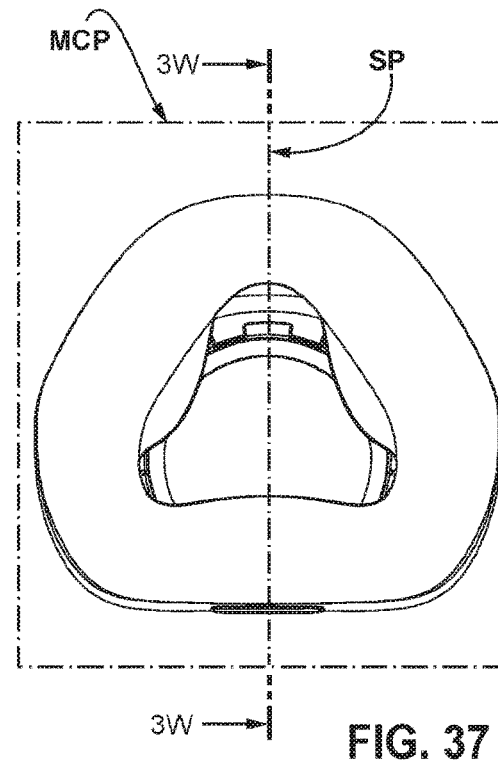

FIG. 37 shows a view of a posterior of the plenum chamber of FIG. 36. The direction of the view is normal to the mid-contact plane. The sagittal plane in FIG. 37 bisects the plenum chamber into left-hand and right-hand sides.

Figure 38:
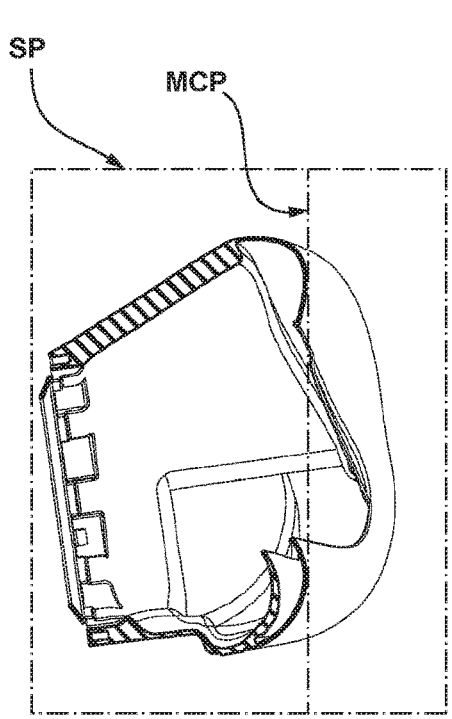

FIG. 38 shows a cross-section through the plenum chamber of FIG. 37, the cross-section being taken at the sagittal plane shown in FIG. 37. A 'mid-contact' plane is shown. The mid-contact plane is perpendicular to the sagittal plane. The orientation of the mid-contact plane corresponds to the orientation of a chord 3215 which lies on the sagittal plane and just touches the cushion of the plenum chamber at two points on the sagittal plane: a superior point 3225 and an inferior point 3235. Depending on the geometry of the cushion in this region, the mid-contact plane may be a tangent at both the superior and inferior points.

Figure 39:
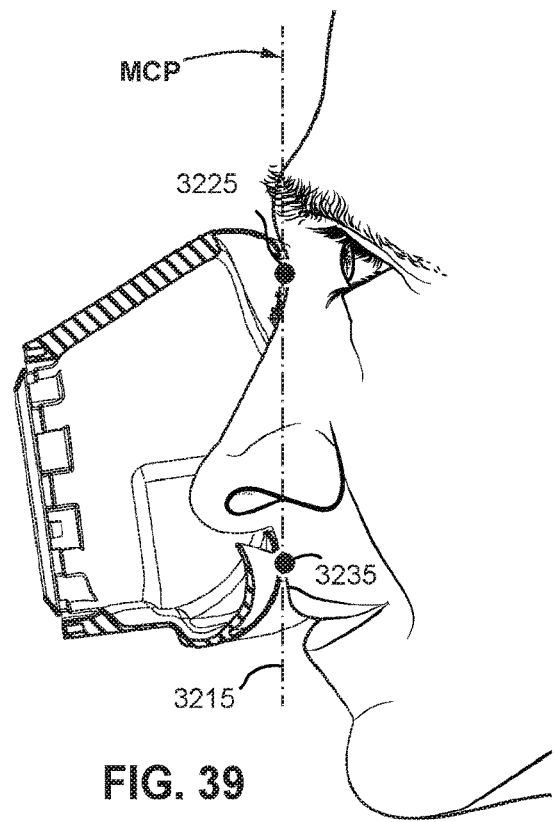

FIG. 39 shows the plenum chamber 3200 of FIG. 36 in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 39 the plenum chamber 3200 is that of a nasal mask, and the superior point 3225 sits approximately on the sellion, while the inferior point 3235 sits on the lip superior.

4.4 RPT Device

Figure 40:
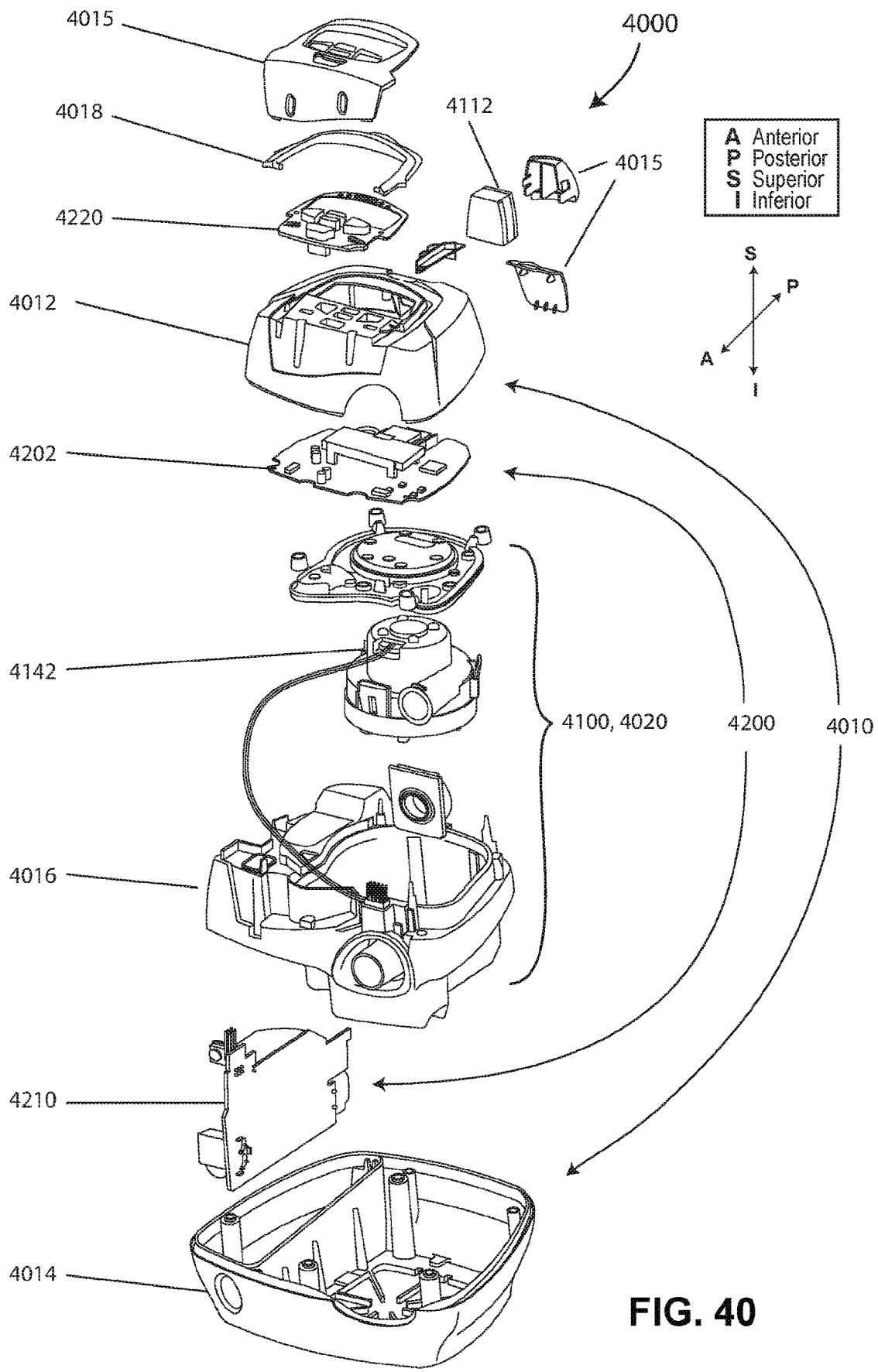

FIG. 40 shows an RPT device in accordance with one form of the present technology.

Figure 41:
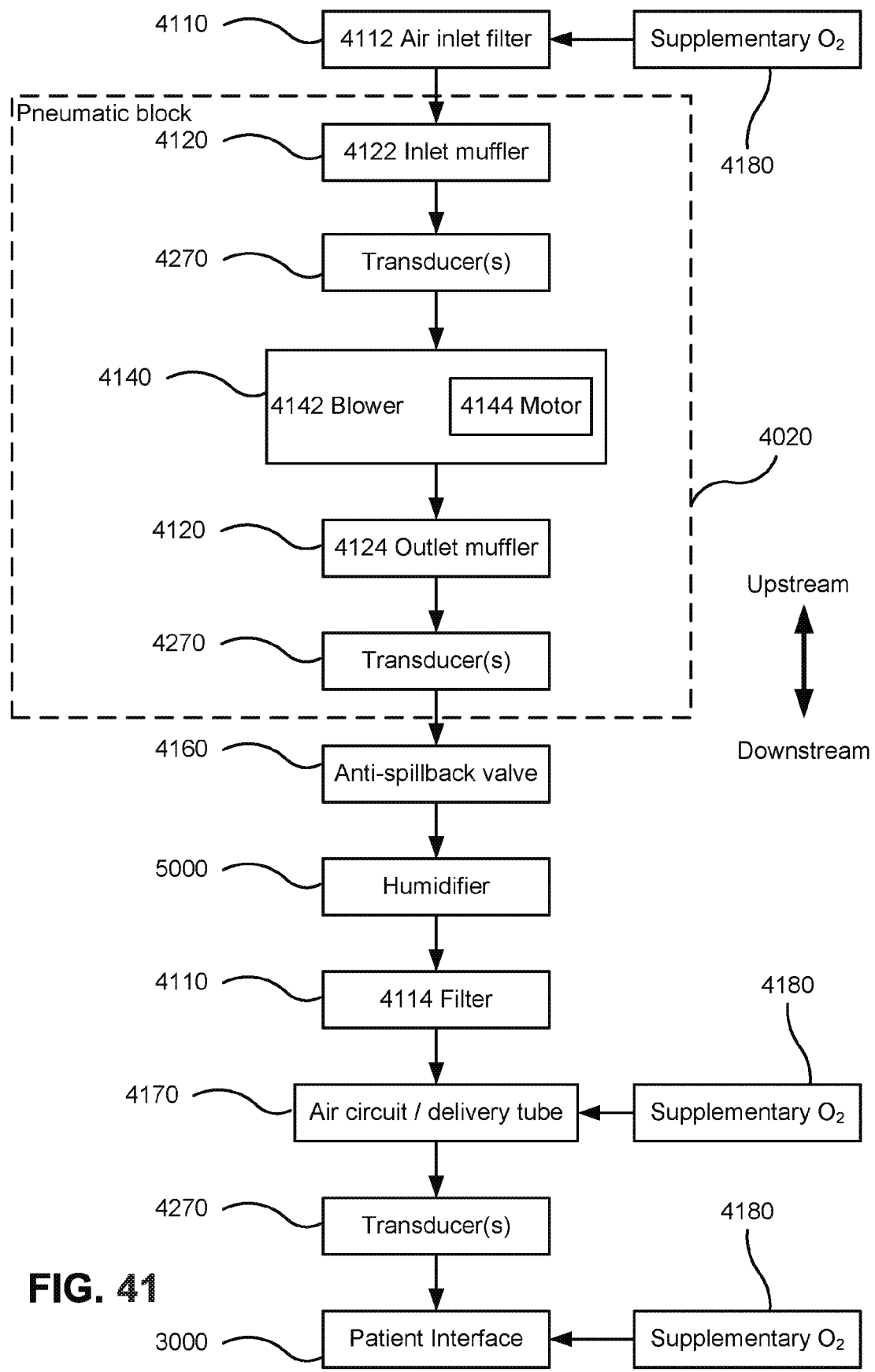

FIG. 41 is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Breathing Waveforms

Figure 42:
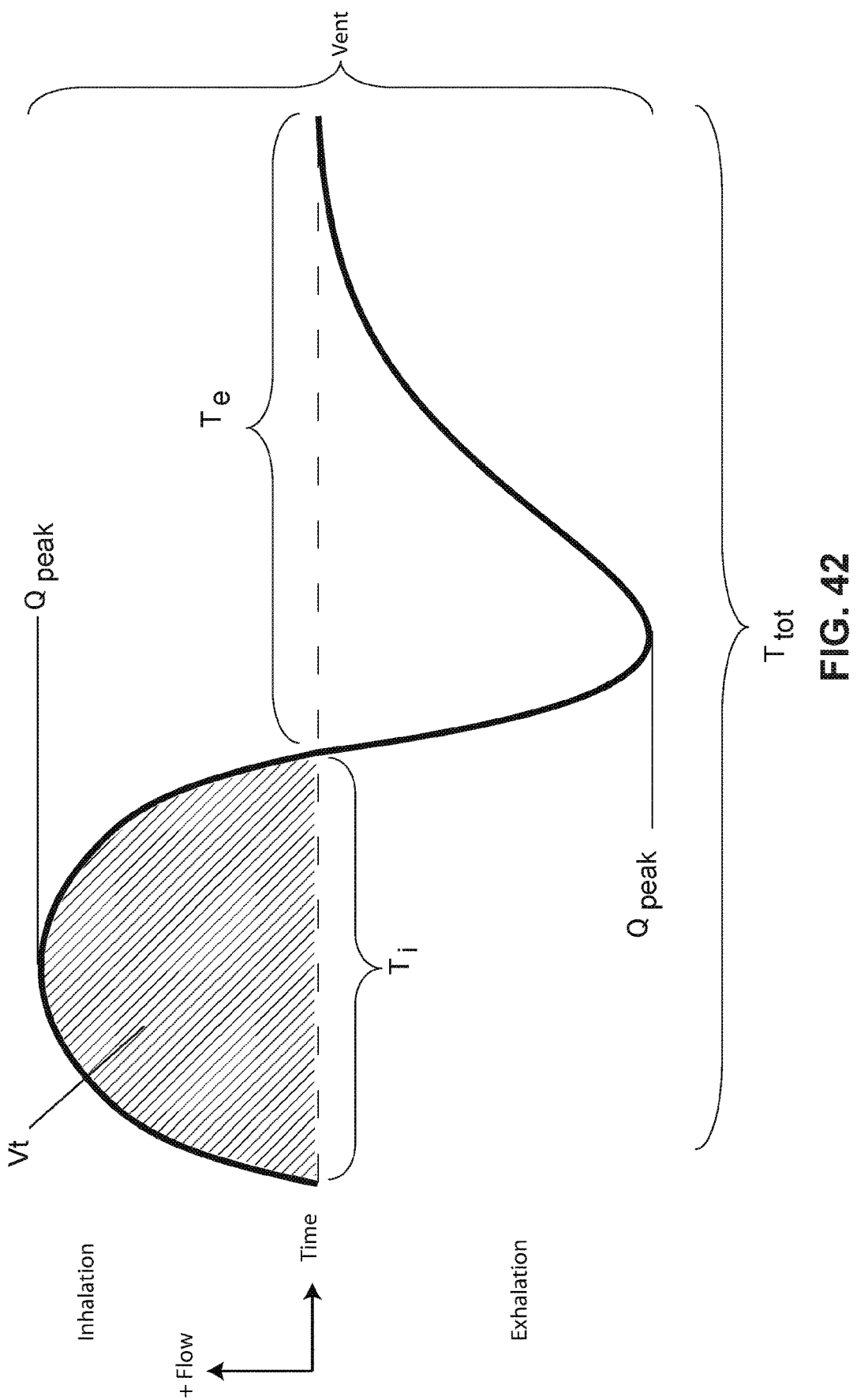

FIG. 42 shows a model typical breath waveform of a person while sleeping.

4.6 Patient Interface of the Present Technology

Figure 43:
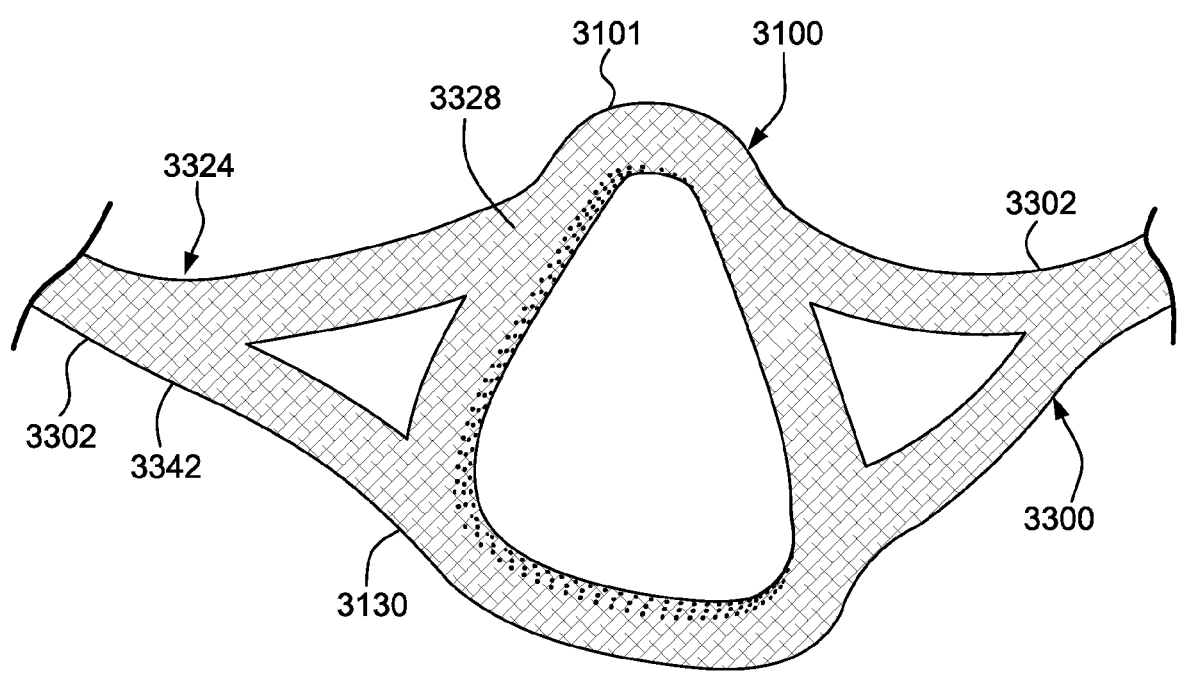

FIG. 43 shows a one piece textile construction used to make a seal-forming structure and positioning and stabilizing structure.

Figure 44:
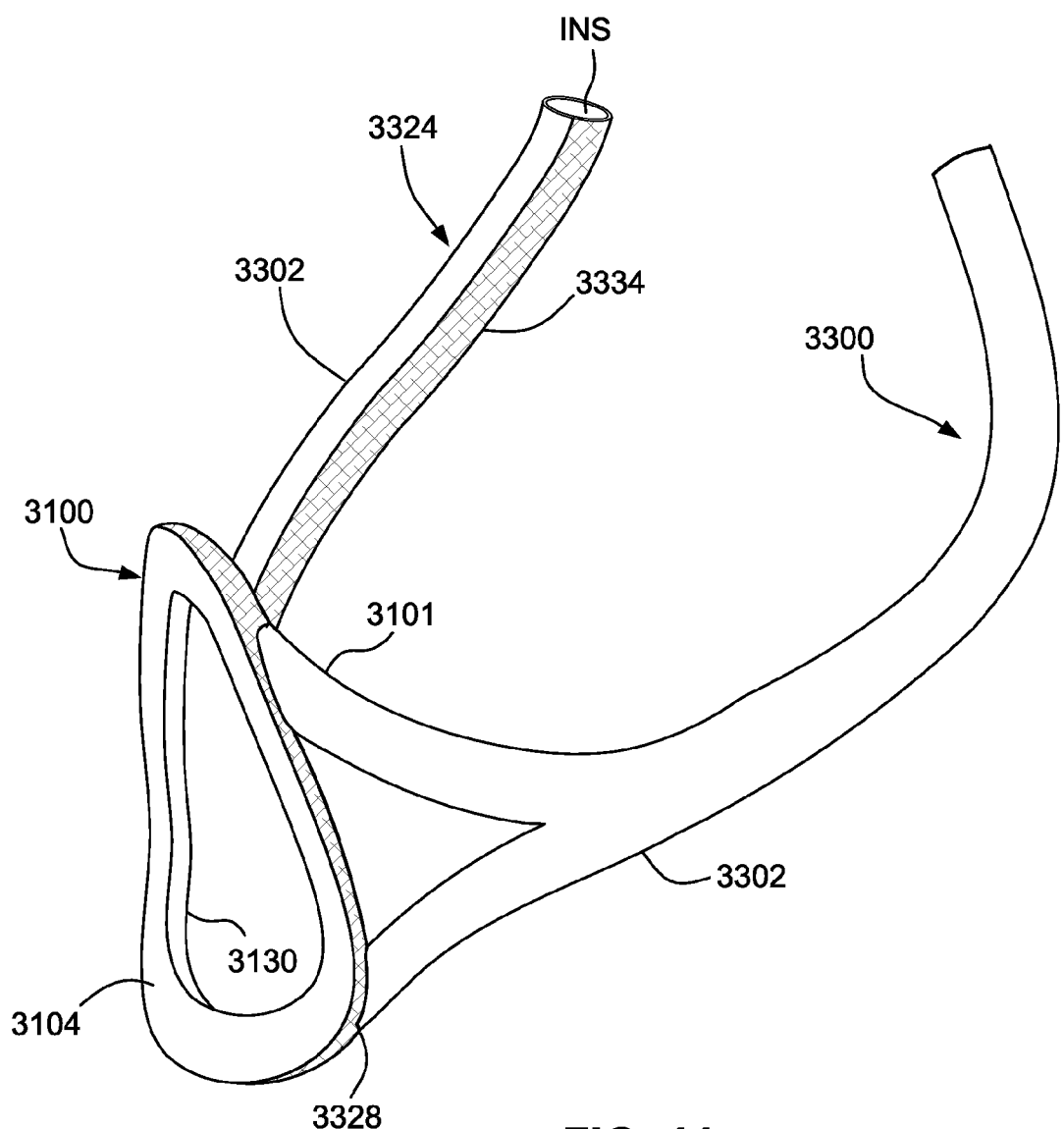

FIG. 44 shows a seal-forming structure and a positioning and stabilizing structure that are formed from a one piece fabric construction as shown in FIG. 43. The positioning and stabilizing structure is formed as a hollow tube that conveys air toward the seal-forming structure.

Figure 45:
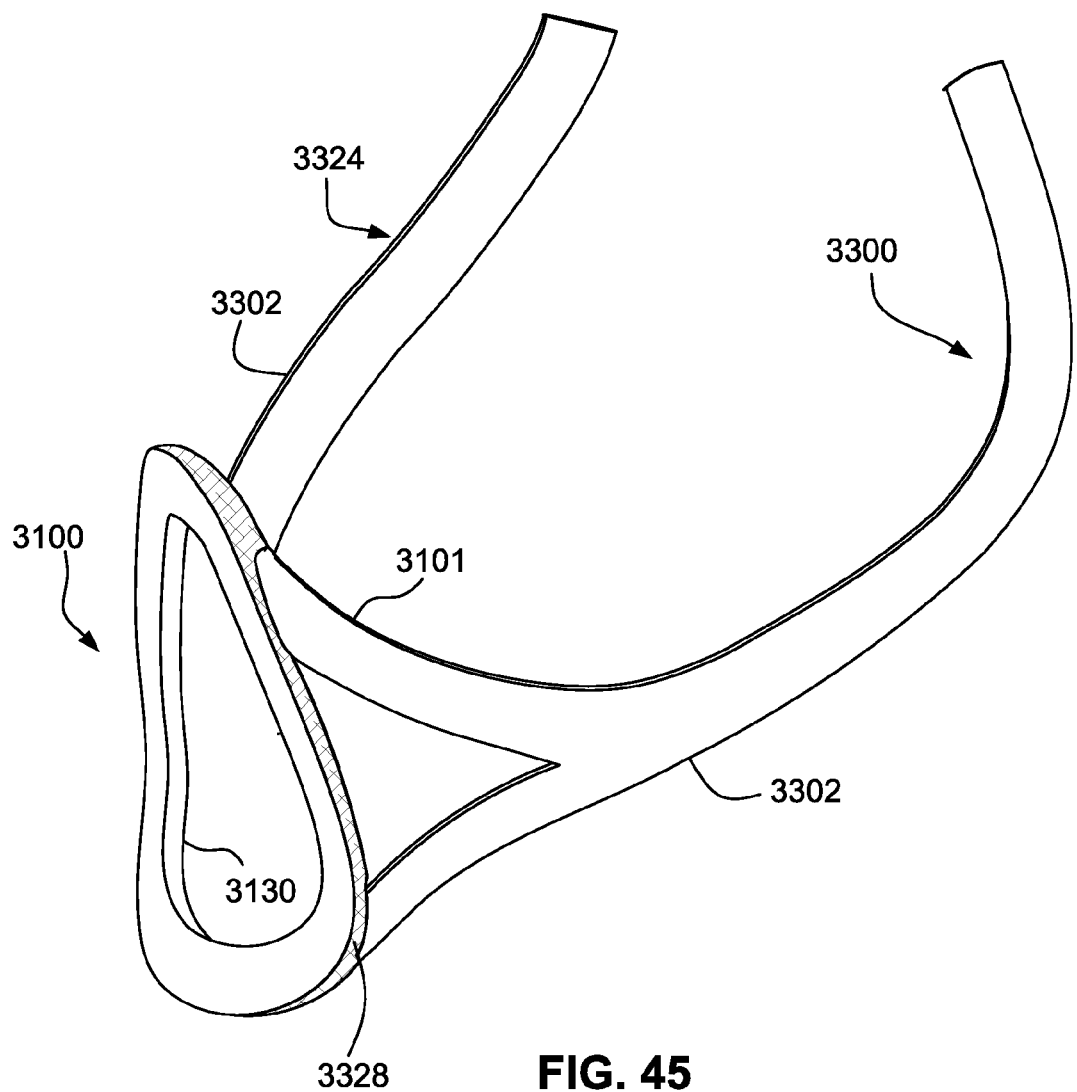

FIG. 45 shows a seal-forming structure and a positioning and stabilizing structure that are formed from a one piece fabric construction as shown in FIG. 43. The positioning and stabilizing structure is formed as flat straps.

Figure 46:
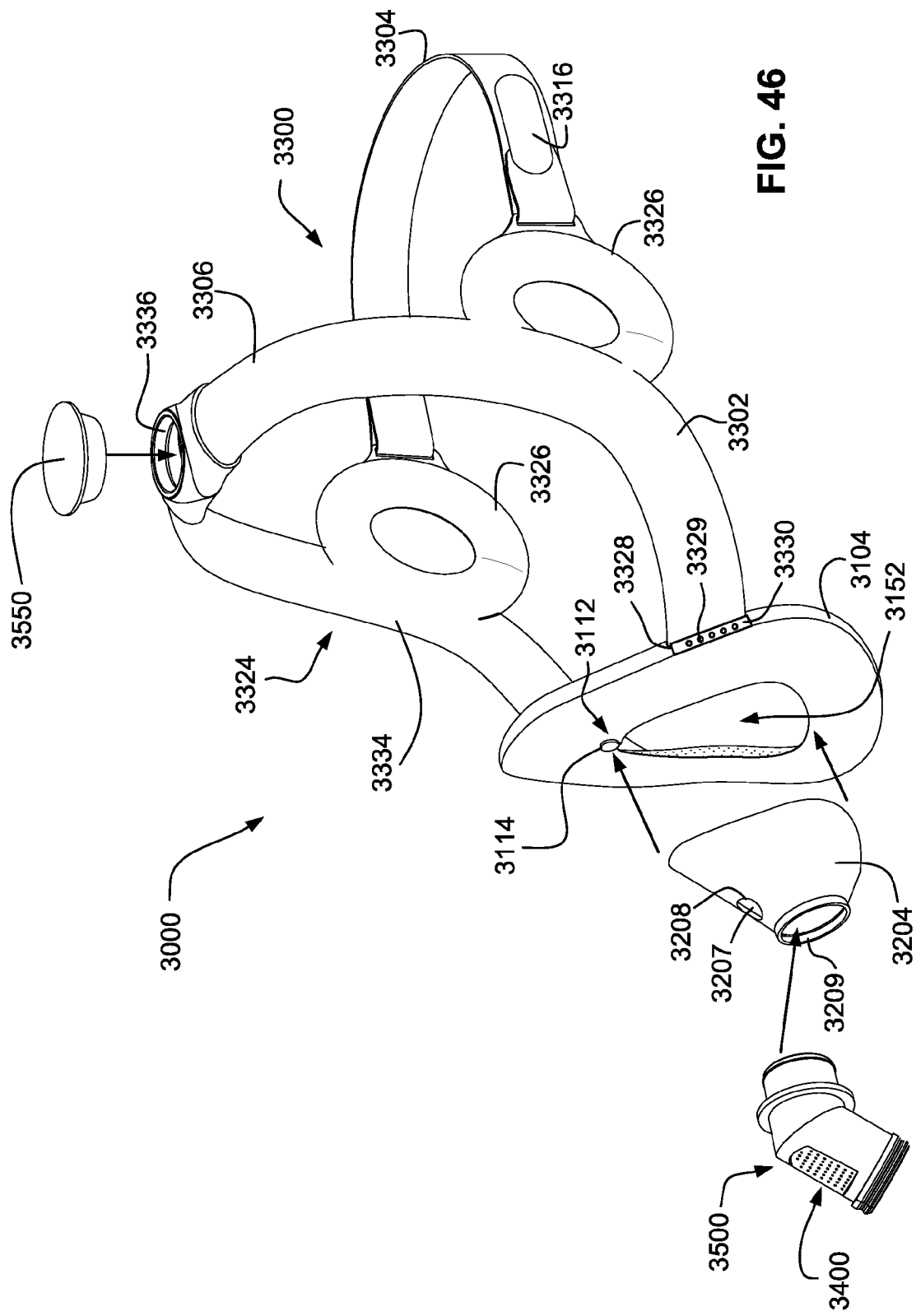

FIG. 46 shows a front perspective view of a patient interface formed from a one piece construction of textile material. The positioning and stabilizing structure includes hollow tubes that convey air toward the seal-forming structure. The air is conveyed directly into a hollow sealing tube and the seal-forming structure. A plenum chamber is removably coupled to the seal-forming structure. Air may be provided to the hollow sealing tube through a decoupling member positioned in either the positioning and stabilizing structure or the plenum chamber.

FIG. 47 shows a rear perspective view of the patient interface of FIG. 46. The plenum chamber includes a pair of magnetic portions that assist in coupling the plenum chamber to the seal-forming structure in the proper orientation.

FIG. 48 shows a detail view of the patient interface of FIG. 47 that shows an interior surface of the hollow sealing tube. The seal-forming structure includes holes in communication with the hollow sealing tube. The holes allow air to be conveyed from proximate the interior surface towards the patient's face.

FIG. 49 shows a perspective view of a patient interface formed from a one piece construction of textile material. A seal-forming structure includes a clipping structures and a magnetic portion. A plenum chamber is received by the clipping structure and includes a magnetic portion that is complementary to the portion on the seal-forming structure. The clipping structure and the magnetic portions work together to assist in coupling the plenum chamber to the seal-forming structure.

FIG. 50a shows a perspective view of the patient interface of FIG. 49. The plenum chamber is partially coupled to the seal-forming structure using the clipping structure and the magnetic portions.

FIG. 50b shows a perspective view of the patient interface of FIG. 49. The plenum chamber is fully coupled to the seal-forming structure using the clipping structure and the magnetic portions.

Figure 51:
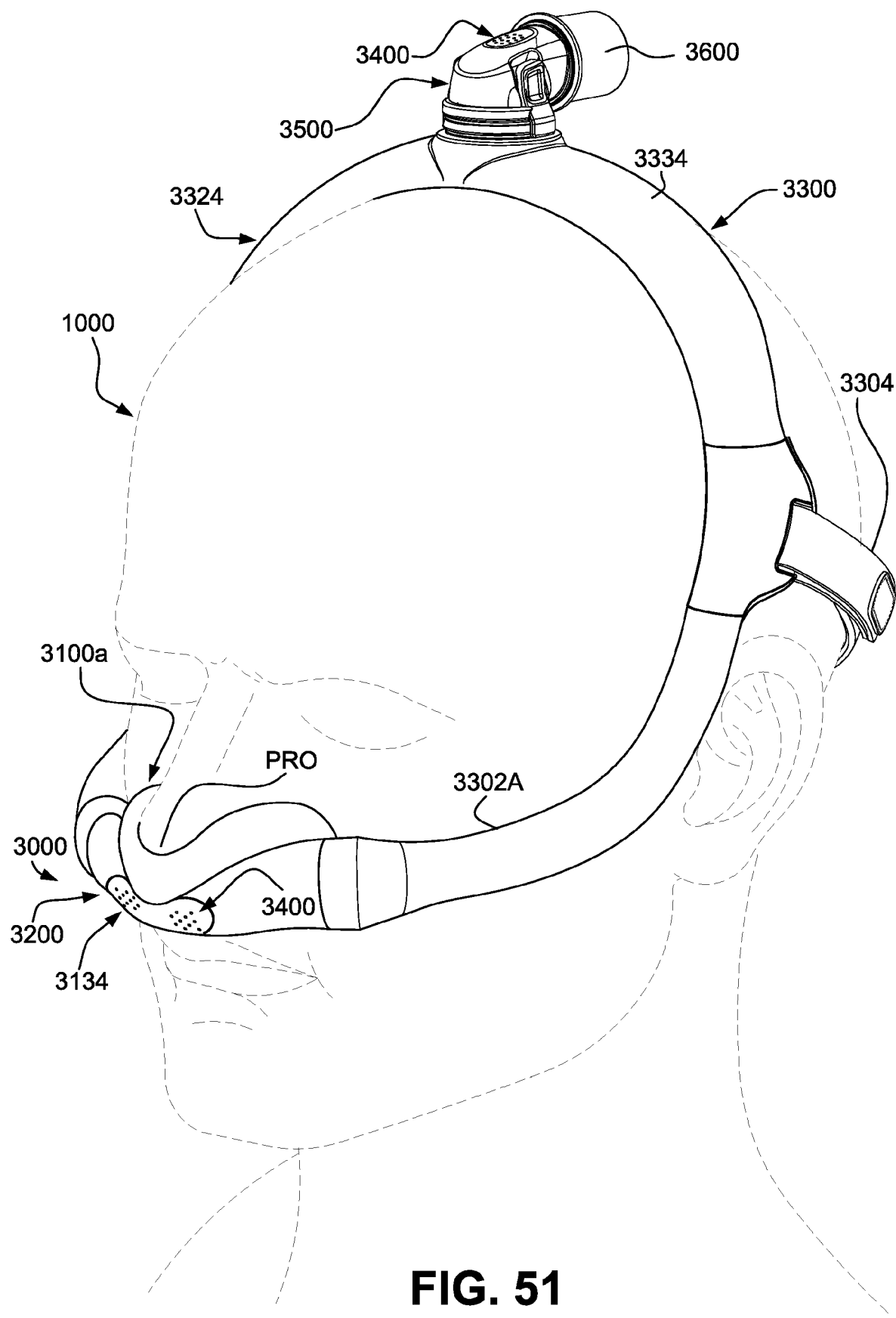

FIG. 51 shows a perspective view of an under the nose mask worn by a patient. The mask creates a seal around the patient's nares, and leaves the patient's mouth exposed to the ambient.

Figure 52:
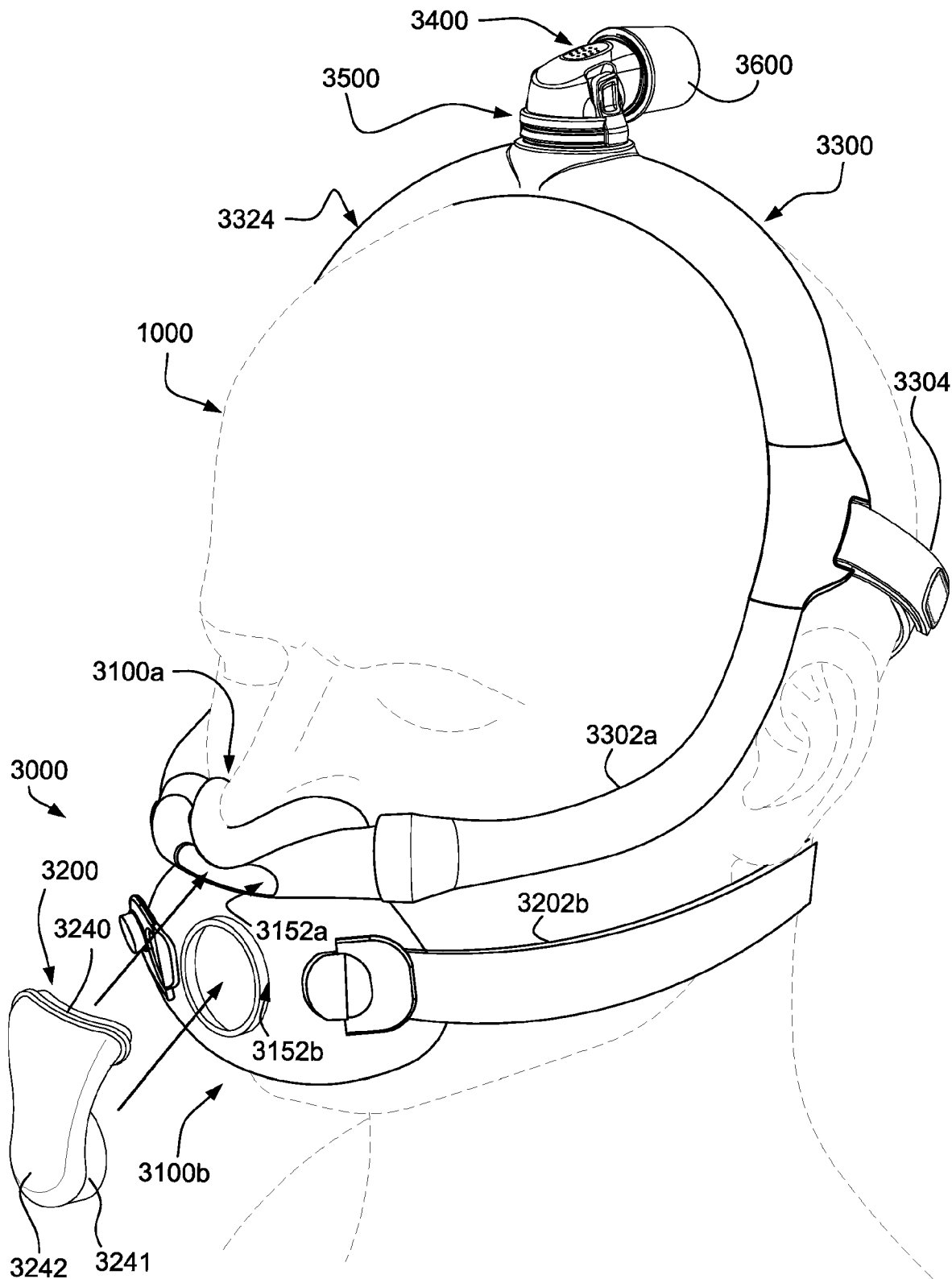

FIG. 52 shows a perspective view of the under the nose mask of FIG. 51 coupled to a mouth seal. Together, the under the nose mask and the mouth seal form a modular construction that can create a seal about the patient's nose and mouth. A plenum chamber is used with the modular configuration in order to selectively cover the patient's mouth and nose from the ambient.

Figure 52A:
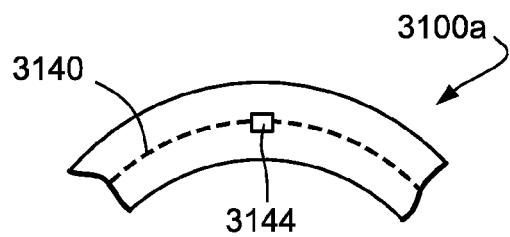

FIG. 52a shows a schematic view of a lower surface of the nose mask of FIG. 51, with an interface to couple to the mouth seal.

Figure 52B:
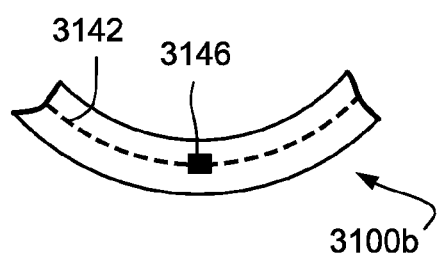

FIG. 52b shows a schematic view of an upper surface of the mouth seal of FIG. 51, with an interface to couple to the nose mask.

Figure 53:
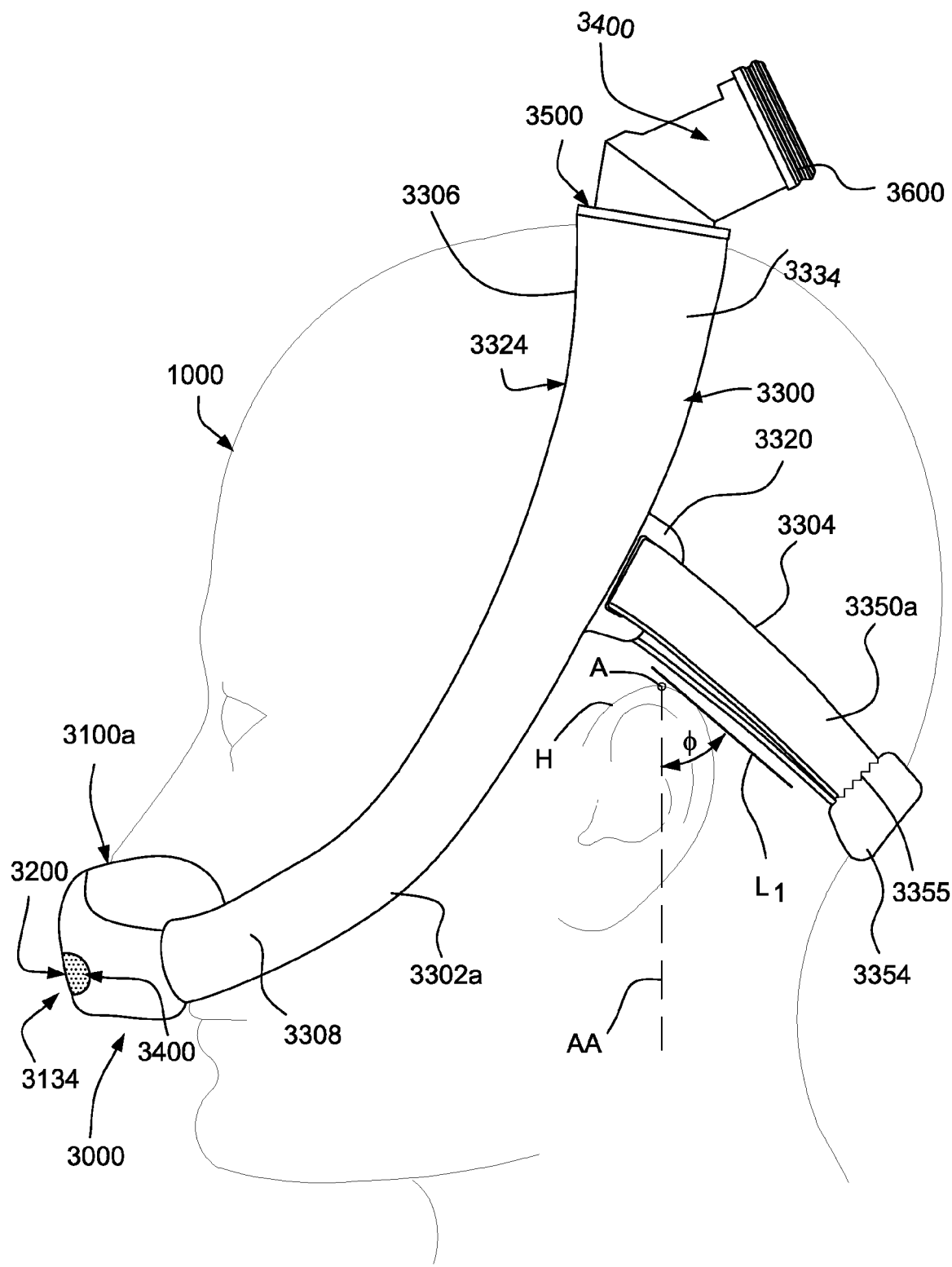

FIG. 53 shows a side view of the under the nose mask of FIG. 51, with a rear strap made from two materials positioned around the patient's head.

Figure 54:
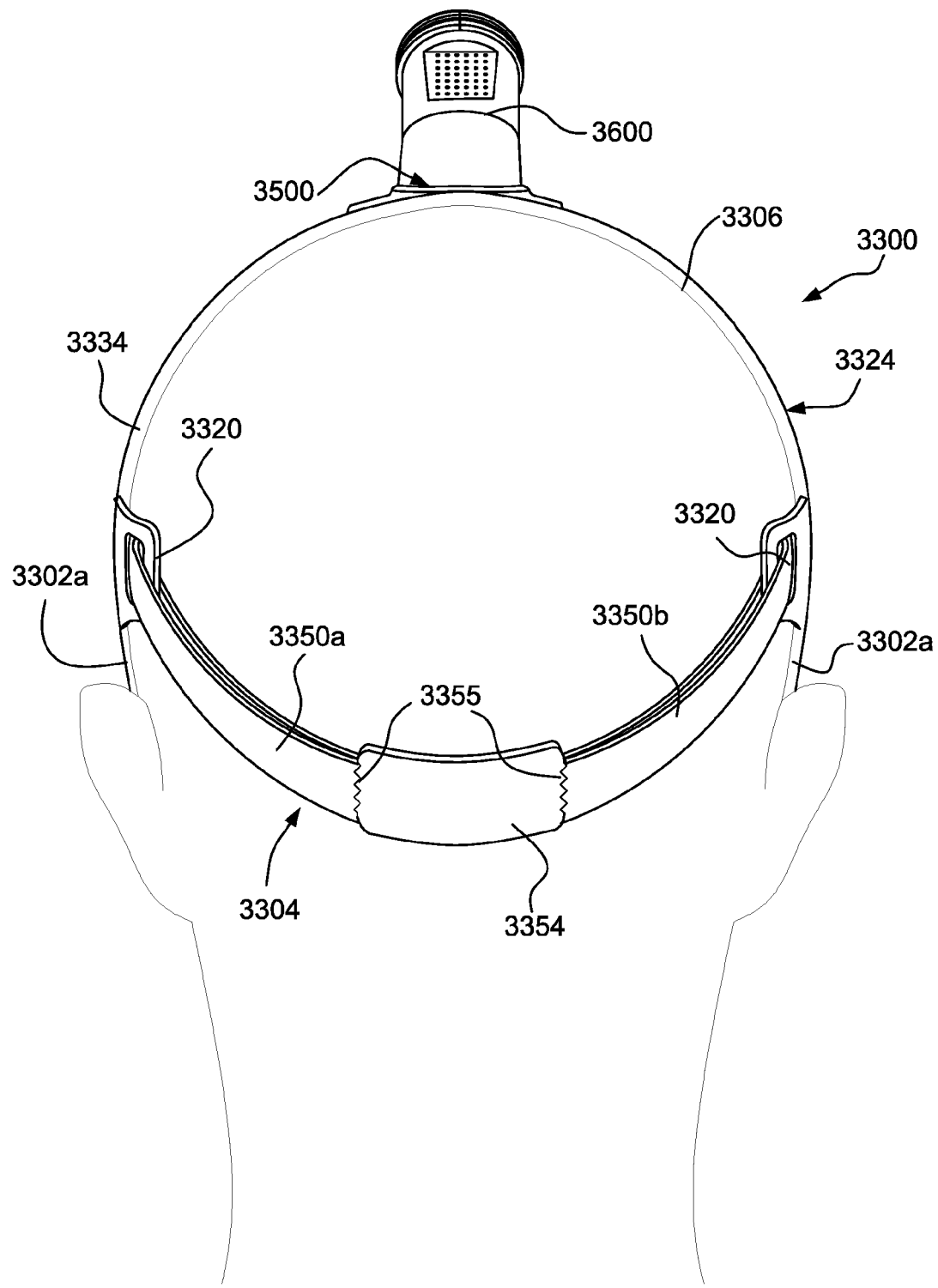

FIG. 54 shows a rear view of the under the nose mask of FIG. 53, illustrating the rear strap with a side portion constructed from a first material and a second section constructed from a second material.

Figure 55:
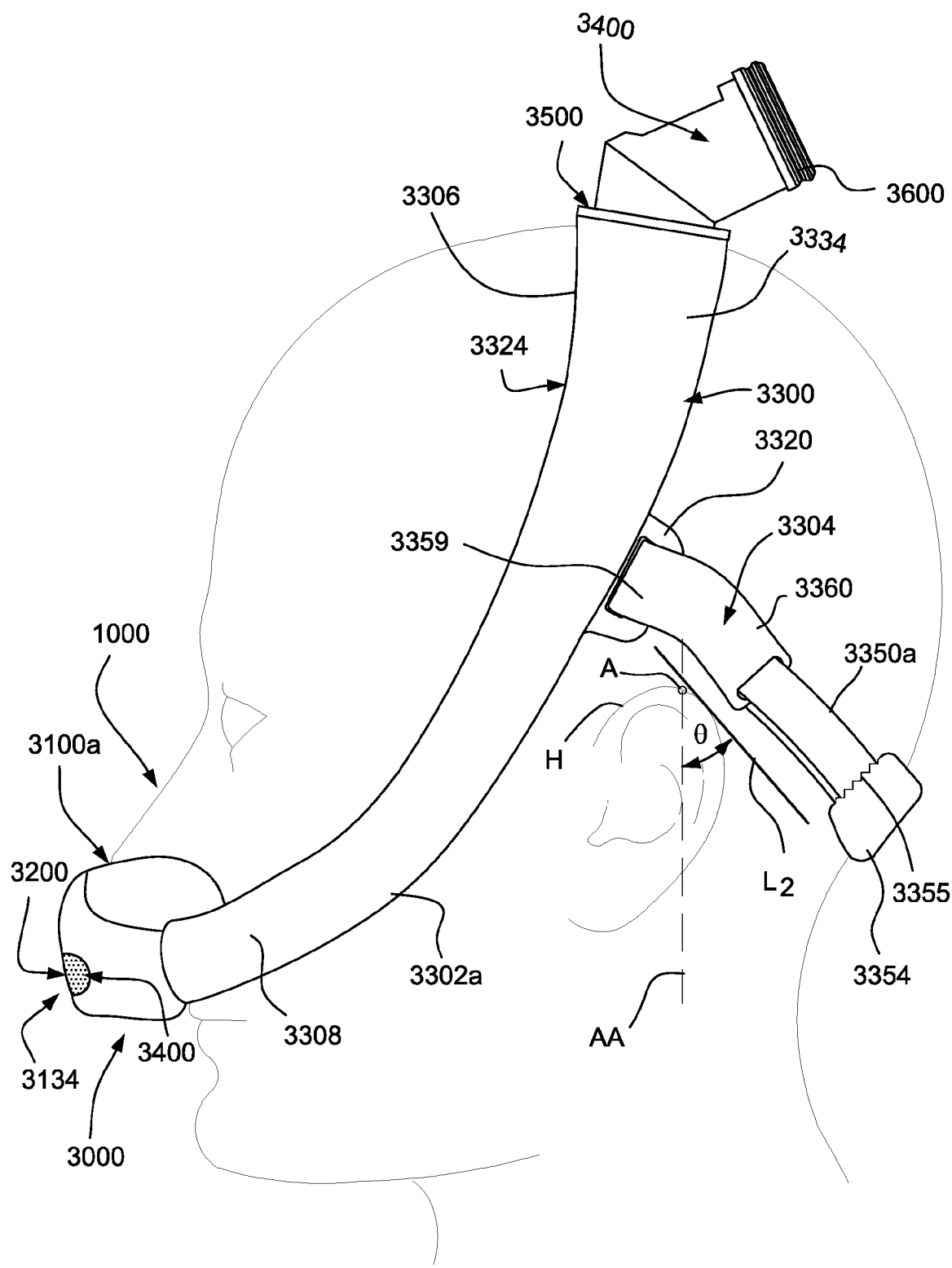

FIG. 55 shows a side view of the under the nose mask of FIG. 51, with a rear strap made from two materials positioned around the patient's head. An extender is used to couple the rear strap to a hollow tube.

Figure 56:
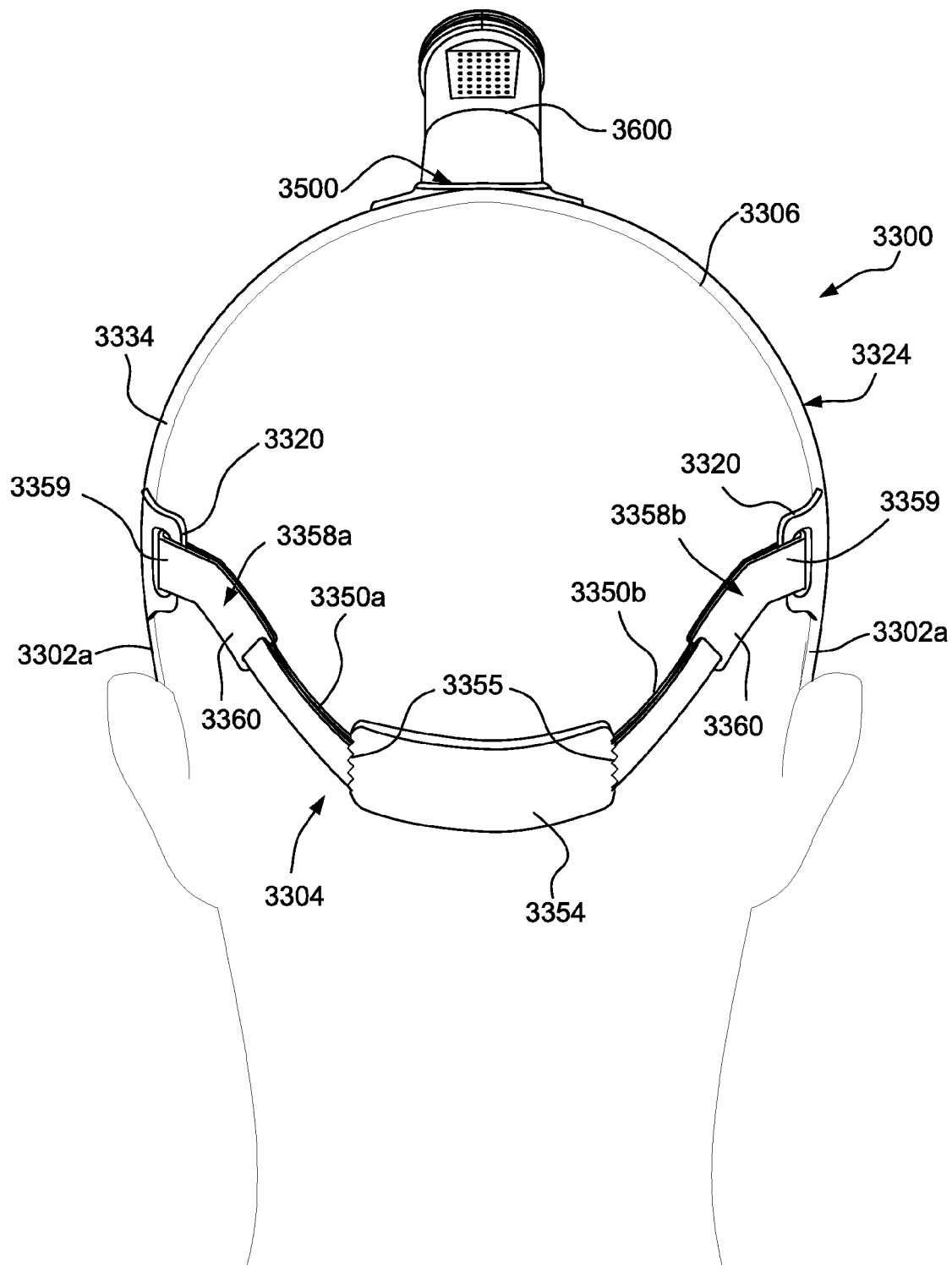

FIG. 56 shows a rear view of the under the nose mask of FIG. 55, illustrating the rear strap with a side portion constructed from a first material and a second section constructed from a second material. The extender is constructed from a third material that differs from the first material.

Figure 57:
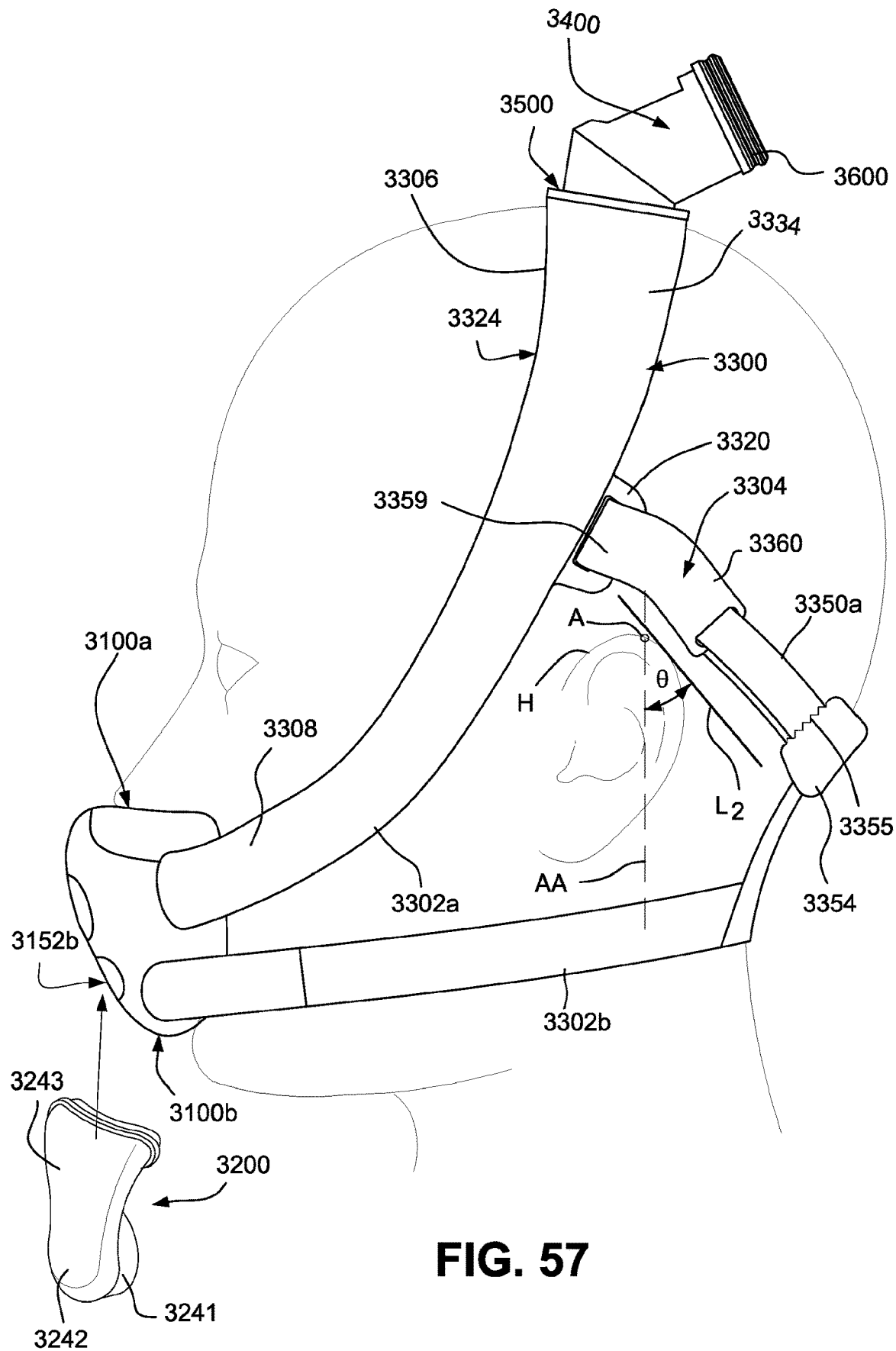

FIG. 57 shows a side view of the under the nose mask and mouth seal of FIG. 52, with a rear strap made from two materials positioned around the patient's head. An extender is used to couple the rear strap to a hollow tube, and an additional side strap is used to maintain the under the nose mask and mouth seal in a therapeutically effective position.

Figure 58:
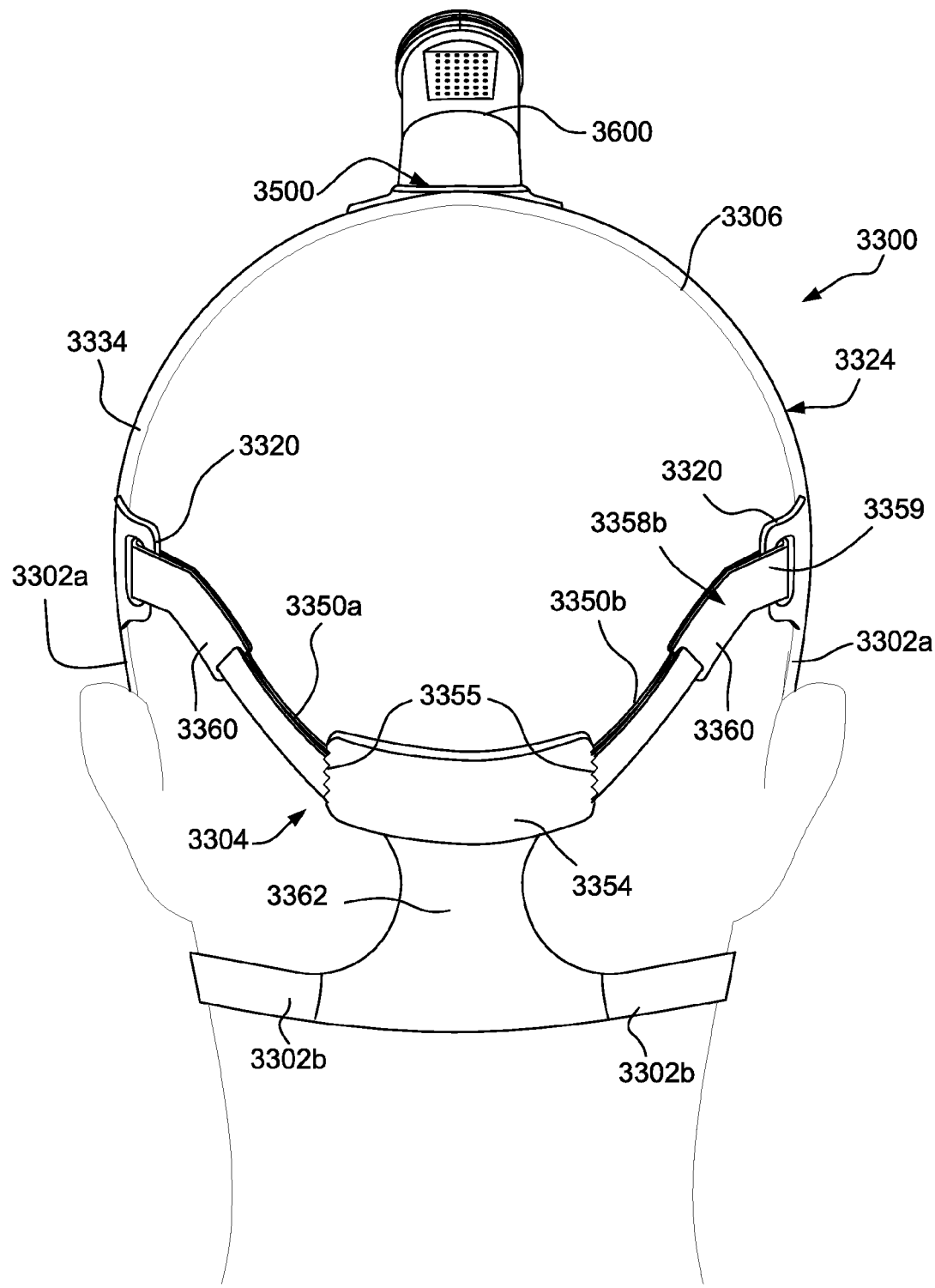

FIG. 58 shows a rear view of the under the nose mask and mouth seal of FIG. 52, illustrating the rear strap with a side portion constructed from a first material and a second section constructed from a second material. The extender is constructed from a third material that differs from the first material.

Figure 59:
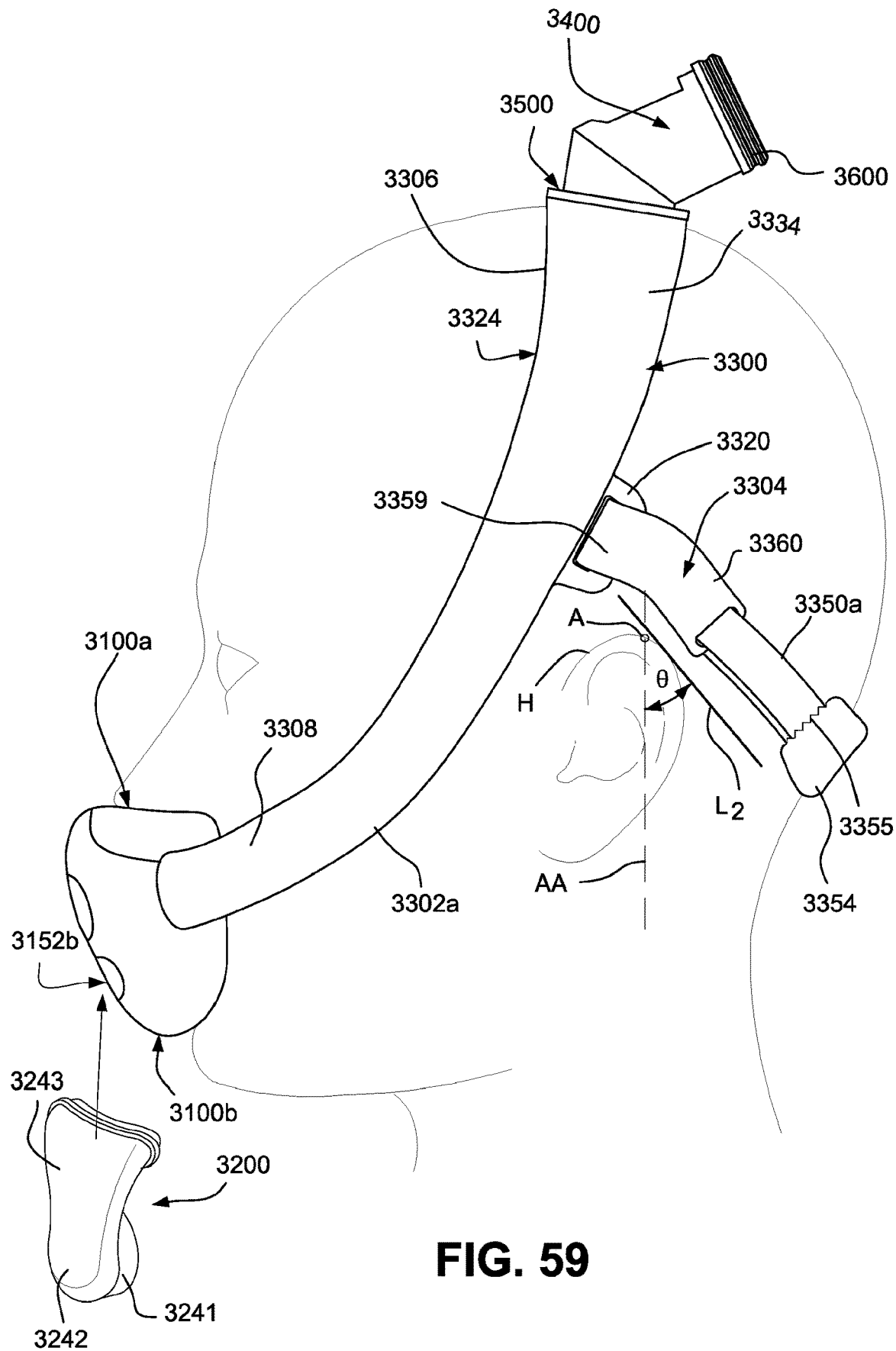

FIG. 59 shows a side view of the under the nose mask and mouth seal of FIG. 52, with a rear strap made from two materials positioned around the patient's head. An extender is used to couple the rear strap to a hollow tube. The additional side strap of FIG. 57 is not used to maintain the under the nose mask and mouth seal in a therapeutically effective position.

Figure 60:
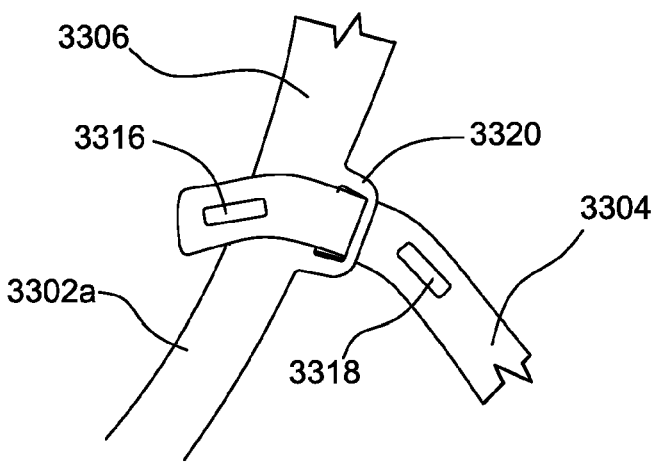

FIG. 60 shows a detail schematic view of the positioning and stabilizing structure of FIG. 53, illustrating the rear strap removably coupled to the loop using a fastening mechanism.

Figure 61:
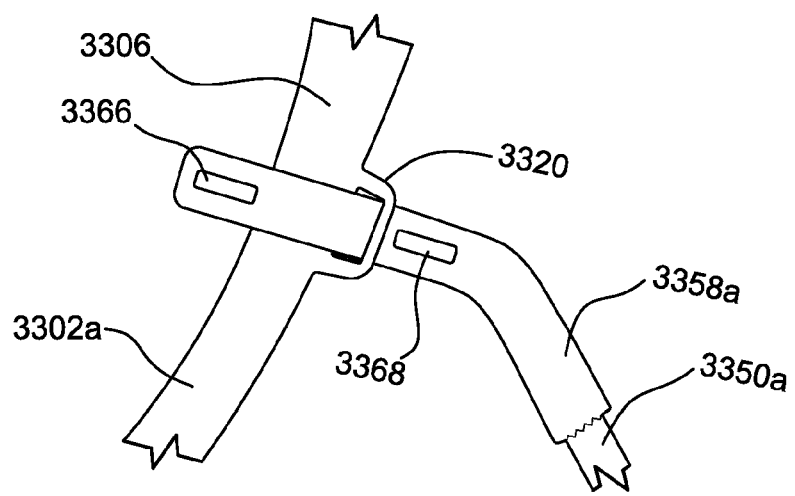

FIG. 61 shows a detail schematic view of the positioning and stabilizing structure of FIG. 55, illustrating the extender removably coupled to the loop using a fastening mechanism.

Figure 62:
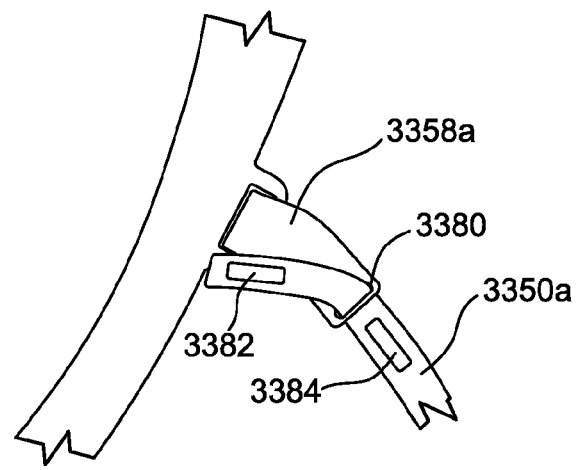

FIG. 62 shows a detail schematic view of the positioning and stabilizing structure of FIG. 55, illustrating the rear strap removably coupled to the extender using a fastening mechanism.

Figure 63:
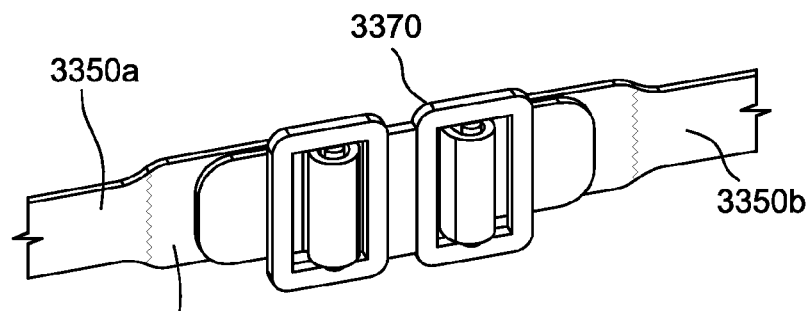

FIG. 63 shows a detail schematic view of the pad of the positioning and stabilizing structure of FIG. 54, illustrating a first adjustment mechanism.

Figure 64:
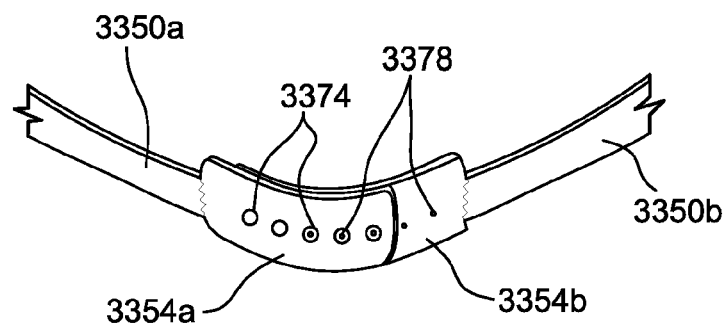

FIG. 64 shows a detail schematic view of the pad of the positioning and stabilizing structure of FIG. 54, illustrating a second adjustment mechanism.

Figure 65:
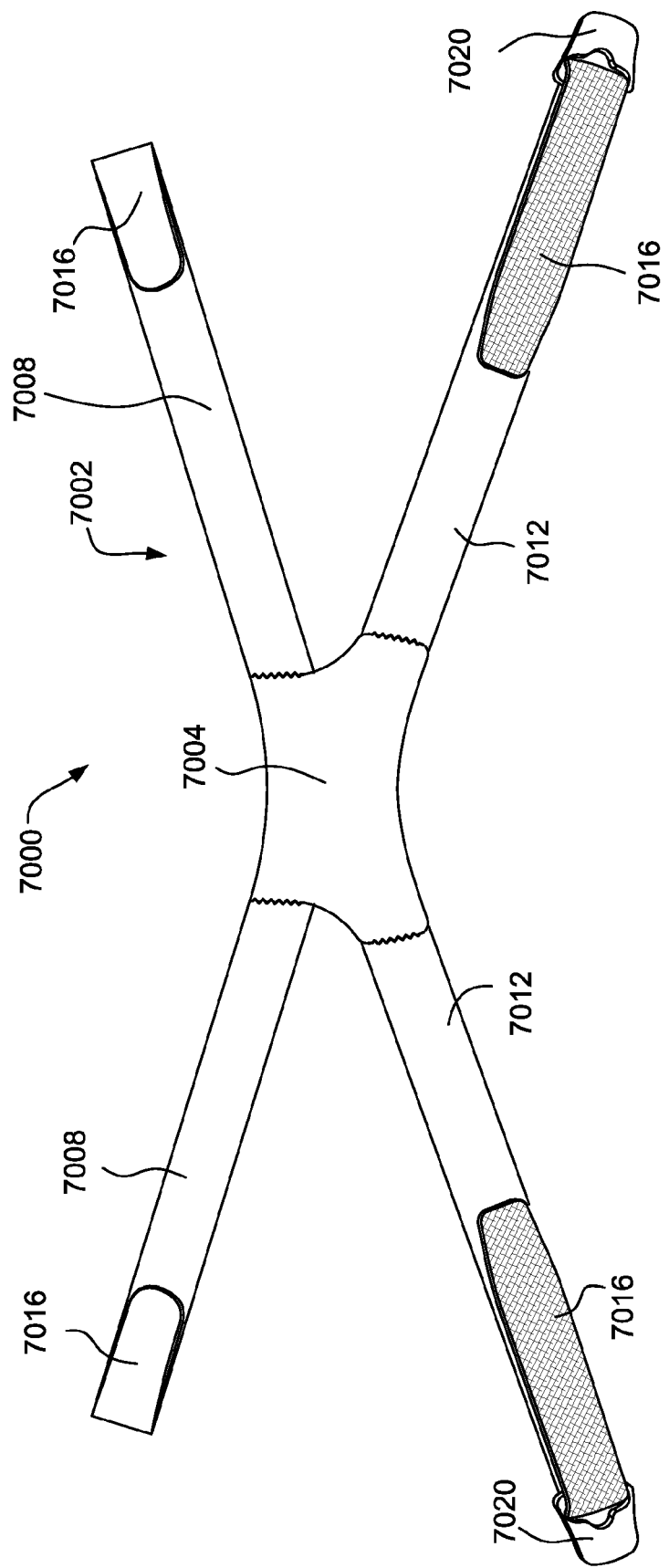
Figures 1, 65:
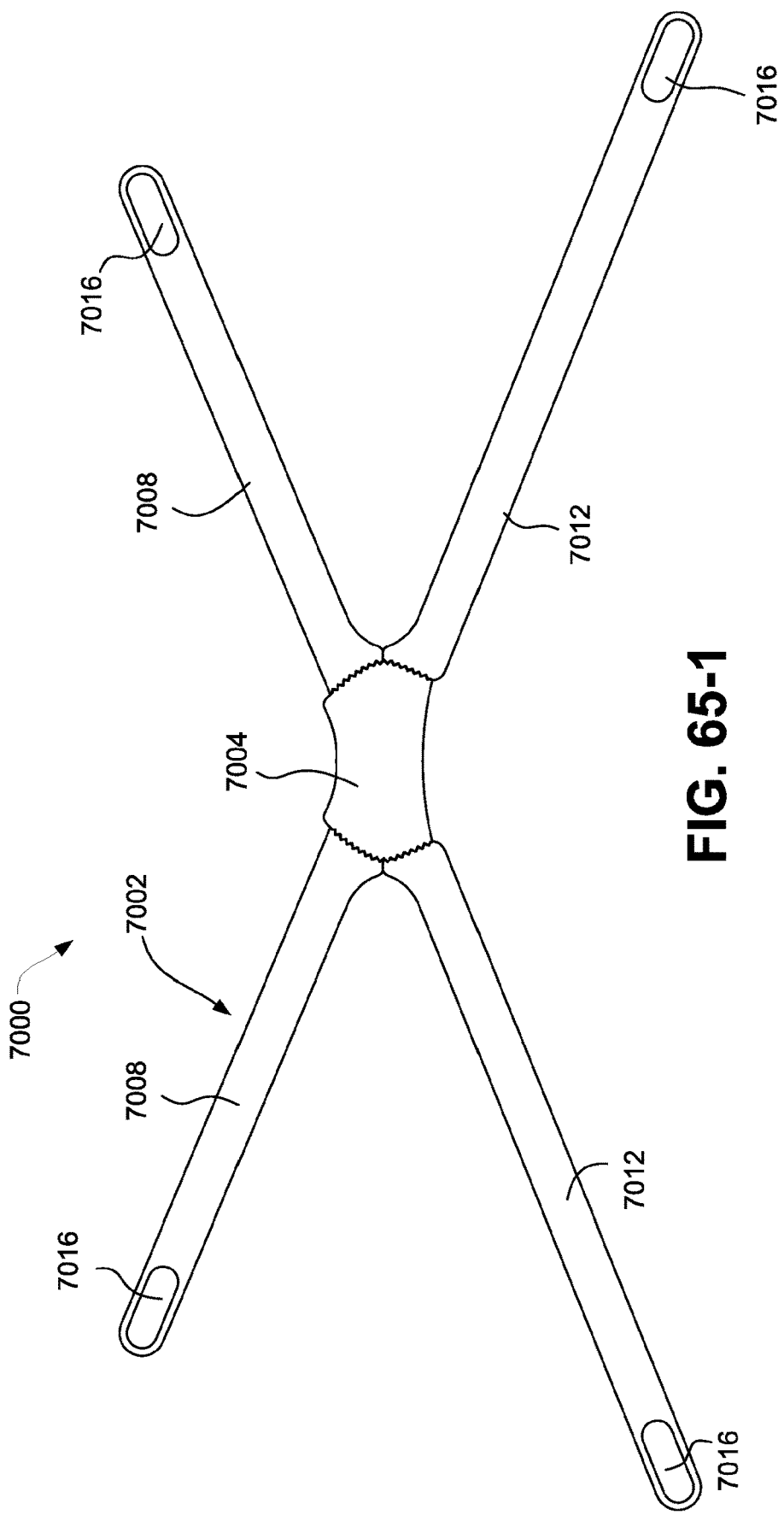

FIG. 65 shows a rear view of headgear straps for use in a positioning and stabilizing structure, illustrating each strap individually stitched to the rear portion.

Figure 1:
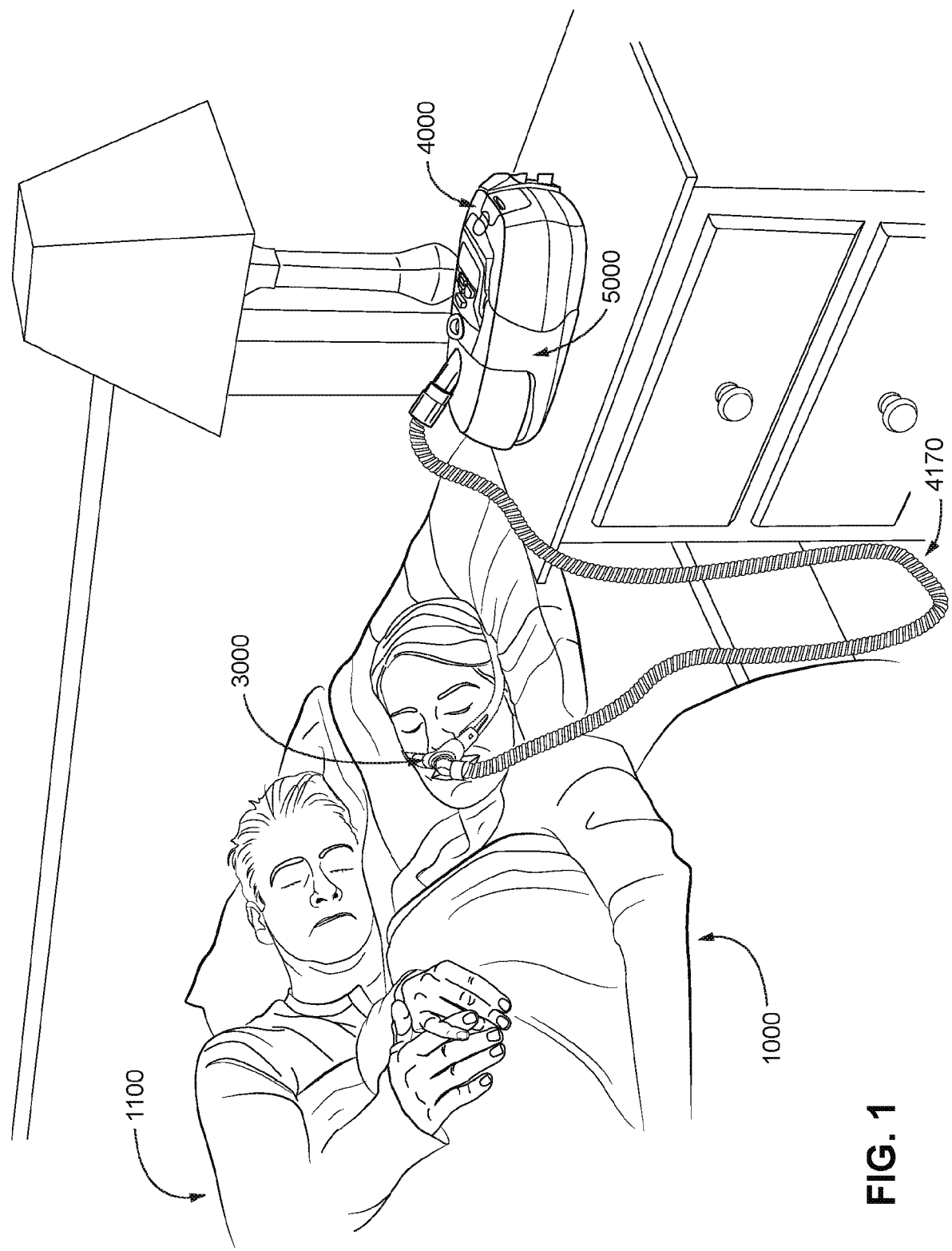
Figure 2:
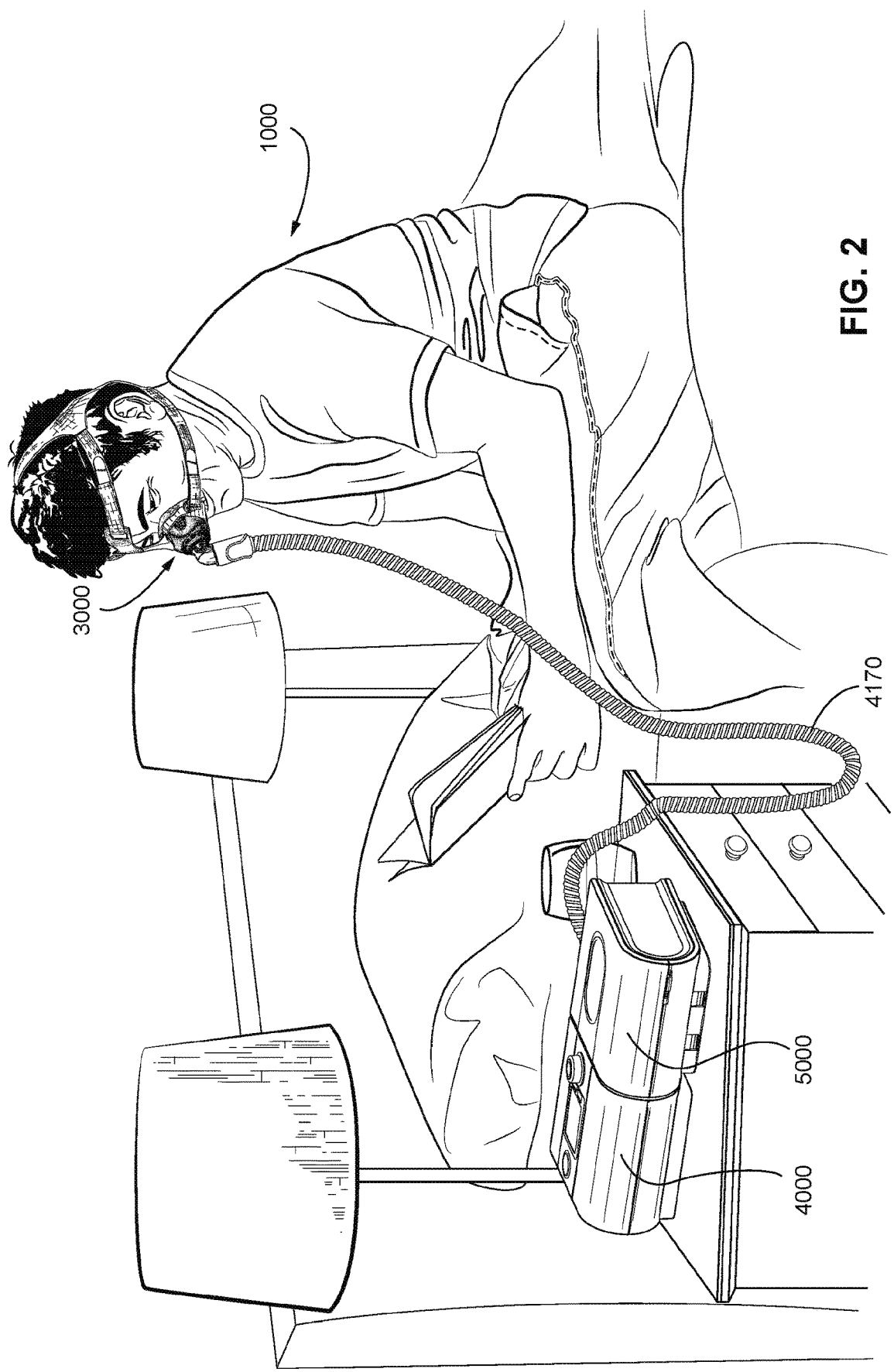
Figure 3:
Figure 4:
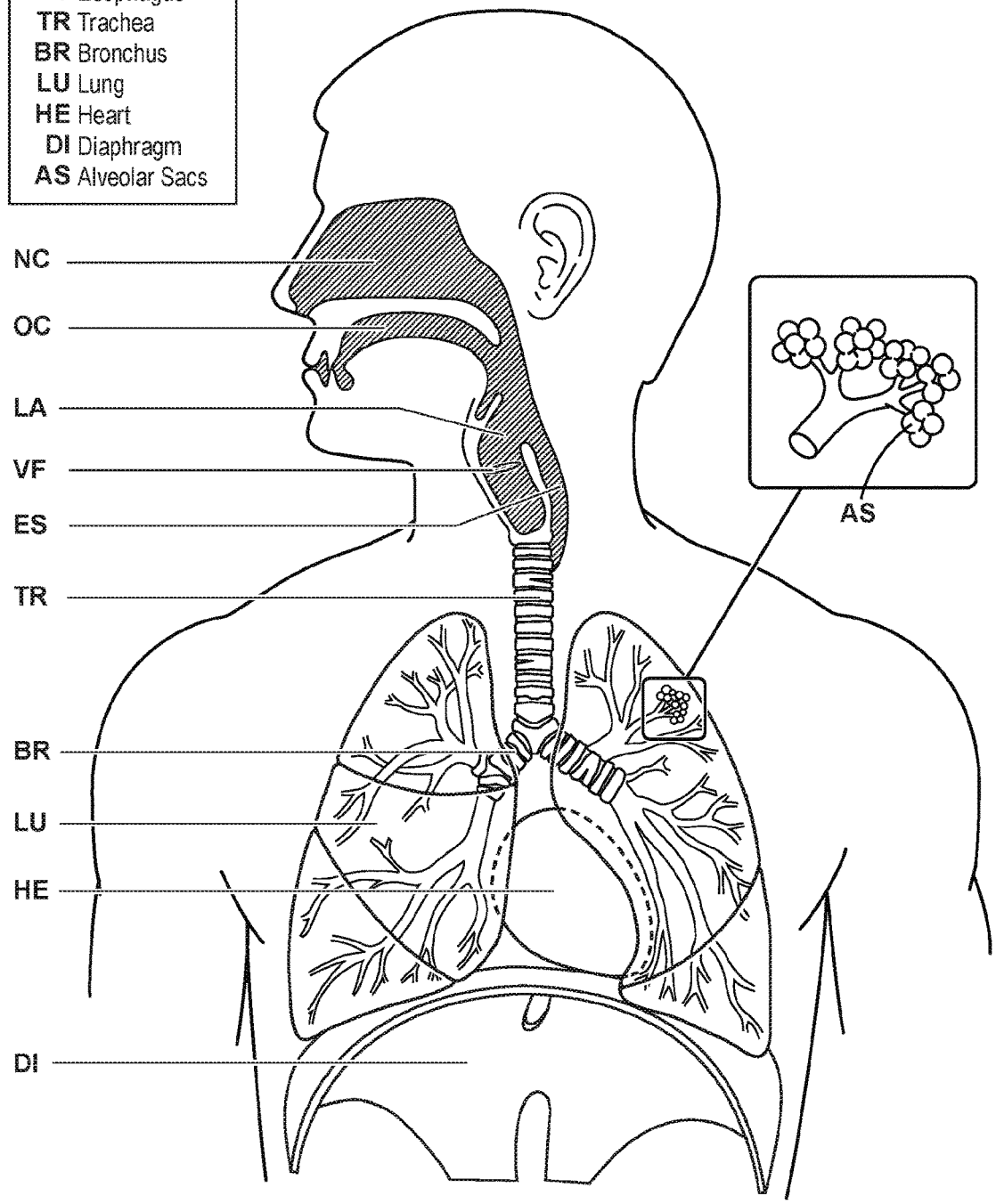
FIG. 4 shows an overview of a human respiratory system including the nasal and oral cavities, the larynx, vocal folds, oesophagus, trachea, bronchus, lung, alveolar sacs, heart and diaphragm.
Figure 5:
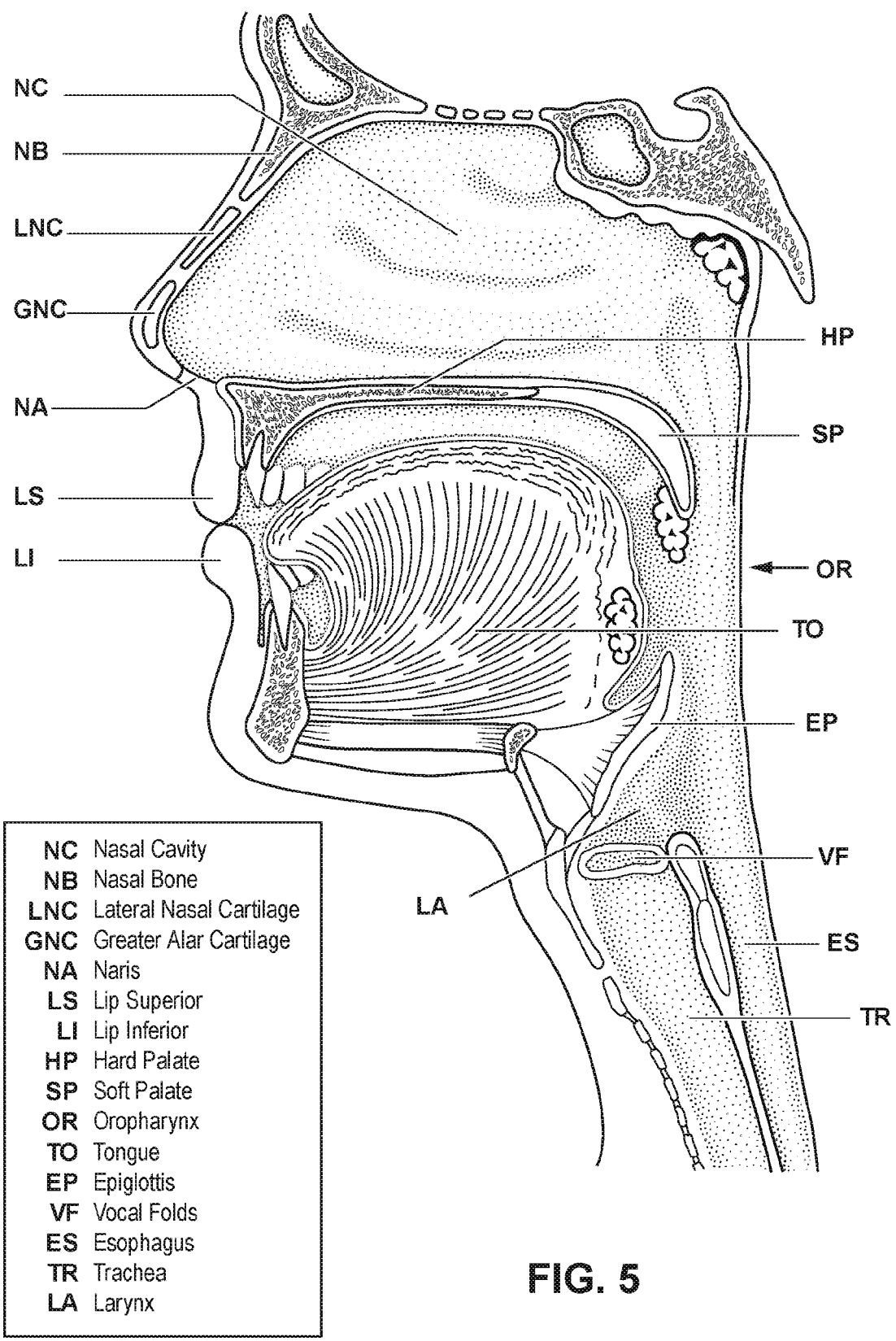
FIG. 5 shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

FIG. 65-1 shows a rear view of an alternate version of headgear straps of FIG. 65, illustrating curved stitching connecting the straps to the rear portion.

Figure 66:
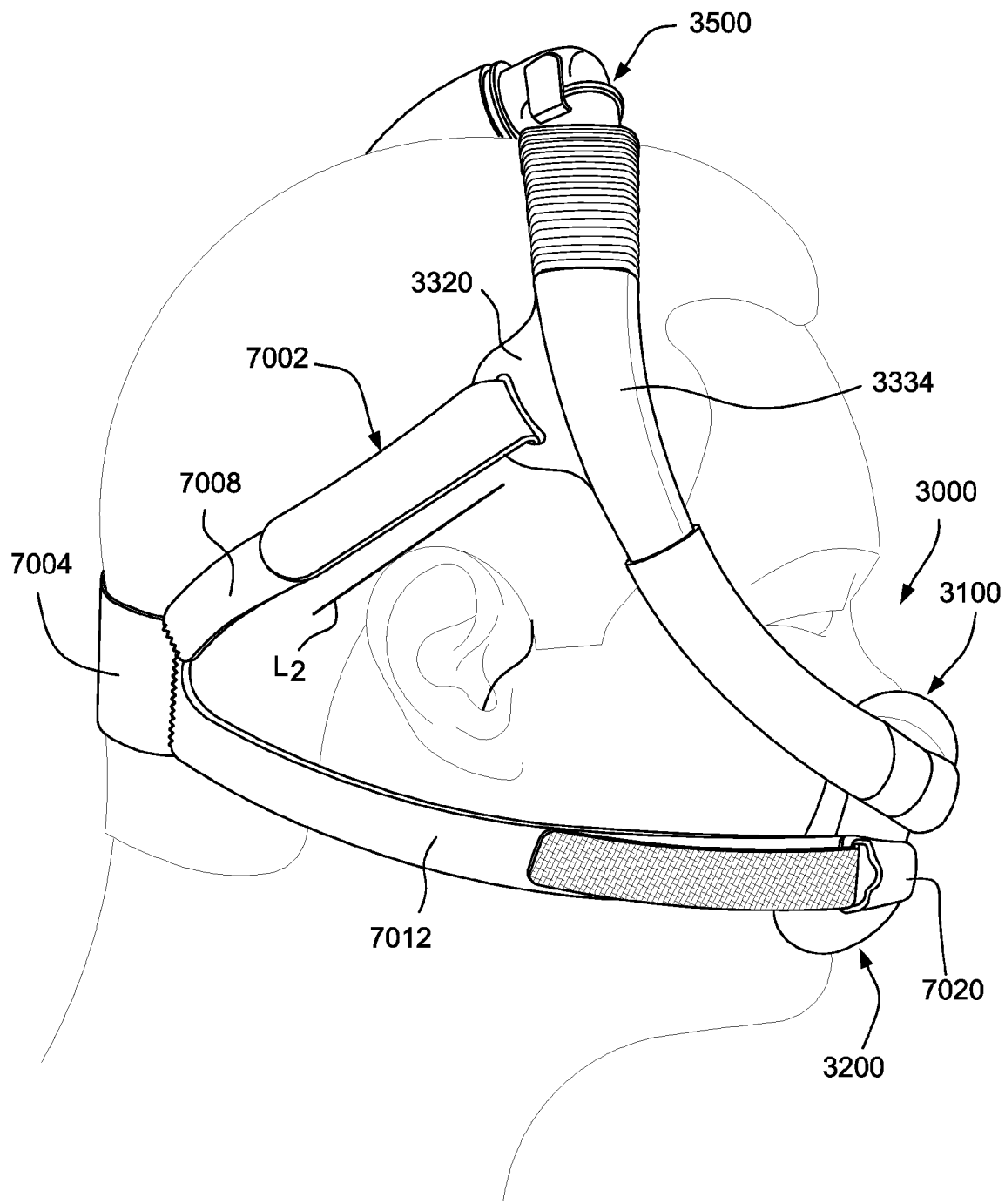

FIG. 66 shows a side view of a patient wearing a patient interface including the headgear of FIG. 65, illustrating a strap of the headgear connection proximate a superior portion of the patient's head.

Figure 67:
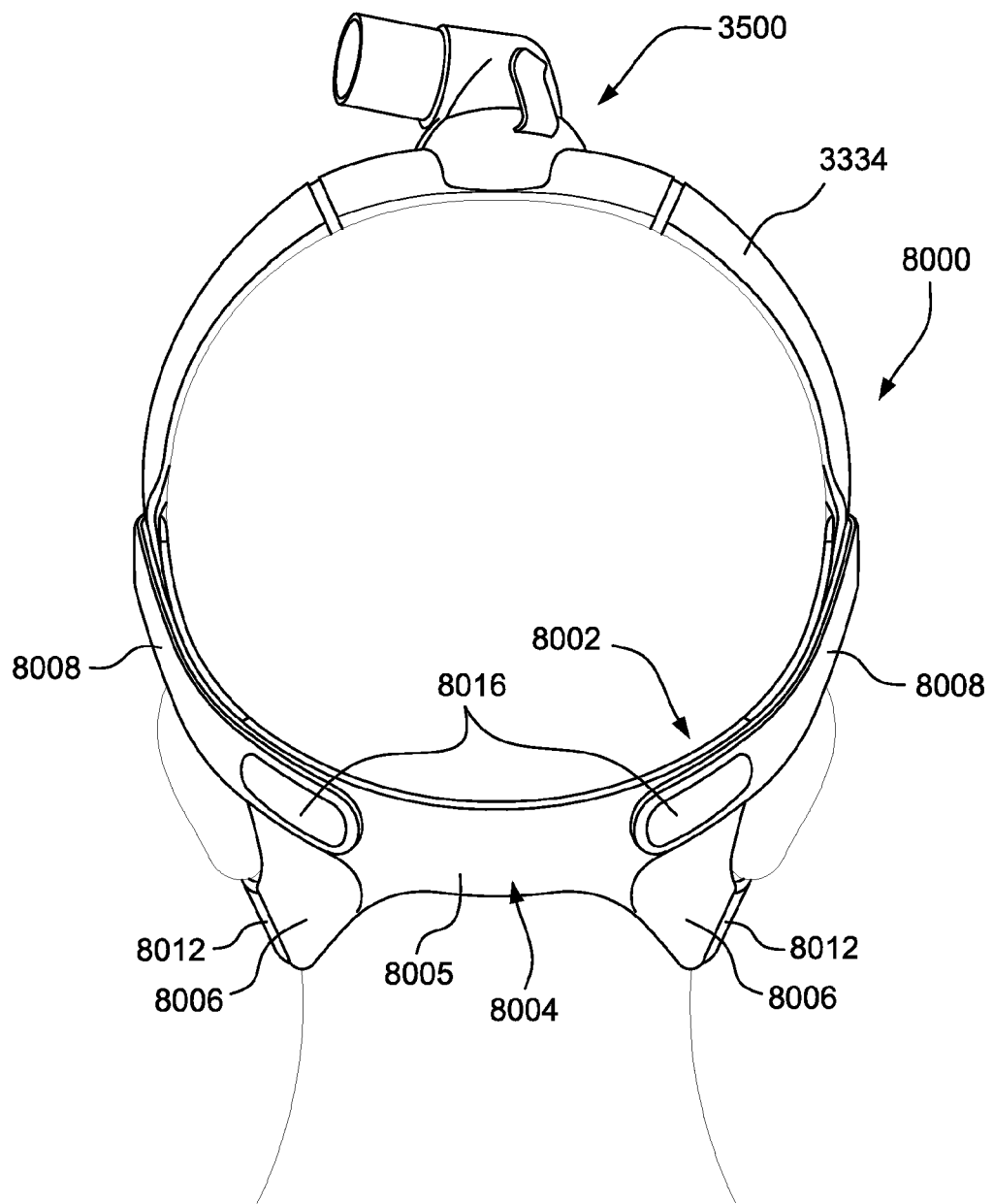

FIG. 67 illustrates a rear view of a patient wearing a patient interface including another example of headgear.

Figure 68:
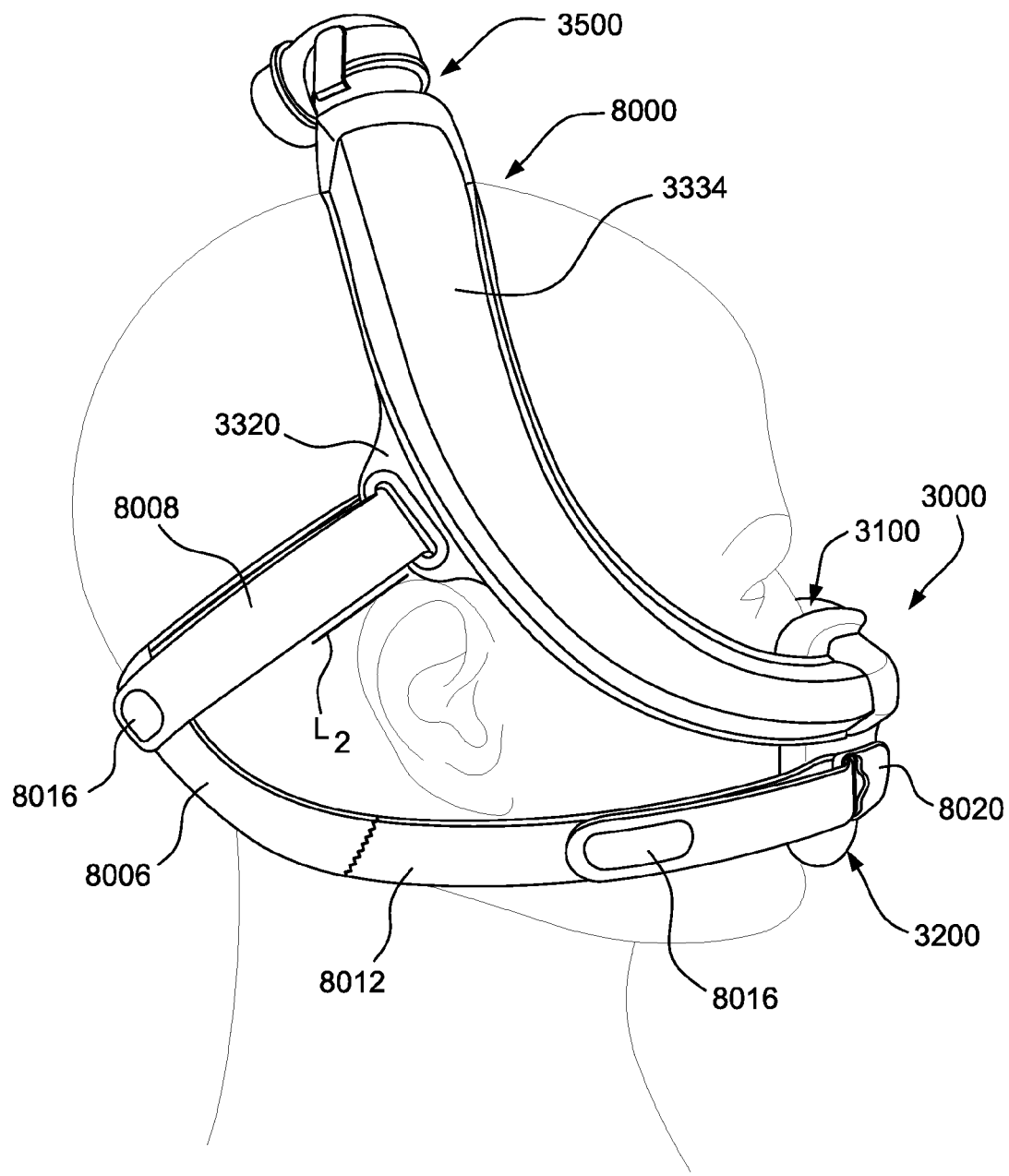

FIG. 68 is a side view of the patient wearing the patient interface of FIG. 67.

Figure 69:
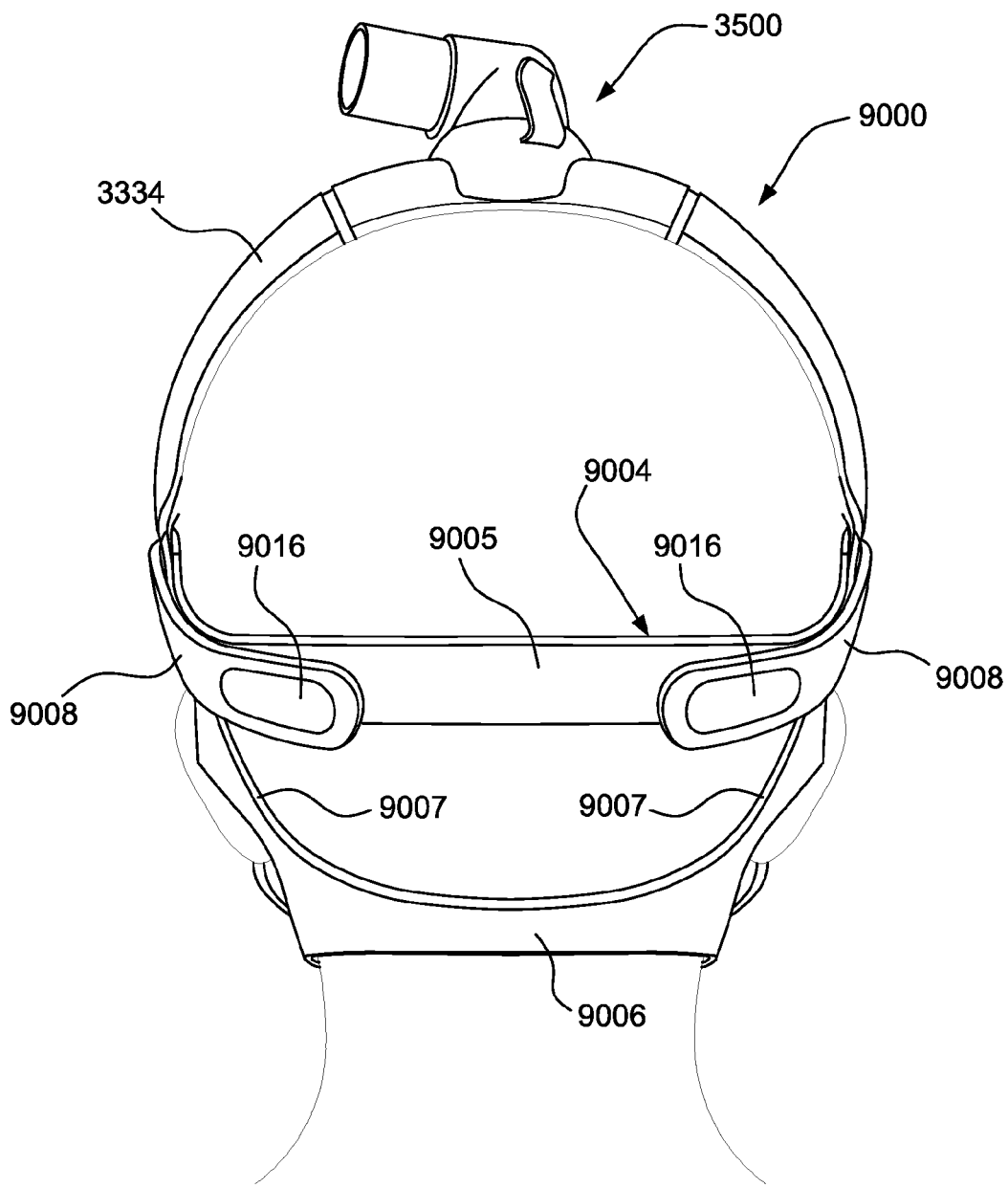

FIG. 69 is a rear view of a patient wearing a patient interface including another example of headgear.

Figure 70:
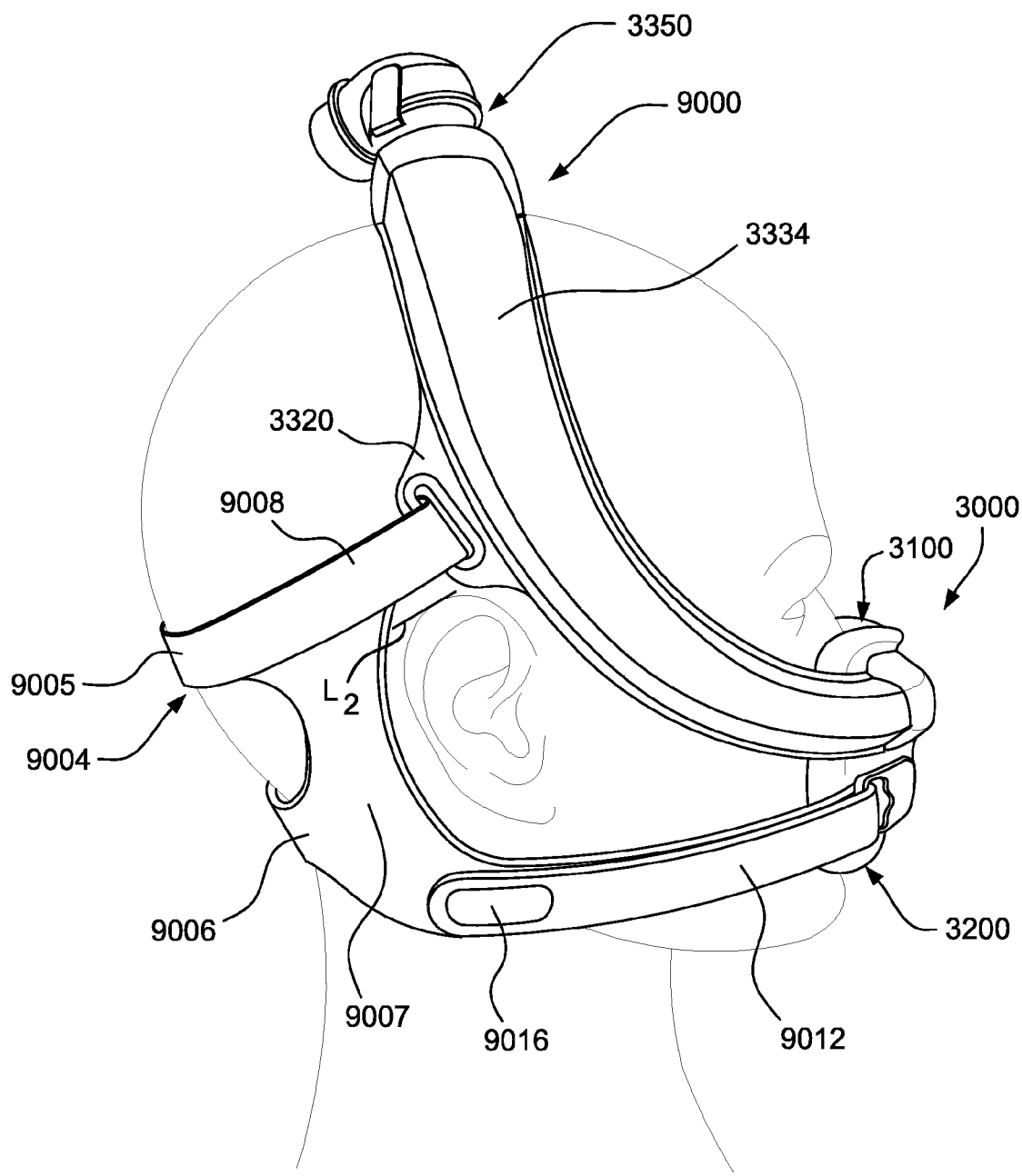

FIG. 70 is a side view of the patient wearing the patient interface of FIG. 69.

Figure 71:
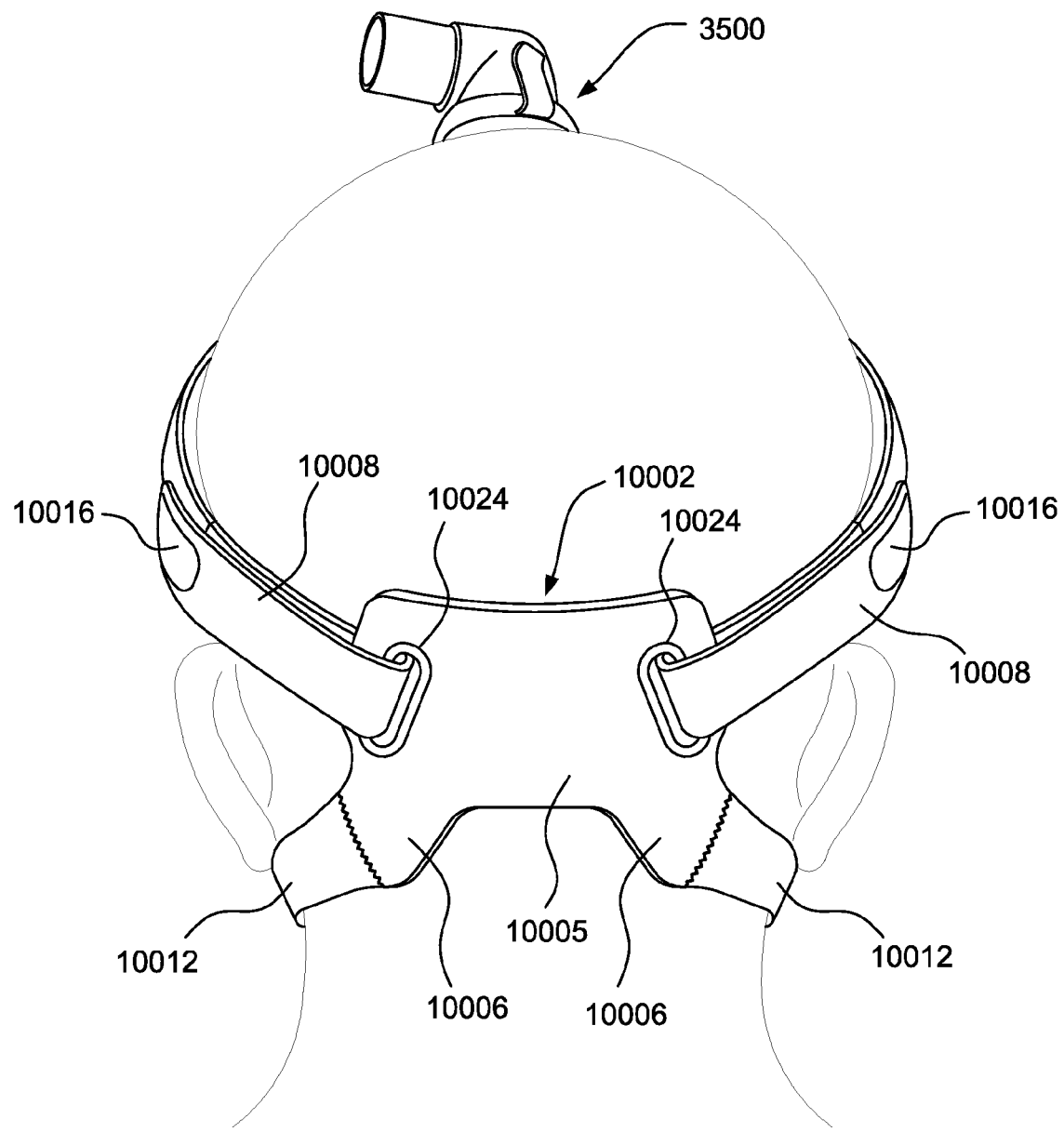

FIG. 71 is a rear view of a patient wearing a patient interface including another example of headgear.

Figure 72:
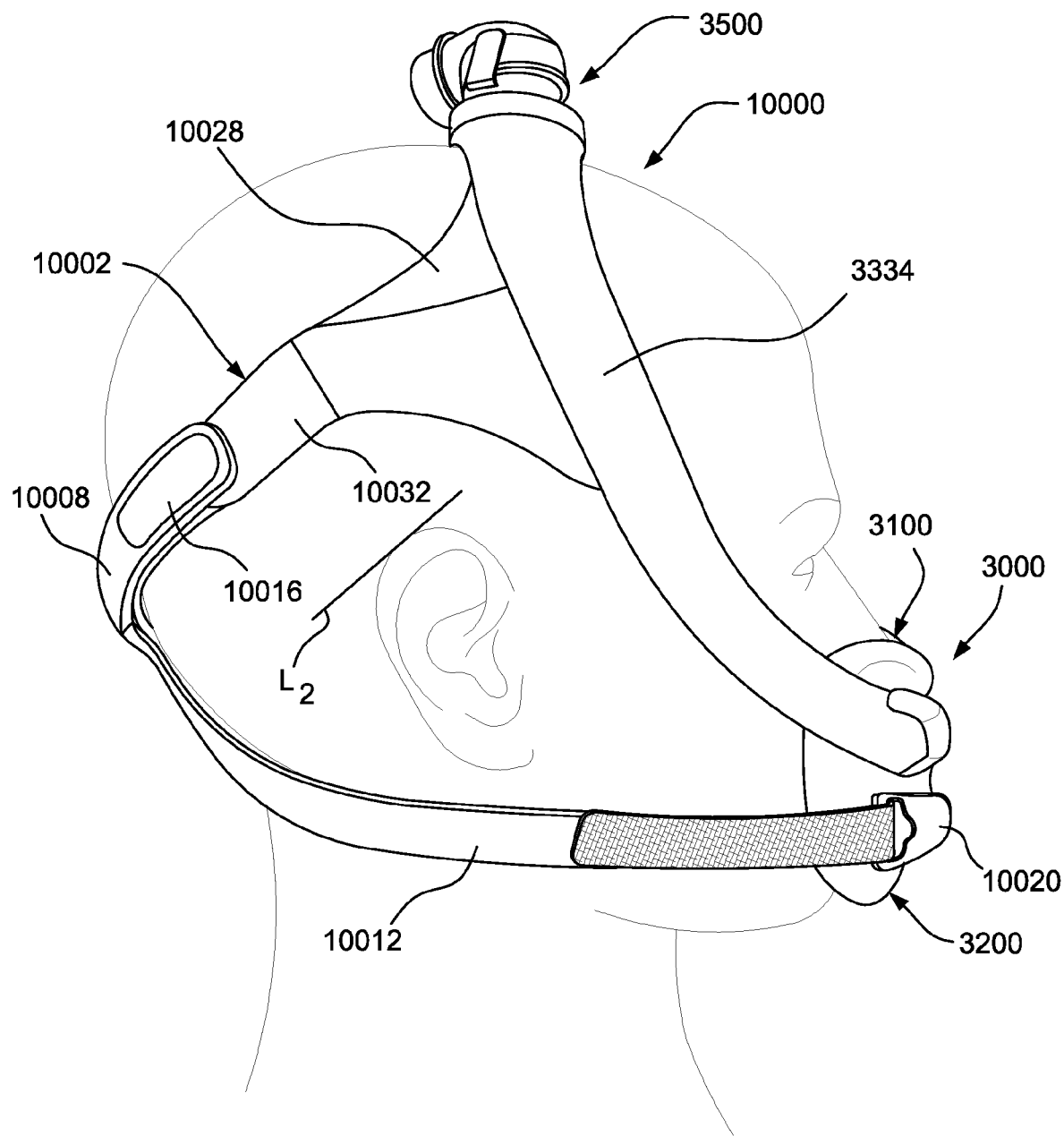

FIG. 72 is a side view of the patient wearing the patient interface of FIG. 71.

Figure 73:
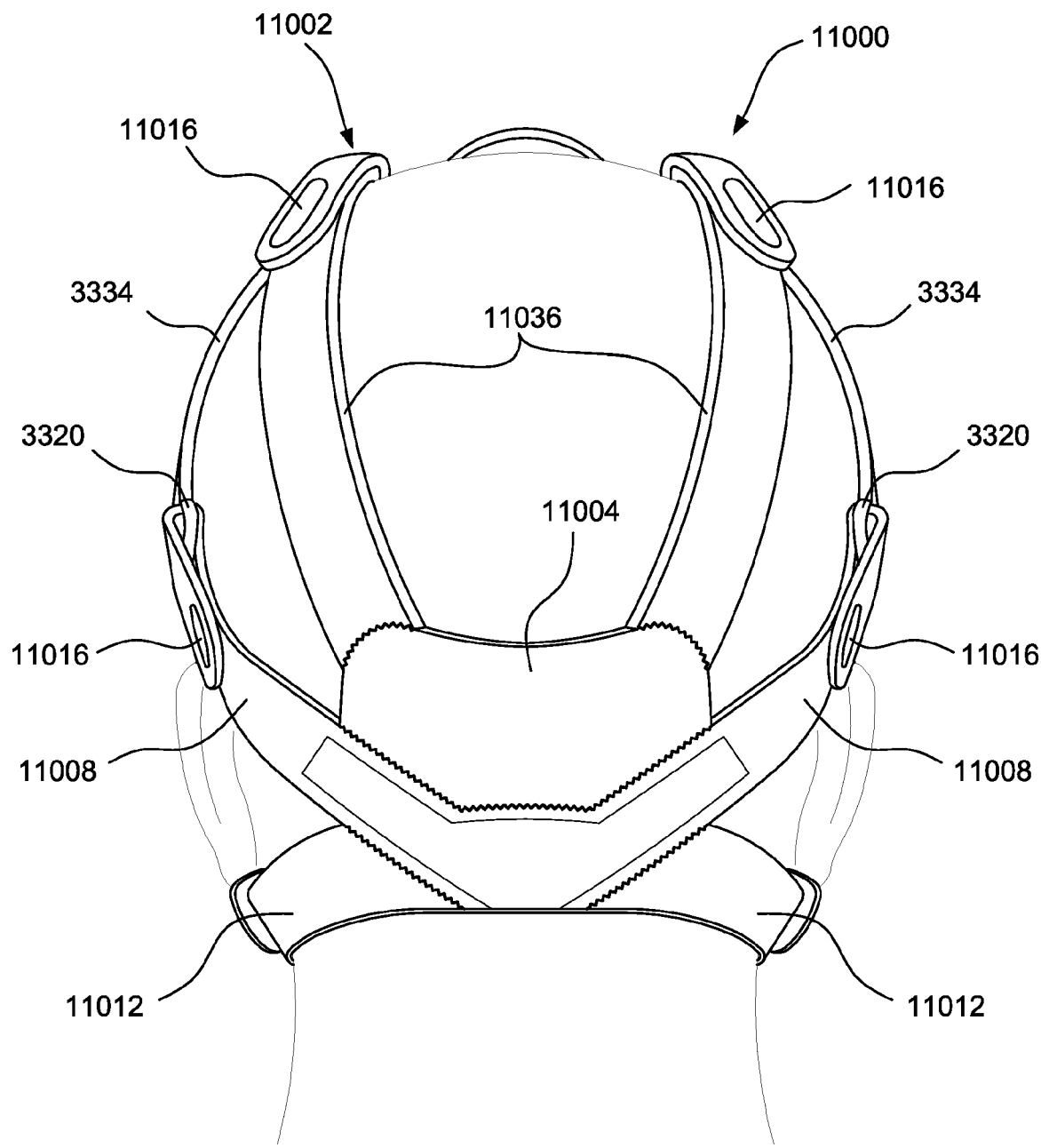

FIG. 73 is a rear view of a patient wearing a patient interface including another example of headgear.

Figure 74:
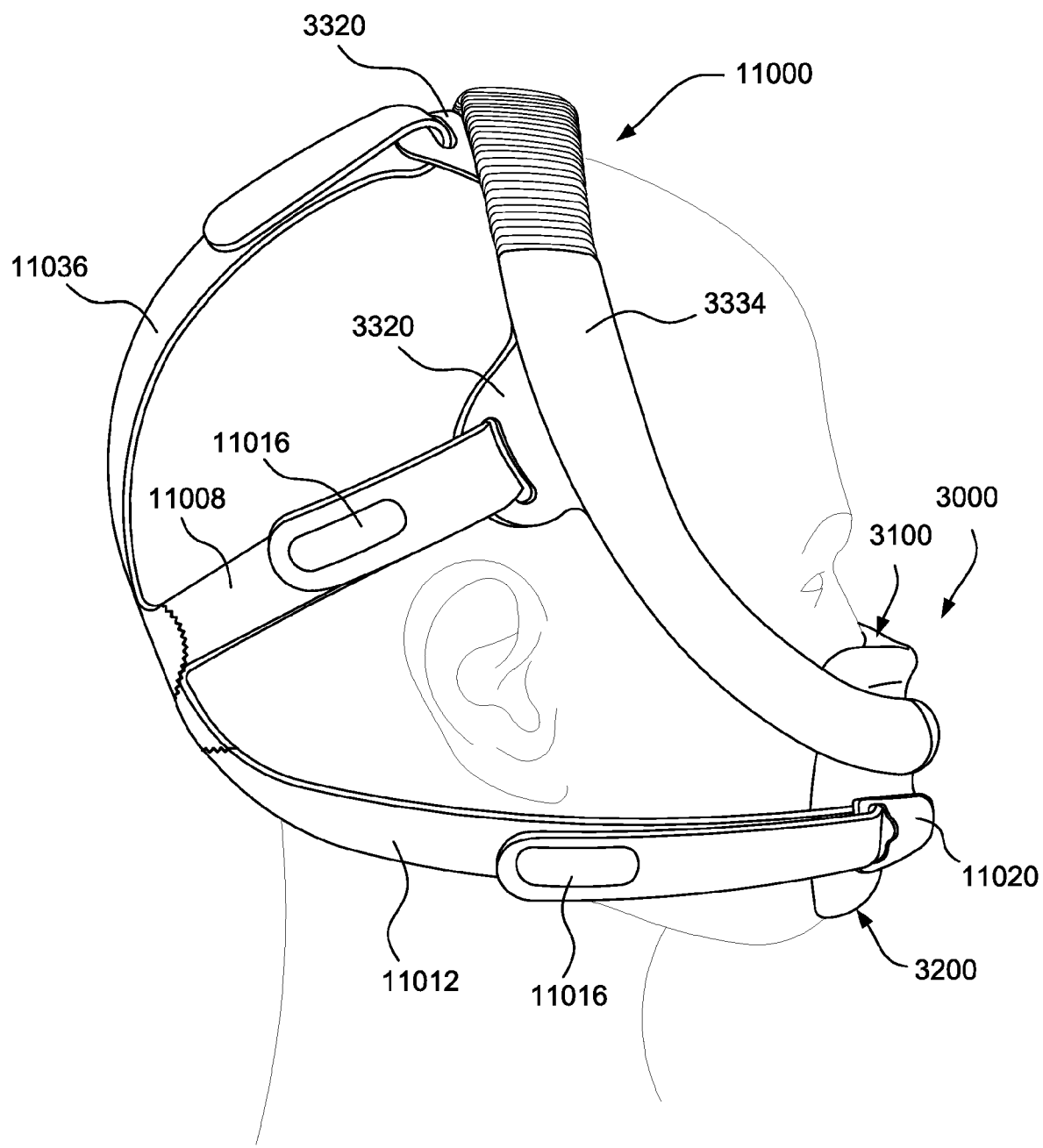

FIG. 74 is a side view of the patient wearing the patient interface of FIG. 73.

Figure 75:
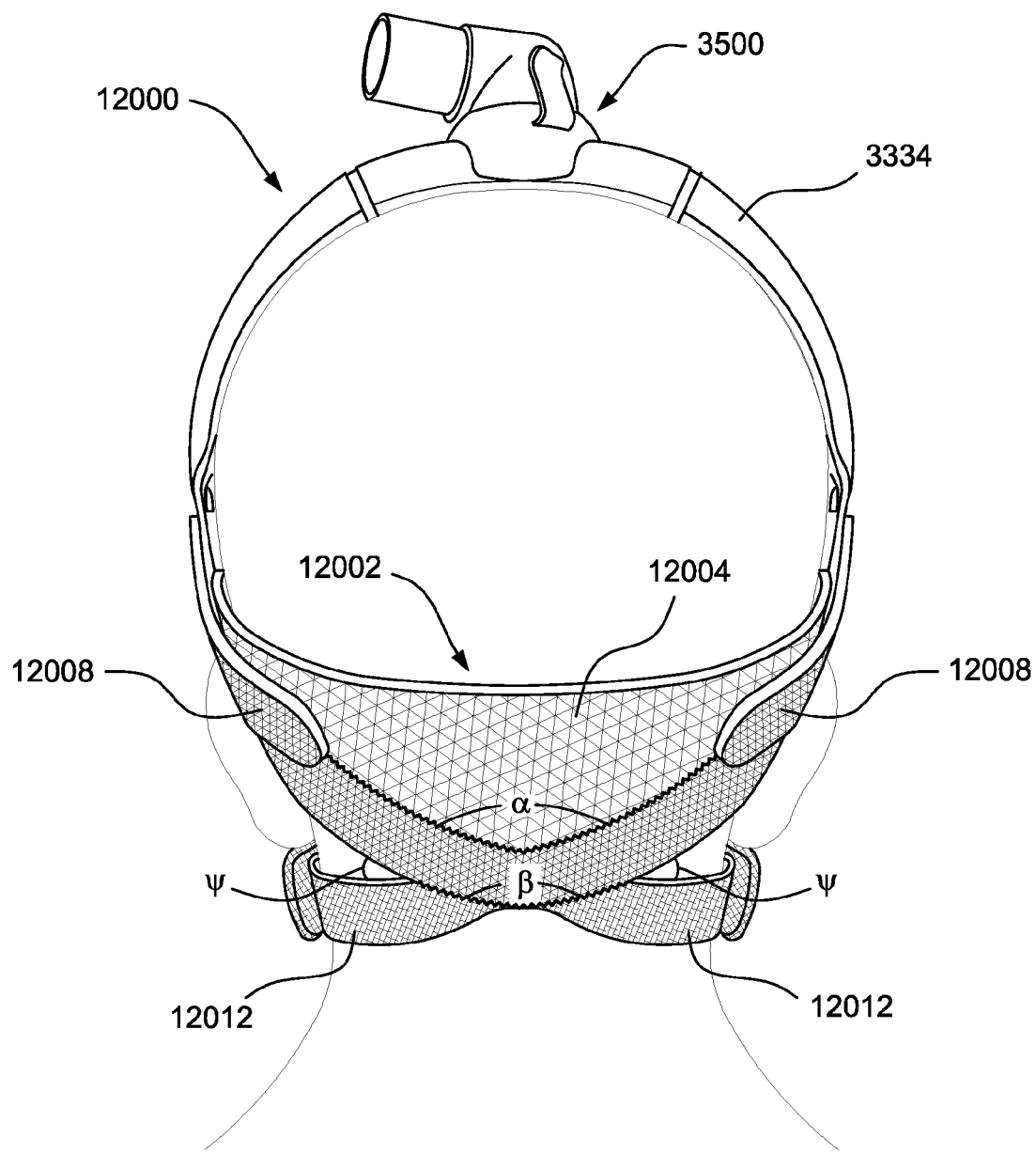
Figures 1, 75:
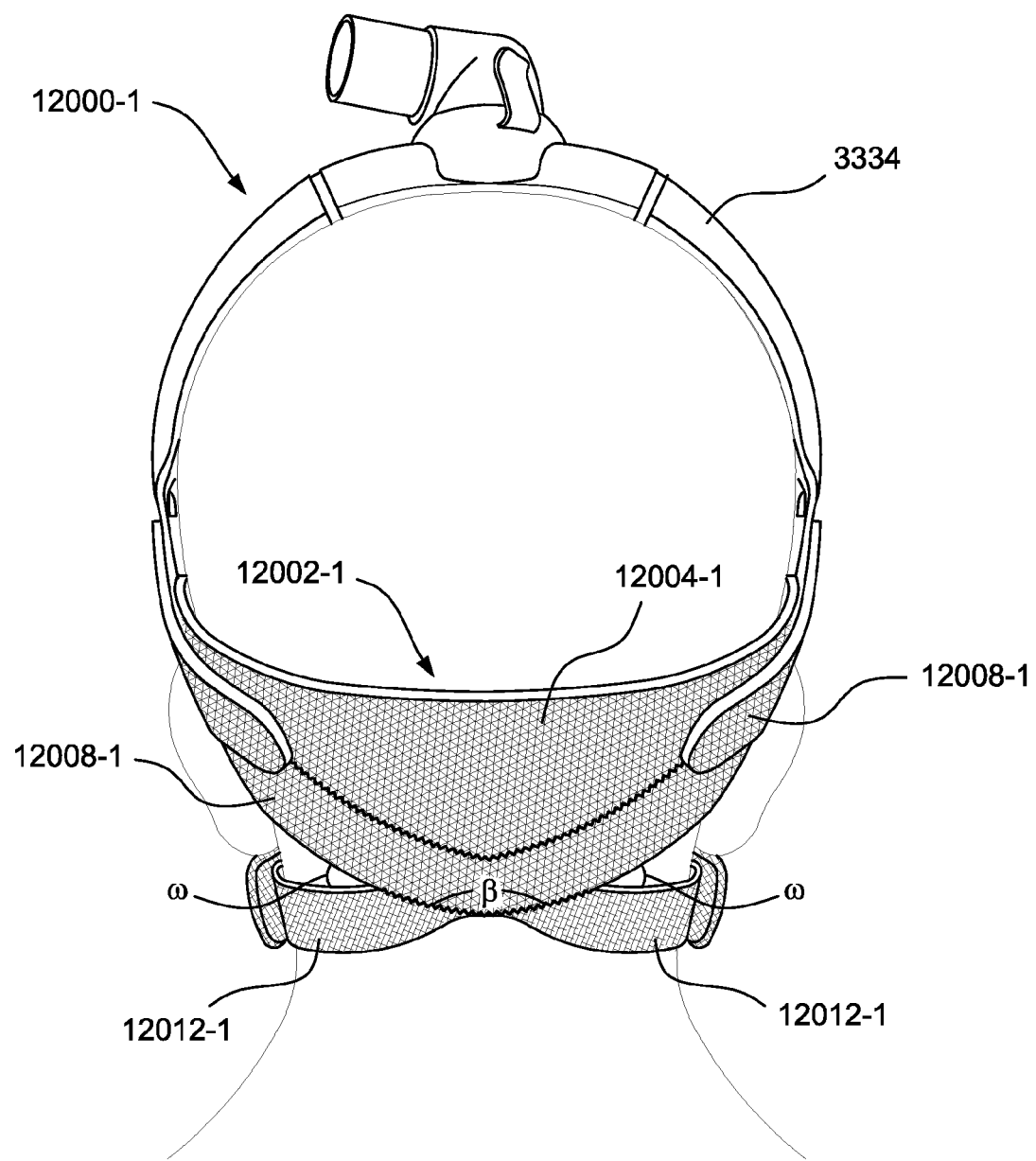

FIG. 75 is a rear view of a patient wearing a patient interface including another example of headgear.

FIG. 75-1 is a rear view of a patient wearing an alternate version of the headgear of FIG. 75.

Figure 76:
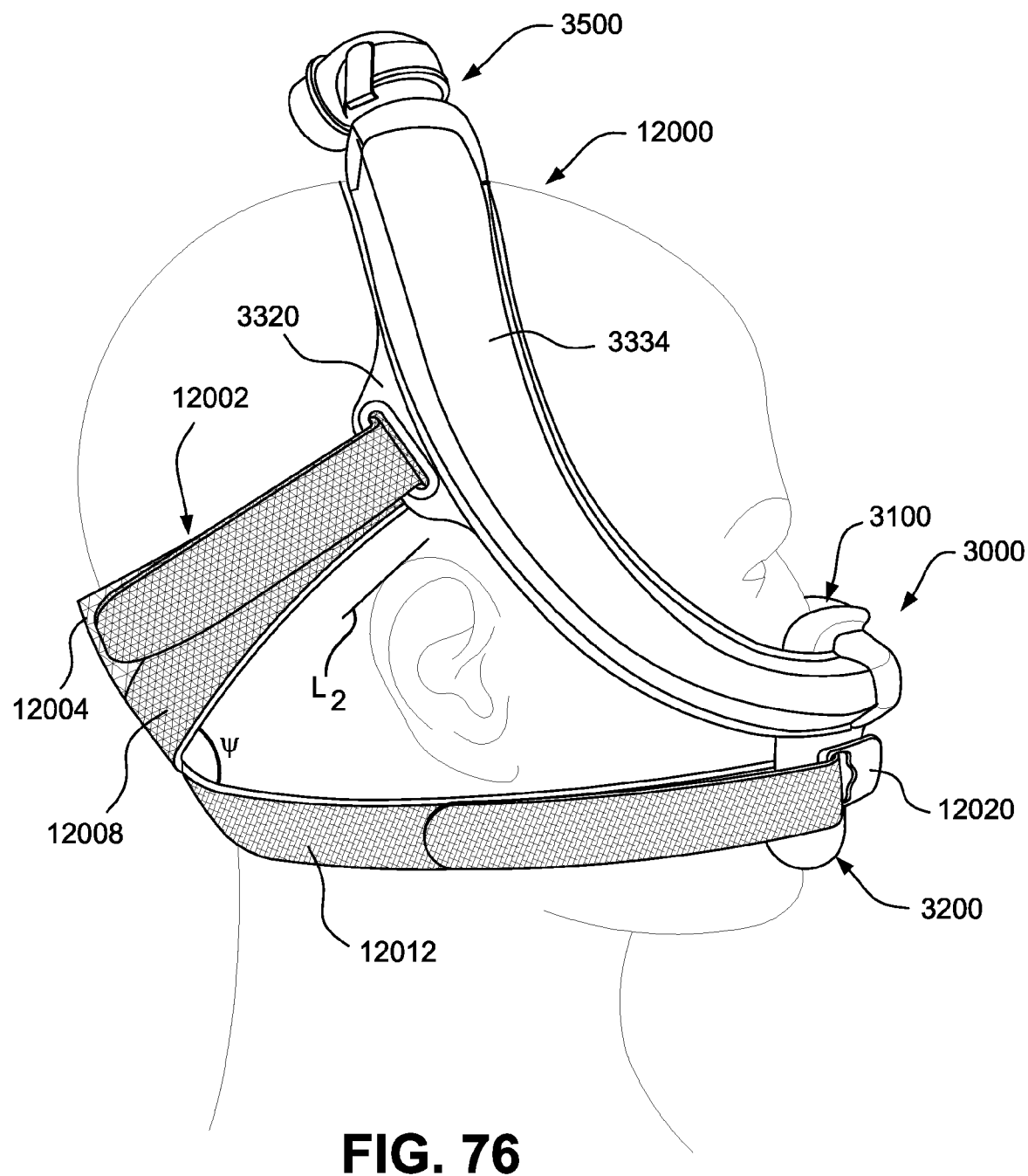

FIG. 76 is a side view of the patient wearing the patient interface of FIG. 75.

Figure 77:
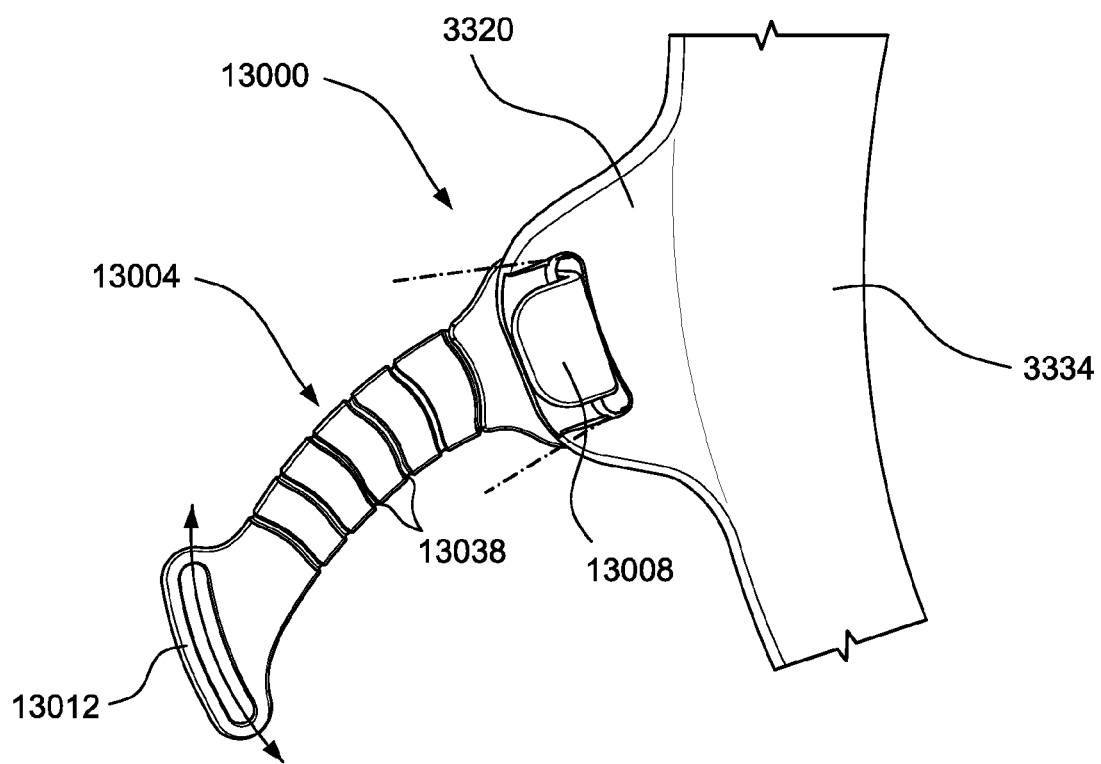

FIG. 77 is a detail view of removable arm connected to a hollow tube.

Figure 78:
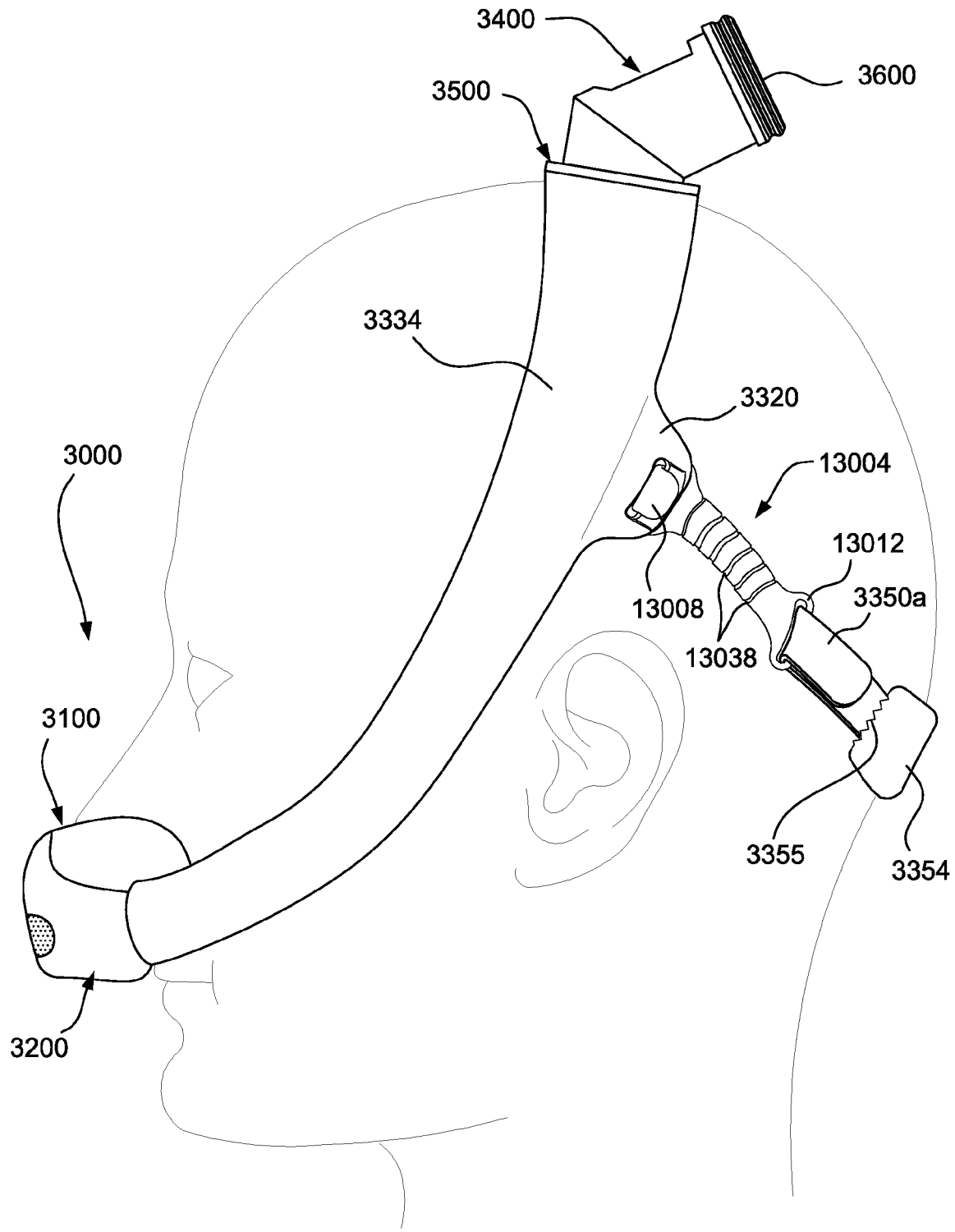

FIG. 78 is a perspective view of the removable arm of FIG. 77, used with a nasal cushion.

Figure 79:
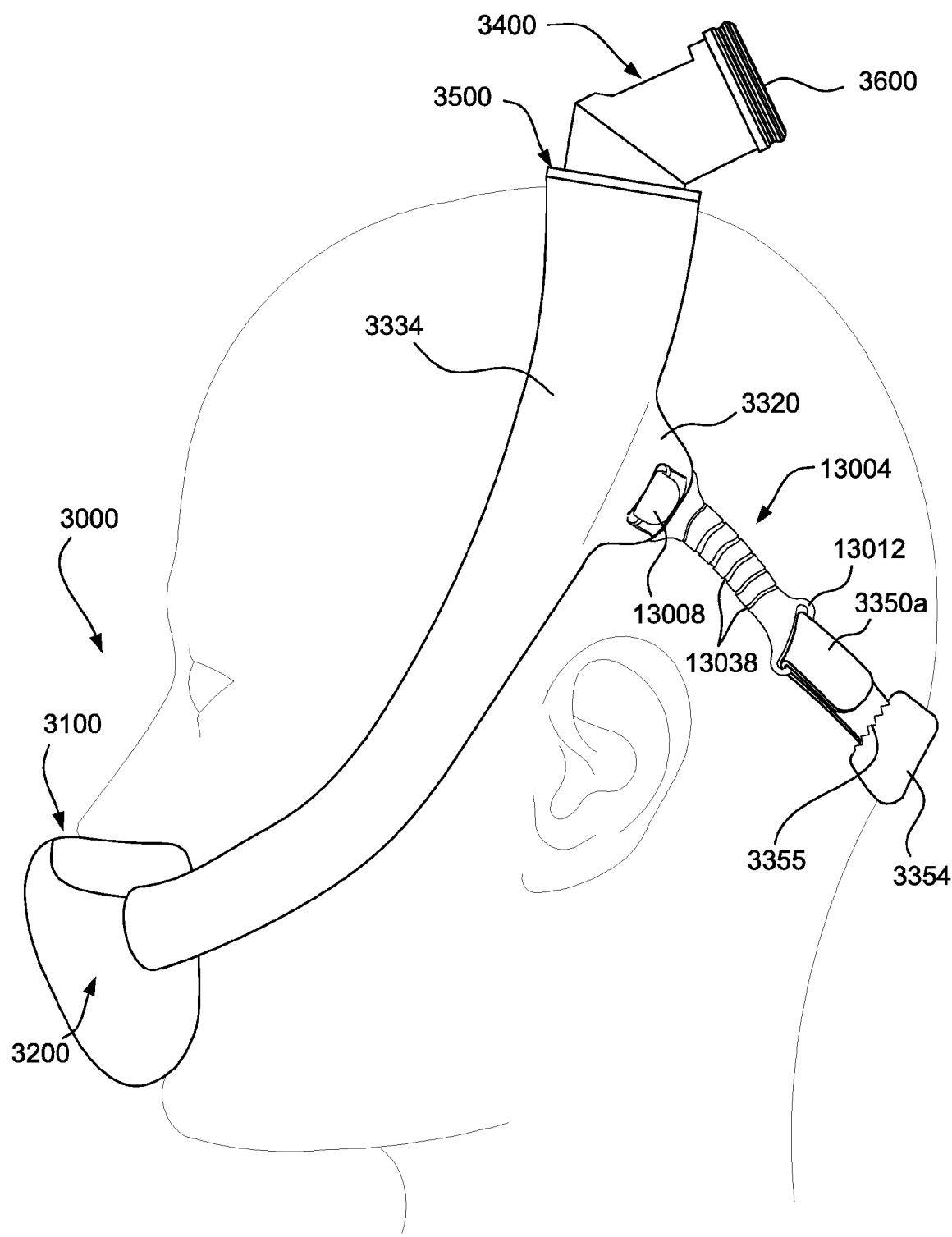

FIG. 79 is a perspective view of the removable arm of FIG. 77, used with a full-face cushion.

Figure 80:
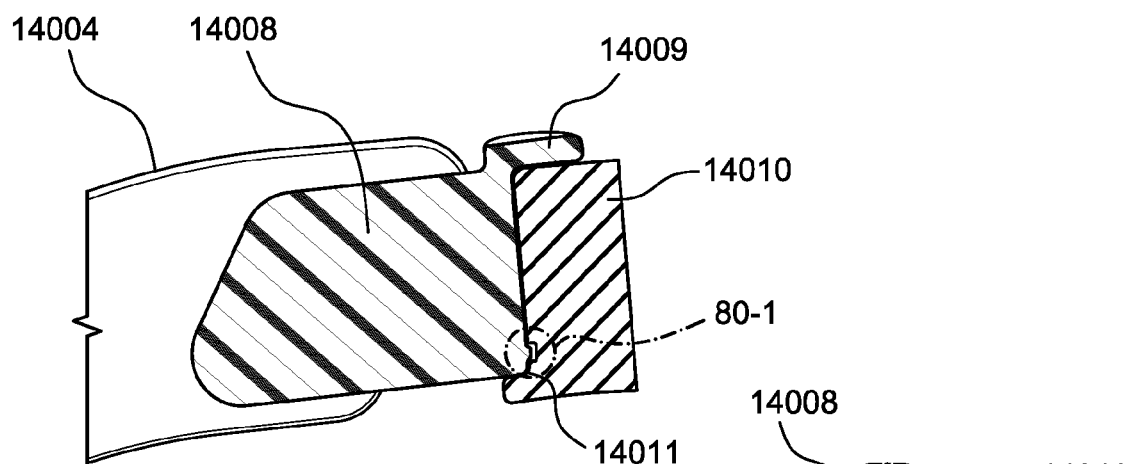
Figures 1, 80:
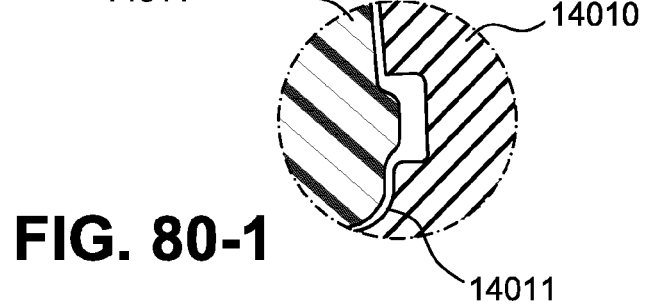

FIG. 80 is a detail view of an alternate form of the removable arm of FIG. 77.

FIG. 80-1 is a detail view of the removable arm of FIG. 80 illustrating a lock between a clip and a post of the arm.

Figure 81:
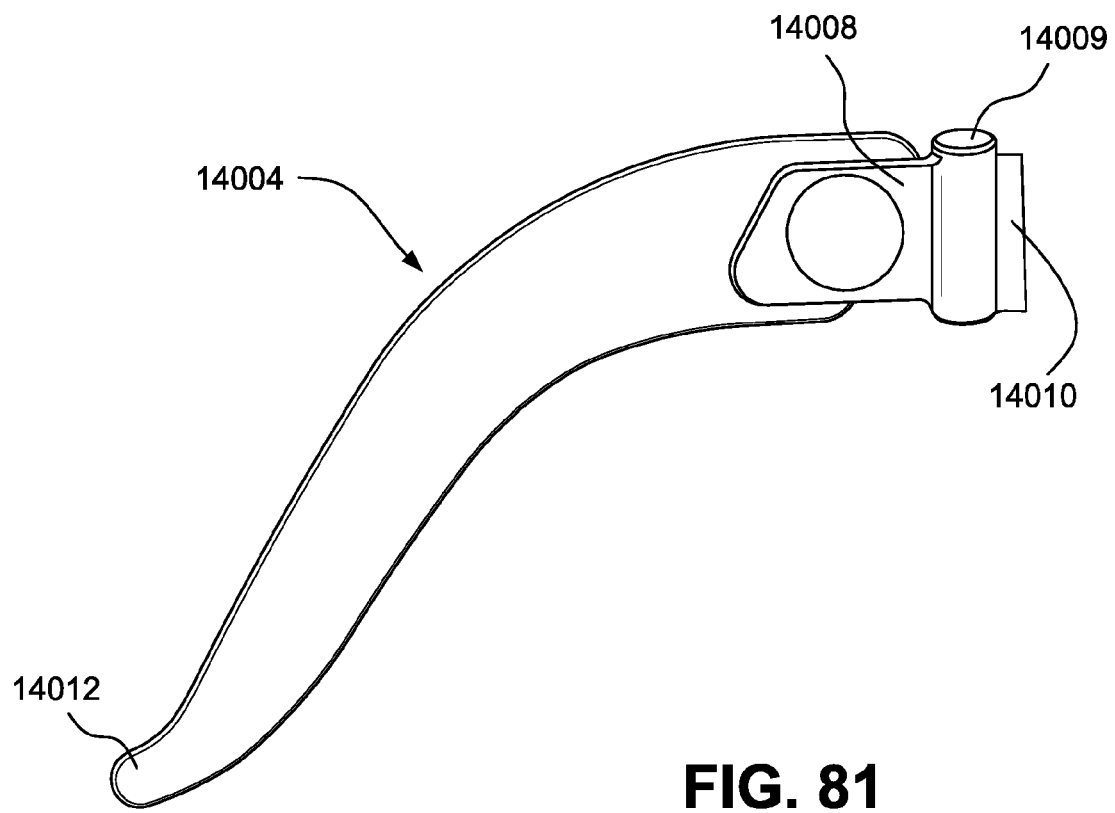

FIG. 81 is a perspective view of the removable arm of FIG. 80.

Figure 82:
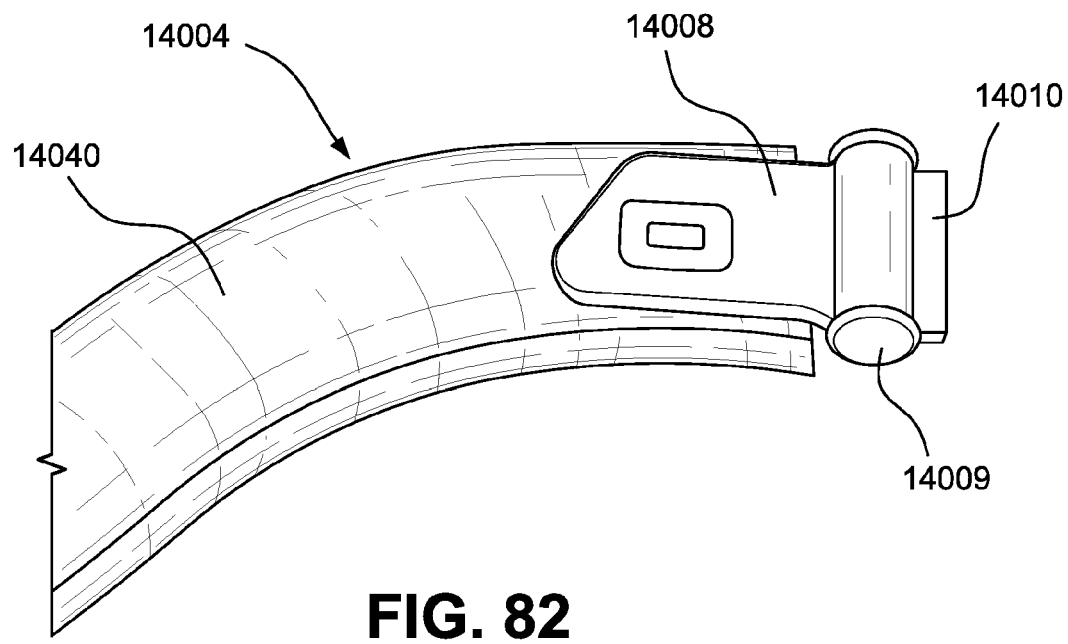

FIG. 82 is a detail view of the removable arm of FIG. 80, illustrating a textile sleeve coupled to the arm.

Figure 83:
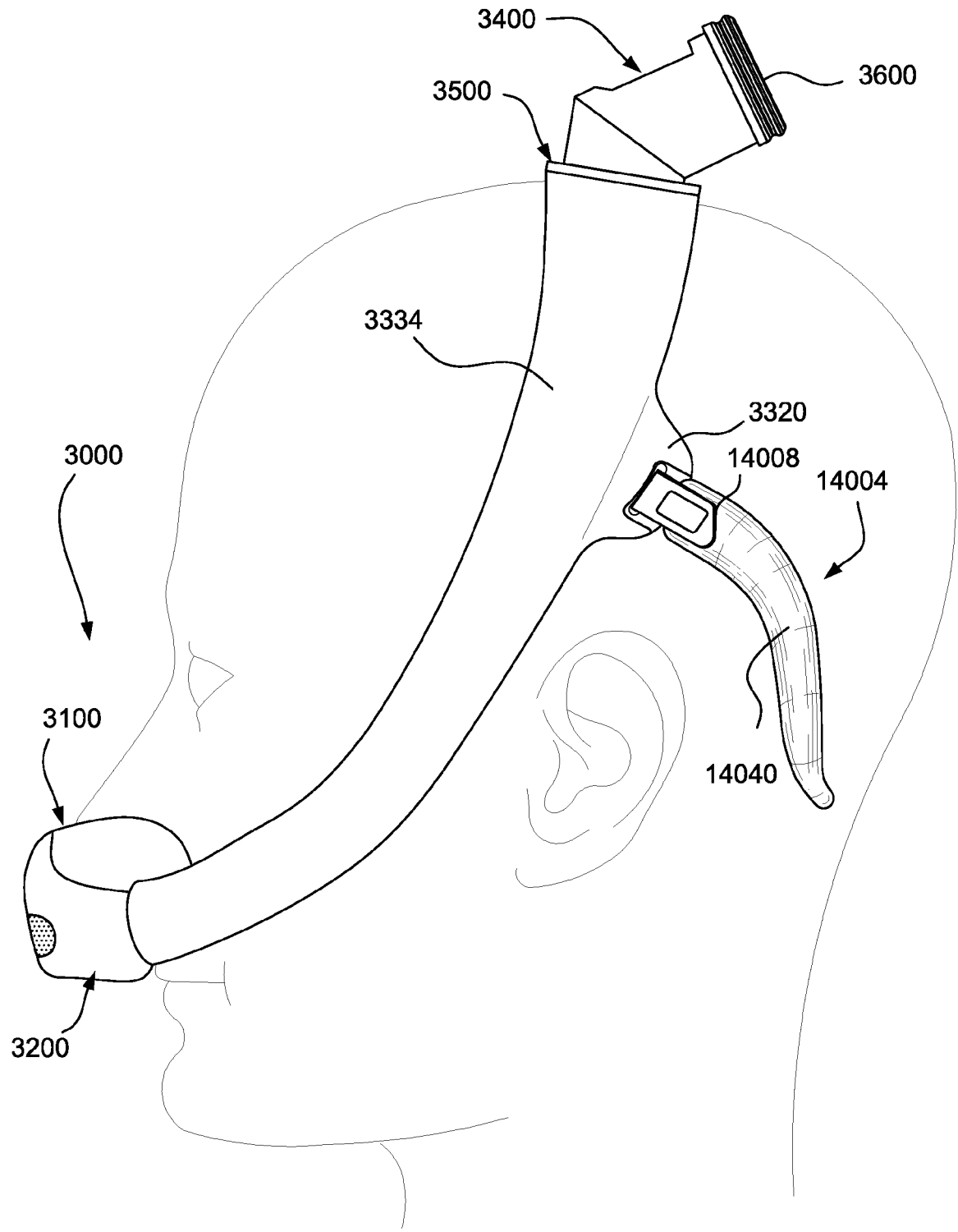

FIG. 83 is a perspective view of the removable arm of FIG. 80, used with a nasal cushion.

Figure 84:
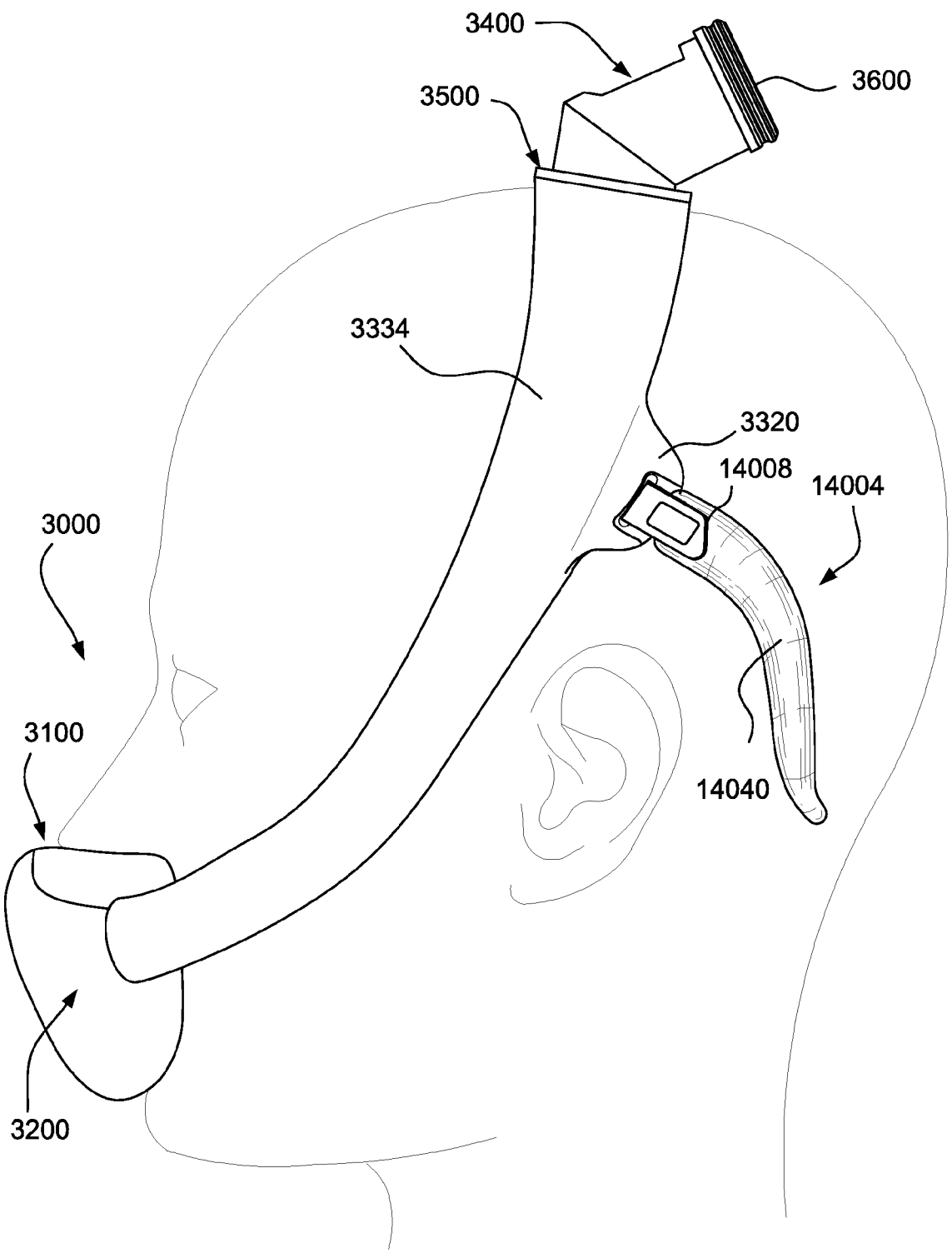

FIG. 84 is a perspective view of the removable arm of FIG. 80, used with a full-face cushion.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising pressuring air to a positive pressure relative to ambient and directing the pressurized air to the entrance of the airways of a patient 1000.

In certain examples of the present technology, a supply of air at positive pressure relative to ambient is provided to the nasal passages of the patient via one or both nares. In further examples, the supply of air at positive pressure may be provided to the mouth, in addition to the nasal passages.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises one or more of the following functional aspects: a seal-forming structure 3100, a plenum chamber 3200, a positioning and stabilizing structure 3300, a vent 3400, one form of connection port 3600 for connection to air circuit 4170, and a forehead support 3700. In some forms, a functional aspect may be performed by one or more physical components. In some forms, one physical component may perform one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 4 $cmH_2O$ with respect to ambient.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 includes a target seal-forming region, and may additionally include a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface 3000 was placed on the face, tension in the positioning and stabilizing structure 3300, and the shape of a patient's face.

In one form, the target seal-forming region is located on an outside surface of the seal-forming structure 3100.

In certain forms of the present technology, the seal-forming structure 3100 is constructed from a biocompatible material, e.g., silicone rubber.

A seal-forming structure 3100 in accordance with the present technology may be constructed from a soft, flexible, resilient material such as silicone.

A seal-forming structure 3100 in accordance with one form of the present technology may be constructed from a textile material 3101 (see e.g., FIGS. 43-52*b*). As shown in FIG. 43, a single piece of textile material 3101 may be used to form the patient interface 3000. Multiple pieces of textile 3101 may also be used to form different sections of the patient interface 3000.

In certain forms of the present technology, a system comprising more than one seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure 3100 includes a sealing flange utilizing a pressure-assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilizing structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilizing structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

In one form of the present technology (see e.g., FIGS. 27-29), the seal-forming structure 3100 includes a hollow sealing tube 3104 that receives the flow of pressurized air. The hollow sealing tube 3104 includes an outer diameter OD in contact with the ambient, and an inner diameter ID positioned proximate the patient's oro-nasal region and not exposed to the ambient while the seal-forming structure 3100 is worn by the patient. An interior surface INS of the hollow sealing tube 3104 may be at least partially impermeable.

In one form (see e.g., FIGS. 44 and 46-48), the hollow sealing tube 3104 is entirely made from and/or lined with the impermeable material. Holes 3108 are cut through the interior surface INS toward the inner diameter ID, and allow air to exit the hollow sealing tube 3104 toward the patient's nose and/or mouth. The holes 3108 may be evenly spaced about the inner diameter ID, or they may be concentrated in a specific area or areas along the inner diameter ID.

In certain forms, the interior surface INS proximate the outer diameter OD is made from and/or lined with an impermeable material (e.g., silicon, a thermoformed and/or laminate structure, etc.), and the interior surface INS proximate the inner diameter ID is made from and/or lined with a permeable material. The hollow sealing tube does not include the holes 3108, so when pressurized air fills the hollow sealing tube 3104, the impermeable material substantially prevents the air from escaping to the ambient. The air is instead directed toward the inner diameter ID, and is able to leak or pass through the permeable material toward the patient's nose and/or mouth.

5.3.1.2 Nose Bridge or Nose Ridge Region

In one form, the non-invasive patient interface 3000 comprises a seal-forming structure that seals in use on a nose bridge region or on a nose-ridge region of the patient's face.

In one form, the seal-forming structure includes a saddle-shaped region constructed to seal in use on a nose bridge region or on a nose-ridge region of the patient's face.

5.3.1.3 Upper Lip Region

In one form, the non-invasive patient interface 3000 comprises a seal-forming structure that seals in use on an upper lip region (that is, the lip superior) of the patient's face.

In one form, the seal-forming structure includes a saddle-shaped region constructed to seal in use on an upper lip region of the patient's face.

5.3.1.4 Chin-Region

In one form the non-invasive patient interface 3000 comprises a seal-forming structure that seals in use on a chin-region of the patient's face.

In one form, the seal-forming structure includes a saddle-shaped region constructed to seal in use on a chin-region of the patient's face.

5.3.1.5 Forehead Region

In one form, the seal-forming structure that seals in use on a forehead region of the patient's face. In such a form, the plenum chamber may cover the eyes in use.

5.3.1.6 Retention Mechanisms

In one form of the present technology, the seal-forming structure 3100 includes at least one retention mechanism 3112 in order to couple an addition component (e.g., the plenum chamber 3200) of the patient interface 3000 to the seal-forming structure 3100.

5.3.1.6.1 Magnetic Retention

As shown in FIG. 46, one form of the seal-forming structure 3100 includes a first magnetic portion 3114. The first magnetic portion 3114 includes a first polarity. In certain forms, the first magnetic portion 3114 is a magnet coupled (e.g., sewn, glued, etc.) into the seal-forming structure 3100. The magnet may be provided in any orientation, and along any length of the seal-forming structure 3100. Multiple magnets may be provided on different sides (e.g., top/bottom, left/right, etc.) of the seal-forming structure 3100. The multiple magnets may have the same polarity as one another. In other examples, the first magnetic portion 3114 may be any similar feature capable of magnetic coupling (e.g., a magnetic thread, a ferrous metal, etc.).

5.3.1.6.2 Mechanical Retention

As shown in FIGS. 49-50*b*, one form of the seal-forming structure 3100 includes a first mechanical retainer or clip structure 3116. In certain forms, the first clip structure 3116 is a made from a rigid material (e.g., plastic, rigid fabric, rigid thread, etc.), and is incorporated (e.g., sewn into) into the seal-forming structure 3100. The first clip structure 3116 includes clips (e.g., a first clip 3116*a*, a second clip 3116*b*, and a gasket 3116*c*) that extend from the surface of the seal-forming structure 3100. The rigid material has a stiffness greater than the stiffness of at least a portion of the remaining material of the seal-forming structure 3100.

In certain forms, the first clip structure 3116 is formed as part of the seal-forming structure 3100. For example, the first clip structure 3116 may be integrally formed with the seal-forming structure 3100, or may be permeantly attached to the seal-forming structure 3100.

In certain forms, the first clip structure 3116 is a male clip structure. A detachment mechanism 3118 may be included with the first clip structure 3116, and is used to uncouple the first clip 3116*a* from a corresponding structure. The detachment mechanism 3118 allows the first clip 3116*a* to move.

5.3.1.7 Nasal Pillows

In one form (see e.g., FIG. 22), the seal-forming structure of the non-invasive patient interface 3000 comprises a pair of nasal puffs, or nasal pillows, each nasal puff or nasal pillow being constructed and arranged to seal with a respective naris of the nose of a patient.

Nasal pillows in accordance with an aspect of the present technology include: a frusto-cone, at least a portion of which seals on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.8 Modular Construction

In one form of the present technology (see e.g., FIGS. 51-52b), the seal-forming structure 3100 is an under the nose mask 3100a that is adapted to engage the patient's upper lip LS and seal against the nares NA while leaving the nasal tip PRO free. The patient's mouth remains exposed to the ambient regardless of the position of the seal-forming structure 3100.

In one form, the plenum chamber 3200 (described below) is incorporated into the seal-forming structure 3100 as an integral or unitary construction. The plenum chamber 3200 includes an insert 3134 with a vent 3400 to assist with the removal of $CO_2$.

In one form, the insert 3134 of the plenum chamber 3200 is at least partially removable from the seal-forming structure 3100, and a mouth seal 3100b is further attached to the under the nose mask 3100a. The mouth seal 3100b covers the patient's mouth from the ambient.

In one form, the mouth seal 3100b is removably coupled to the under the nose mask 3100a using magnetic and/or mechanical coupling. The mouth seal 3100b may include a magnet or a magnetic thread 3142 that is magnetically attracted to a magnet or a magnetic thread 3140 in the under the nose mask 3100a. The mouth seal 3100b may also, or in addition, include a feature (e.g., a tab 3144) that mates with a complementary feature (e.g., a recess 3146) on the under the nose mask 3100a (e.g., via a snap-fit, a press fit, etc.). The tab 3144 may be a rigidized portion (e.g., a rigid fabric, a rigid thread, etc.) form (e.g., integrally) with the mouth seal 3100b. Any combination of the magnetic and mechanical coupling may seal the interface between the under the nose mask 3100a and the face mask, to substantially prevent pressurized air from escaping the seal-forming structure 3100 to the ambient.

In one form, a separate plenum chamber 3200 is removable coupled to both the under the nose mask 3100a and the mouth seal 3100b after the insert has been removed from the under the nose mask 3100a. The plenum chamber 3200 includes a first end 3240 that covers a nose opening 3152a of the nose mask 3100a and a second end 3241 that covers a mouth opening 3152b of the mouth seal 3100b in order to seal the patient's nose and mouth. A conduit 3242 connects the first end 3240 to the second end 3241 in order to provide fluid communication between the patient's nose and mouth. The conduit 3242 may include one or more holes for washout gas.

5.3.2 Plenum Chamber

The plenum chamber 3200 may have a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g., polycarbonate. The use of a transparent material can reduce the obtrusive appearance of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusive appearance of the patient interface, and help improve compliance with therapy.

As shown in FIGS. 46-50b, certain forms of the plenum chamber 3200 are constructed from a textile material 3101. The textile material 3101 can reduce the weight experienced by the patient's face, and help improve compliance with therapy.

In certain forms of the present technology, the plenum chamber 3200 includes a valve 3206 (e.g., an anti-asphyxia valve (AAV)). The AAV 3206 includes a flap 3207 of textile material 3101 on the plenum chamber 3200 that selectively provides fluid communication through a first inlet port 3208 the plenum chamber 3200. The AAV 3206 is biased to an open position, which allows a patient to breathe from the ambient in the absence of a flow of pressurized air. The bias may be a mechanical bias (e.g., a spring), or may be through magnetic repulsion (e.g., two sections with identical polarities). The AAV 3206 closes and blocks communication through the first inlet port 3208 with the ambient when pressurized air is supplied.

5.3.2.1 Removable Plenum Chamber

In certain forms of the present technology (see e.g., FIGS. 46-50b), the plenum chamber 3200 is selectively removable from the seal-forming structure 3100. The plenum chamber 3200 includes a first or decoupled position where the patient's nose and/or mouth is uncovered and exposed to the ambient. The plenum chamber 3200 also includes a second or coupled position where the patient's nose and/or mouth is covered by the plenum chamber 3200. The plenum chamber 3200 is moveable between the decoupled and coupled positions independently of the seal-forming structure 3100. The seal-forming structure 3100 may remain in position (e.g., sealed against a patient's face) regardless of the position of the plenum chamber 3200.

5.3.2.1.1 Magnetic Retention

As shown in FIG. 47, certain forms of the plenum chamber 3200 include a second magnetic portion 3210 with an opposite polarity than the first magnetic portion 3114 of the seal-forming structure 3100. The magnetic portions 3114, 3210 provide the patient with a haptic response to indicate that the plenum chamber 3200 is properly aligned with the seal-forming structure 3100. In some examples, a third magnetic portion 3212 is also included in the plenum chamber 3200. The third magnetic portion 3212 includes the same polarity as the first magnetic portion 3114 (i.e., an opposite polarity than the second magnetic portion 3210).

In certain forms (see e.g. FIG. 48), the second magnetic portion 3210 is a magnet sewn into the textile cover 3204. The magnet may be provided in any orientation, and along any length of the textile cover 3204. Where the third magnetic portion 3212 is included, the second and third magnetic portions 3210, 3212 are disposed on opposite sides of the plenum chamber 3200 (e.g., left/right, top/bottom, etc.). The plenum chamber 3200 couples to the seal-forming structure 3100 when aligned correctly (i.e., the second magnet is adjacent to the first magnetic portion 3114), and is prevented from coupling to the seal-forming structure 3100 when aligned improperly (i.e., the second magnet is distal to the first magnetic portion 3114). In other examples, the second magnetic portion 3210 may be any similar feature capable of magnetic coupling (e.g., a magnetic thread, a ferrous metal, etc.).

When aligned properly (e.g., the first magnetic portion 3114 adjacent to the second magnetic portion 3210), the seal-forming structure 3100 and the plenum chamber 3200 are coupled together and relatively fixed in place. In some forms, the magnetic force is greater than the force of pressurized air, and forms a seal between the seal-forming structure 3100 and the plenum chamber 3200. No additional structure is required in order to retain the plenum chamber 3200 in place and prevent the escape of pressurized air when the patient interface 3000 is in use. In some forms, the magnetic force is less than the force of pressurized air, and an additional structure (e.g., a mechanical fastener—discussed below) helps to retain the plenum chamber 3200 in place and prevent the escape of pressurized air when the patient interface 3000 is in use. In either form, the magnetic force is less than a force applied by a patient's hand (e.g., when moving the plenum chamber 3200 to the decoupled position).

5.3.2.1.2 Mechanical Retention

As shown in FIGS. 49-50b, one form of the plenum chamber 3200 includes a second mechanical retainer or clip structure 3216 with a complementary shape as the first clip structure 3116. The second clip structure 3216 removably mates with the first clip structure 3116 and secures the plenum chamber 3200 in place relative to the seal-forming structure 3100.

In certain forms, the second clip structure 3216 is a made from a rigid material (e.g., plastic, rigid fabric, rigid thread, etc.), and is incorporated (e.g., sewn into) into the textile cover 3204. The second clip structure 3216 extends from the surface of the textile cover 3204 in order to mate with the first clip structure 3116. For example, the second clip structure 3216 may be integrally formed with the plenum chamber 3200.

In certain forms, the second clip structure 3216 is a female clip structure and mates with a male clip structure of the first clip structure 3116; although these may be reversed. A patient aligns the first and second clip structures 3116, 3216 and couples the plenum chamber 3200 to the seal-forming structure 3100 with a snap-fit that provides a seal between the plenum chamber 3200 and the seal-forming structure 3100. Specifically, the patient aligns the second clip structure 3216 with the second clip 3216 (see e.g., FIG. 50a). The patient then actuates the detachment mechanism 3118 to pivot the first clip 3116a away from the magnetic portion 3114. The patient then positions the plenum chamber 3200 proximate the magnetic portion 3114 and releases the detachment mechanism 3118 so that the first clip 3116a contacts the outer surface 3204a (see e.g., FIG. 50b). The gasket 3116c provides a seal between the seal-forming structure 3100 and the plenum chamber 3200 to prevent the flow of fluid between the interface of the seal-forming structure 3100 and the plenum chamber 3200. The female clip portion 3216 may be oriented to complement the second magnetic portion 3210. In other words, the female clip portion 3216 is oriented to couple to the male clip portion 3116 in a single orientation (e.g., which corresponds to the orientation where the first and second magnetic portions 3114, 3210 attract).

In certain forms, the magnetic force between the first magnetic portion 3114 and the second magnetic portion 3210 is insufficient to retain the plenum chamber 3200 to the seal-forming structure 3100 (e.g., the weight of the plenum chamber 3200 exceeds a vertical component of magnetic force). In this case, the magnetic portions 3114, 3210 only provide the patient with a haptic response that the plenum chamber 3200 is properly aligned. The plenum chamber 3200 is retained entirely by the first and second clipping structures 3116, 3216.

In certain forms, the detachment mechanism 3118 is used to uncouple the first and second clip structures 3116, 3216. The detachment mechanism 3118 separates the first clip structure 3116 from the second clip structure 3216 so that the plenum chamber 3200 is moveable to the decoupled position. The detachment mechanism 3118 may be a finger activated detachment mechanism 3118 (e.g., a push button) that separates the first clip structure 3116 from the second clip structure 3216.

5.3.3 Positioning and Stabilizing Structure

The seal-forming structure 3100 of the patient interface 3000 of the present technology may be held in sealing position in use by the positioning and stabilizing structure 3300.

In one form the positioning and stabilizing structure 3300 retains the patient interface 3000 on the patient's head with a force at least sufficient to overcome the effect of the positive pressure in the plenum chamber 3200 urging the seal-forming structure 3100 to lift off the face.

In one form the positioning and stabilizing structure 3300 retains the patient interface 3000 on the patient's head with a force sufficient to overcome the effect of the gravitational force on the patient interface 3000.

In one form the positioning and stabilizing structure 3300 retains the patient interface 3000 on the patient's head with a force as a safety margin to overcome the potential effect of disrupting forces on the patient interface 3000, such as from tube drag, or accidental interference with the patient interface.

In one form of the present technology, a positioning and stabilizing structure 3300 is configured in a manner consistent with being worn by a patient while sleeping. In one example the positioning and stabilizing structure 3300 has a low profile, or cross-sectional thickness, to reduce the perceived or actual bulk of the apparatus. In one example, the positioning and stabilizing structure 3300 comprises at least one strap (e.g., a side strap 3302, a rear strap 3304, and/or a top strap 3306) having a rectangular cross-section. In one example the positioning and stabilizing structure 3300 comprises at least one flat strap.

In one form of the present technology, a positioning and stabilizing structure 3300 is configured so as not to be too large and bulky to prevent the patient from lying in a supine sleeping position with a back region of the patient's head on a pillow.

In one form of the present technology, a positioning and stabilizing structure 3300 is configured so as not to be too large and bulky to prevent the patient from lying in a side sleeping position with a side region of the patient's head on a pillow.

In one form of the present technology, a positioning and stabilizing structure 3300 includes a decoupling portion located between an anterior portion of the positioning and stabilizing structure 3300, and a posterior portion of the positioning and stabilizing structure 3300. The decoupling portion does not resist compression and may be a flexible or floppy strap. The decoupling portion is constructed and arranged so that when the patient lies with their head on a pillow, the presence of the decoupling portion prevents a force on the posterior portion from being transmitted along the positioning and stabilizing structure 3300 and disrupting the seal.

In one form of the present technology, a positioning and stabilizing structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilizing structure 3300 comprises a strap that is extensible, e.g. resiliently extensible. For example the straps 3302, 3304, 3306 may be configured in use to be in tension, and to direct a force to draw a seal-forming structure 3100 into sealing contact with a portion of a patient's face. In an example the straps 3302, 3304, 3306 may be configured as a tie.

In one form of the present technology, the positioning and stabilizing structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilizing structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilizing structure includes a third tie that is constructed and arranged to interconnect the first tie and the second tie to reduce a tendency of the first tie and the second tie to move apart from one another.

In one form of the present technology (see e.g., FIG. 47), the rear strap 3304 of the positioning and stabilizing structure 3300 includes a first magnetic section 3316 (e.g., a magnet, a magnetic thread, etc.). The first magnetic section 3316 is disposed proximate an end of the rear strap 3304. A second magnetic section 3318 (e.g., a magnet, a magnetic thread) with an opposite polarity from the first magnetic section 3316. The first magnetic section 3316 of the rear strap 3304 is removably coupled to the second magnetic section 3318. In the illustrated example, the first magnetic section 3316 is disposed proximate an end of the rear strap 3304. The second magnetic section is spaced apart from the first magnetic section 3316 and includes the opposite polarity from the first magnetic section 3316. In some examples, the magnetic sections may be replaced with another coupling means (e.g., Velcro).

In certain forms of the present technology, a positioning and stabilizing structure 3300 comprises a strap (e.g., the side strap 3302, the rear strap 3304, and/or the top strap 3306) that is bendable and non-rigid. An advantage of this aspect is that the strap 3302, 3304, 3306 is more comfortable for a patient to lie upon while the patient is sleeping.

In certain forms of the present technology, a positioning and stabilizing structure 3300 comprises a strap (e.g., the side strap 3302, the rear strap 3304, and/or the top strap 3306) constructed to be breathable to allow water vapour to be transmitted through the strap 3302, 3304, 3306.

In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

As shown in FIGS. 46 and 47, one form of the positioning and stabilizing structure 3300 includes headgear 3324 formed from a textile material 3101. The headgear 3324 is coupled to the seal-forming structure 3100, and at least a portion of the headgear 3324 and the seal-forming structure 3100 are formed from a one-piece construction of the textile material 3101 (see e.g., FIGS. 43-45). Although, in other forms, the headgear 3324 and the seal-forming structure 3100 may each be formed from individual pieces of textile 3101 and coupled together (e.g., by sewing, gluing, etc.)

In one form, the headgear 3324 of the positioning and stabilizing structure 3300 includes side straps 3302 that are coupled to the seal-forming structure 3100, and extend to a position between the patient's ear and eye when worn by the patient. Specifically, the side straps 3302 extend from a lateral sides of the seal-forming structure 3100, inferior to the patient's eyes and along the patient's cheeks. The side straps 3302 are formed from the textile material 3101.

In one form, the headgear 3324 of the positioning and stabilizing structure 3300 includes a rear strap 3304 that is coupled to the seal forming structure 3100, and engages the occiput of the patient's head (e.g., a rear of the patient's head proximate the occipital bone) when worn by the patient. The rear strap 3304 is formed from a textile material 3101.

In one form, the headgear 3324 of the positioning and stabilizing structure 3300 includes a top strap 3306 that is coupled to the seal forming structure 3100, and engages the top of the patient's head when worn by the patient. The top strap 3306 is formed from a textile material 3101.

In one form, the positioning and stabilizing structure 3300 includes ear pieces 3326 that is coupled to the seal forming structure 3100, and partially or completely surrounds the patient's ears when worn by the patient. The ear pieces 3326 are formed from a textile material 3101.

In certain forms, at least a portion of the position and stabilizing structure 3300 and the seal-forming structure 3100 is a one-piece construction. That is, one or both side straps 3302, the top strap 3306, the rear strap 3304, and/or the ear pieces 3326 are formed as a one-piece construction with the seal-forming structure 3100. For example, at least one of the side straps 3302 is integrally formed with the seal-forming structure 3100, and is not removable from the seal-forming structure 3100. The interface between the side strap and the seal-forming structure 3100 may be a seamless transition 3328.

In certain forms, transition 3328 may be visible to an observer (e.g., the bed partner 1100) as a result of bending or flexing of the side strap 3302 relative to the seal-forming structure 3100. In other words, the transition 3328 may be a crease that delineates the transition between the headgear 3324 and the seal-forming structure 3100 (e.g., the side straps 3302 may bend outwardly or away from the patient as they follow the contours of the patient). The transition 3328 may also be the result of pressurized air expanding the seal-forming structure 3100 and/or the side straps 3302 (e.g., the seal-forming structure 3100 and/or the side straps 3302 inflate to different shapes on either side of the transition 3328).

In certain forms, the ear pieces 3326 are formed with the side straps 3302 as a single piece of textile material 3101, and coupled to the seal-forming structure 3100 indirectly through the respective side strap. The top strap 3306 is formed with either the side straps 3302 or the ear straps as a single piece of textile material 3101, and coupled to the seal-forming structure 3100 indirectly through the side straps 3302. The rear strap 3304 is formed directly with the seal-forming structure 3100, or is formed directly with the side straps 3302 and coupled to the seal-forming structure 3100 indirectly through the side straps 3302.

5.3.3.1 Used for Airflow

As shown in FIGS. 46-48, one form of the side straps 3302 is at least a portion of hollow tubes 3334 that convey pressurized air toward the seal-forming structure 3100. The hollow tubes 3334 made from and/or lined with an impermeable material (e.g., silicon, a thermoformed and/or laminate structure, etc.). The hollow tubes 3334 couple to the seal-forming structure 3100 with a seamless or substantially seamless transition (e.g., at joint 3328) at a seal end 3308 in order to prevent or substantially prevent the escape of pressurized air toward the ambient. In one example, the hollow tubes 3334 are dual lumen tubes.

In certain forms (see e.g., FIG. 43), a single piece of textile 3101 is used to make the side straps 3302 and the seal-forming structure 3100. As the patient interface 3000 is constructed (e.g., to give the seal-forming structure 3100 depth and form the side straps 3302 as hollow tubes 3334), the side straps 3302 transition to the seal-forming structure 3100 at a substantially smooth joint 3328 (see e.g., FIGS. 44 and 46). For example, while a visible transition exists at the joint 3328 as a result of the different shapes of the seal-forming structure 3100 and the side straps 3302, the same piece of textile 3101 is used on either side of the joint 3328. Particularly, the inner surface 3130 of the seal-forming structure 3100 and an inner surface 3342 of the side straps 3302 both rest against the patient's face while the patient interface 3000 is in use. The side strap 3302 extends to the seal-forming structure 3100 (e.g., in an anterior and inferior direction along the patient's face), so that as viewed by the patient, there is almost no visible joint 3328 between the inner surfaces 3130, 3342.

As shown in FIG. 47, certain forms of the seal-forming structure 3100 are a gasket type seal. The seal-forming structure 3100 forms a hollow sealing tube 3104, and the hollow tubes 3334 extend to an interior surface INS of the hollow sealing tube 3104. Pressurized air is conveyed into the interior (e.g., adjacent to the interior surface INS) of the hollow sealing tube 3104, and inflates the hollow sealing tube 3104. The air then exits the hollow sealing tube 3104 in order to reach the patient's face.

As shown in FIGS. 46 and 47, a connector 3335 is used to couple the two hollow tubes 3334 of the side straps 3302 together in one form of the present technology. The connector 3335 includes a second inlet port 3336, although the second inlet port 3336 may also be positioned on the positioning and stabilizing structure 3300 (e.g., on the side straps 3302, on the top strap 3306, etc.). The second inlet port 3336 provides communication between the ambient and the hollow tubes 3334 of the side straps 3302. The second inlet port 3336 may allow the patient to breathe from the ambient in the absence of pressurized air. The connector 3335 may be formed at a mid-portion of the hollow tubes 3334, in order to divide the hollow tubes 3334 into two substantially equal lengths.

The positioning and stabilizing structure 3300 may include a valve 3339 with flap 3338 that is adjacent to the second inlet port 3336 (see e.g., FIGS. 64 and 66). The flap 3338 is biased (e.g., magnetically, mechanically, etc.) to an open position (i.e., to allow airflow through the second inlet port 3336), and may move to a closed position (i.e., substantially limiting airflow through the second inlet port 3336) as the result of pressurized air being provided (e.g., through the first inlet of the plenum chamber 3200).

In one form (see e.g., FIGS. 51 and 52), the under the nose mask 3100a and the mouth seal 3100b each include side straps 3302 so that tension is applied to both the under the nose mask 3100a and the mouth seal 3100b. The side strap 3302a of the under the nose mask 3100a may be part of the hollow tube 3334. The side strap 3302b of the mouth seal 3100b may be only a strip of fabric that does not convey pressurized air toward the mouth seal 3100b.

5.3.3.2 Ear Bypass

As described and shown with respect to FIGS. 46 and 47, the headgear 3324 of the positioning and stabilizing structure 3300 includes hollow tubes 3334, which convey pressurized air toward the seal-forming structure 3100. Since the hollow tubes 3334 are part of the positioning and stabilizing structure 3300, they need to conform to a particular patient's head, while also providing a snug fit. If the hollow tubes 3334 do not conform to the patient's head and is too tight, the patient interface 3000 may be uncomfortable, causing the patient to be less likely to comply with therapy. Additionally, if the hollow tubes 3334 are not able to tighten against the patient's head, the seal-forming structure 3100 may not seal with the patient's face, which may lead to ineffective therapy. In the illustrated example, the hollow tubes 3334 may be formed from a one-piece construction, and the hollow tubes 3334 together form a single conduit.

Specifically, the position of the headgear 3324 relative to the patient's head may shift while in use. For example, the patient may roll in their sleep, which may cause at least one strap (e.g., the side strap 3302, the rear strap 3304, and the top strap 3306) to shift against the patient's head. This may particularly affect the rear strap 3304, which may translate or shift because it remains in contact with the patient's bed and/or pillow in most sleeping positions (e.g., sleeping on back, sleeping on side, etc.). If the rear strap 3304 shifts too much on the patient's head (e.g., in the superior/inferior direction), the seal-forming structure 3100 may become loose on the patient's face, and no longer in the therapeutically effective position (e.g., pressurized air may leak into the atmosphere instead of being directed to the patient's lungs). This may occur when the rear strap 3304 is tightened around the patient's head while inclined with respect to the Frankfort Horizontal FFH (see e.g., FIG. 8). If the rear strap 3304 later moves to a position where the angle relative to the Frankfort Horizontal FFH is less than when initially tightened (e.g., in the superior direction), then the rear strap 3304 may no longer be tight enough to hold the seal-forming structure 3100 in the proper position. Movement of the rear strap 3304 may be particularly problematic in patients with longer hair, which may prevent the rear strap 3304 from effectively gripping the patient's head. Longer hair, either alone or in addition to movement during sleep (e.g., rolling in bed), may increase the movement of the rear strap 3304 into a non-effective position (i.e., a position where the rear strap 3304 is unable to provide the proper force for sealing the seal-forming structure 3100).

As shown in FIGS. 53-63, the rear strap 3304 may be constructed partially from a first material 3348 having a first coefficient of friction and a second material 3349 having a second coefficient of friction that is greater than the first coefficient of friction. The second material 3349 helps to maintain the position of the rear strap 3304 (e.g., angled in a posterior and inferior direction) against the patient's head. The second material 3349 may also be rigid or semi-rigid. The first material 3348 and the second material 3349 may be coupled together through sewing, sonic welding, adhesives, or in any similar manner.

The rear strap 3304 includes a side portion or side portion 3350 and a second section 3354. The side portion 3350 is constructed from the first material and the second section 3354 is constructed from the second material. In the illustrated example, the second section 3354 is positioned between two side portions 3350a, 3350b. The side portions 3350a, 3350b generally extend from the second section 3354 toward either side of the hollow tube 3334 and the respective tab 3320, while the patient interface 3000 is in use.

The side portion 3350 is coupled to the second section 3354 at a transition or joint 3355. The joint 3355 may be sewn, glued, sonic welded, fused, or any similar method. In the illustrated example, only one material (e.g., the first material 3348 or the second material 3349) is present on either side of the joint 3355. In other words, the side portion 3350 does not substantially overlap with the second section 3354. Each material 3348, 3349 is exposed in each section (i.e., the first section 3350 and the second section 3354), which allows the patient to feel and experience the physical properties (e.g., coefficient of friction) associated with each material. Thus, no first material 3348 extends substantially along the length of the second section 3354, and no second material 3349 extends substantially along the length of the first section 3350.

In one form, the second section 3354 is formed as a pad that contacts the occiput of the patient. The pad 3354 may have a thickness that is greater than the thickness of the side portions 3350a, 3350b. The pad 3354 is capable of gripping or hooking at the occiput, and provide an anchoring point on the patient's head. The engagement with the patient's head may substantially limit the translation of the pad 3354 along the patient's head. The increased thickness of the pad 3354 may provide additional gripping strength and better limit the translation of the pad 3354 while the patient interface 3000 is in use. Also, or in addition, the increased thickness of the pad 3354 may provide additional cushioning to the patient's occiput.

Figure 6:
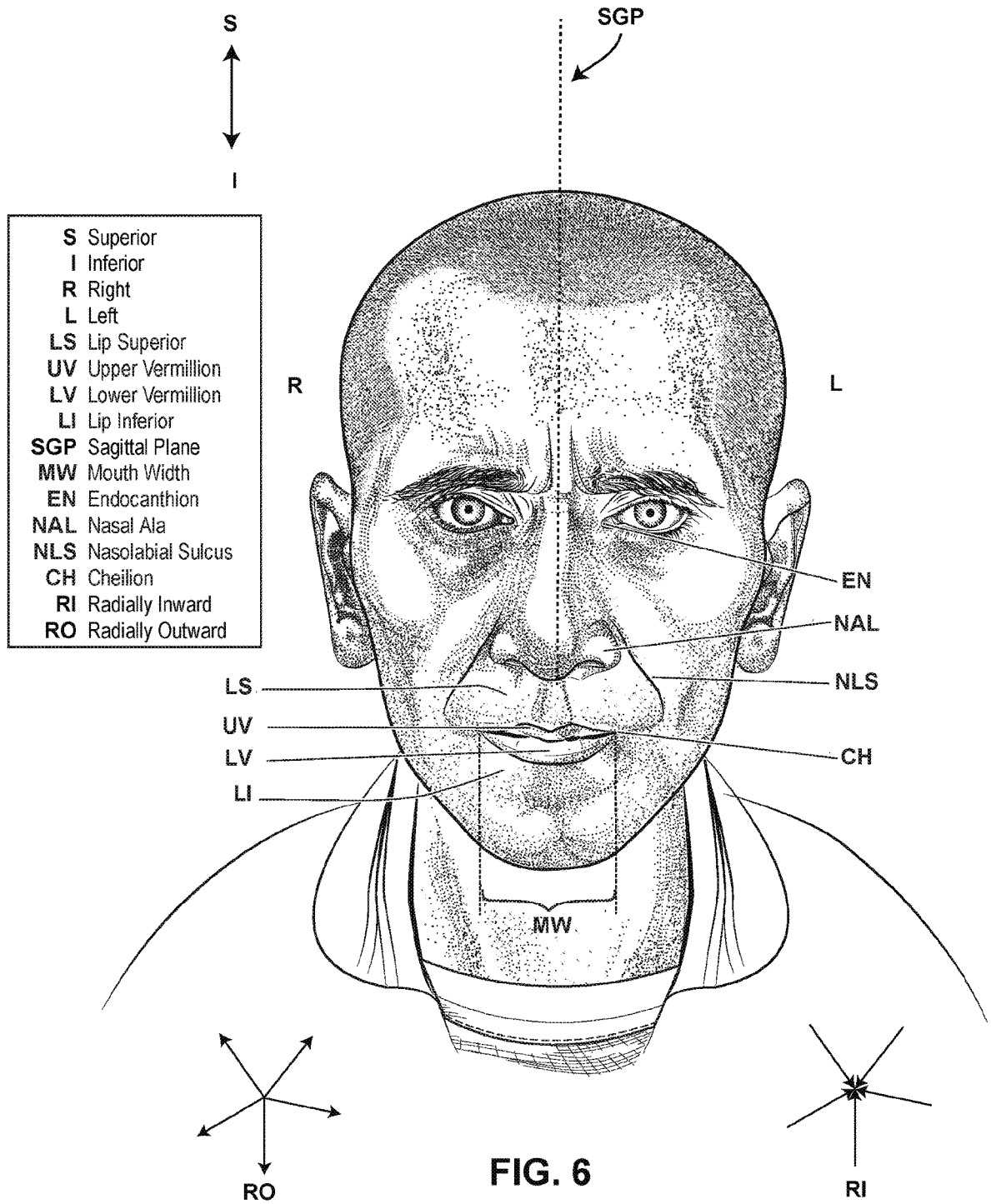
FIG. 6 is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 7:
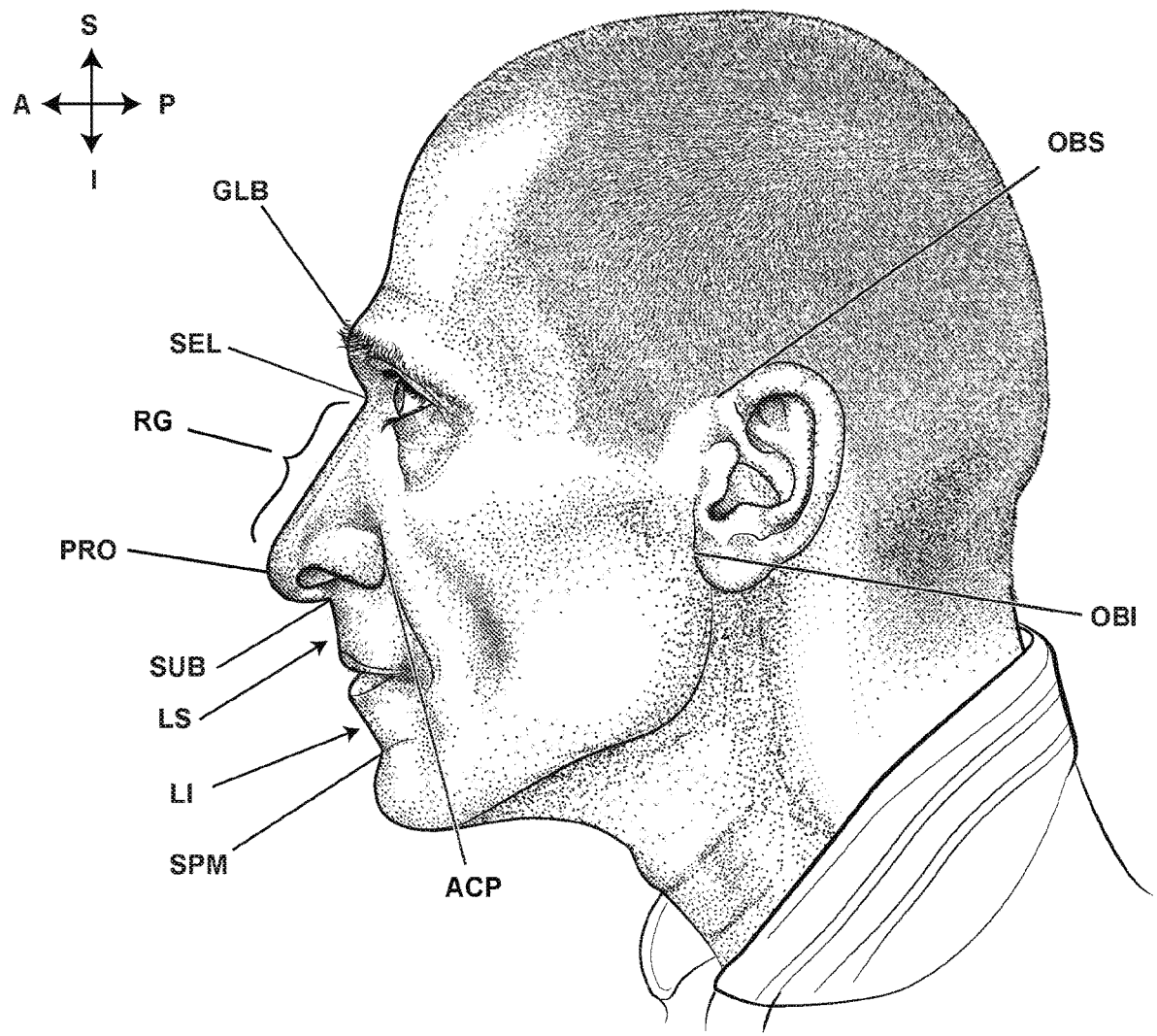
FIG. 7 is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

In the illustrated example, the pad 3354 includes a curvature about the sagittal plane SGP (see e.g., FIG. 6). The pad 3354 may be concave with respect to the occipital bone OCC (see e.g., FIG. 14), and directed in the superior direction. The curvature of the pad 3354 may assist the rear strap 3304 in further gripping and hooking into the occiput of the patient, and maintaining the position of the rear strap 3304 with respect to the patient's head. In other words, the pad 3354 may hook around the base of the occipital bone in order to limit superior translation of the rear strap 3304.

In one form, side portion 3350a, 3350b is constructed from a textile. The textile side portions 3350a, 3350b may be flexible and non-abrasive against a patient's head. For example, the textile is able to conform to the patient's head and may not cause irritation around sensitive areas (e.g., the patient's temples). The textile also may be able to stretch when a tensile force is applied in order to conform to differently sized patient's heads. In other forms, the side portion 3350a, 3350b is an elastic, which may be capable of stretching to a greater length than the textile. The elastic may stretch as the patient dons the headgear 3000, in order to allow the headgear to be used with multiple sizes of heads.

The pad 3354 is constructed from silicone, or a similar material (e.g., hytrel). The pad 3354 may have a greater stiffness than the textile of the side portions 3350a, 3350b so that it may provide a better anchor for the positioning and stabilizing structure 3300. The patient's hair will generally be positioned between the pad 3354 and the patient's skin, so the pad 3354 may not cause a substantial amount of irritation to the patient's skin.

The physical properties (e.g., shape, coefficient of friction, stiffness, etc.) of the pad 3354 limit the total area occupied by the rear strap 3304 on the patient's head. Since the rear strap 3304 is able to hook or engage the occiput, the portion of the rear strap is not required on a superior region of the patient's head. For example, the rear strap 3304 would not extend across the parietal bone PAR (see e.g., FIG. 14) in a lateral (e.g., left/right direction). In particular, the second material 3349 may not contact the parietal bone PAR.

The pad 3354 may also not extend in the temporal region (e.g., across the temporal bone TTEM), and may be confined to the occipital region (e.g., across the occipital bone OCC). This may position the second material in the posterior of the patient's head.

As shown in FIGS. 53 and 54, each side portion 3350a, 3350b of the rear strap 3304 is connected directly to the pad 3354 and to an intermediate section 3346 of the positioning and stabilizing structure 3300. Each intermediate section 3346 (i.e., right and left intermediate sections) delineates the transition between respective side strap 3302 and the top strap 3306. In the illustrated example, the tab 3320 extends from the intermediate section 3346, and is coupled to the respective side portion 3350a, 3350b. Each side portion 3350a, 3350b is angled relative to the Frankfort Horizontal FFH so that the pad 3354 may be positioned proximate to the occiput. When the rear strap 3304 is tightened against the patient's head, the pad 3354 hooks into the occiput, and limits further movement of the rear strap 3304.

In the illustrated example, the side portions 3350a, 3350b extend parallel to a tangent line $L_1$ along a helix H of each respective ear. The line $L_1$ intersects an apex axis AA, which extends orthogonally with respect to the Frankfort Horizontal FFH through an apex A of the ear, at an angle φ. The apex A represents the most superior portion of the patient's ear. The side portions 3350a, 3350b may then be completely behind the patient's ears so that the likelihood of the side portion 3350a, 3350b intersecting (i.e., contacting) either ear is significantly reduced.

In one example, the angle φ is between 0° and 60°. In one example, the angle φ is between 10° and 55°. In one example, the angle φ is between 20° and 50°. In one example, the angle φ is between 30° and 45°. In one example, the angle φ is approximately 43°.

In the illustrated example, each tab 3320 is positioned above the patient's ears, in a location that does not interfere with either of the patient's ears. For example, each tab 3320 is positioned sufficiently toward the superior region of the patient's head so that the side portions 3350a, 3350b may extend toward the occiput without intersecting the patient's ear. In other words, each side portion 3350a, 3350b is permitted to extend above and/or behind each ear in order to avoid contacting either ear. This provides some comfort to the patient, because the rear strap 3304 is not pressing the patient's ears against their head.

In the illustrated example of FIGS. 53 and 54, the positioning and stabilizing structure 3300 may not include lower straps. In other words, the positioning and stabilizing structure 3300 may not include straps that extend along the patient's cheek (e.g., over the masseter muscle) and between the pad 3354 and/or side portion 3350 and the plenum chamber 3200. In other examples, the positioning and stabilizing structure 3300 may include lower straps.

In the illustrated examples of FIGS. 53 and 54, the positioning and stabilizing structure 3300 may not include bottom straps and/or top straps. In other words, the positioning and stabilizing structure 3300 may not include straps that extend below the patient's chin (e.g., below the mental protuberance). The positioning and stabilizing structure 3300 also may not include straps that extend toward the crown of the patient's head (e.g., along the parietal bone toward the control plane). In other examples, the positioning and stabilizing structure 3300 may include top straps and/or bottom straps.

As shown in FIGS. 55 and 56, the rear strap 3304 may further include a pair of third sections or extenders 3358a, 3358b. Each extender 3358a, 3358b is directly connected to a respective tab 3320 and to a side portion 3350a, 3350b. In other words, each side portion 3350a, 3350b is connected to the tab 3320 through the extender 3358a, 3358b. The extender 3358a, 3358b is constructed from a third material 3361 that is different from the first material 3348. In some examples, the third material 3361 may be the same as the second material 3349 (e.g., the material used to construct the pad 3354). In other examples, the third material 3361 may be different than both the first and second materials 3348, 3349. The third material 3361 may also have a coefficient of friction that is greater than the coefficient of friction of the first material 3348. This helps to better anchor each extender 3358a, 3358b against the patient's head, and limit translational motion as a result of a tensile force (e.g., from the side portions 3350a, 3350b).

The second material 3349 may be positioned in the temporal region if the the third material 3361 is the same as the second material 3349. However, the second material (e.g., the extenders 3358a, 3358b) would be positioned above the otobasion inferior on the temporal region. Thus, the second material 3349 would not pass across the Digastricus muscle or the Sternocleidomastoid muscle.

In one form, the third material is a stiffened material, and the extenders 3358a, 3358b are formed as an angled piece. Each extender 3358a, 3358b includes a first or generally horizontal portion 3359 and a second or inclined portion 3360. The generally horizontal portion 3359 extends generally parallel to the Frankfort Horizontal FFH. The generally horizontal portion 3359 may extend along the Frankfort Horizontal FFH in the posterior direction to a location beyond a majority of the patient's ears. For example, the generally horizontal portion 3359 may extend to at least the apex A of the patient's ear. In other words, the generally horizontal portion 3359 extends in the posterior direction and intersect the apex axis AA. In some examples, the generally horizontal portion 3359 may extend beyond the apex axis AA in the posterior direction. In some embodiments, the generally horizontal portion 3359 is positioned entirely on the temporal bone TTEM (see e.g., FIG. 14).

The inclined portion 3360 extends further in the posterior direction with respect to the generally horizontal portion 3359, and is inclined relative to the generally horizontal portion (e.g., forms an acute angle relative to the Frankfort Horizontal FFH). For example, each extender 3358a, 3358b is concave with respect to the respective ear. A transition between the generally horizontal portion 3359 and the inclined portion 3360 may being along the apex axis AA. The inclined portion 3360 may then extend in the posterior direction parallel to a line $L_2$ that is tangent to a helix H of the patient's ear. The line $L_2$ intersects the apex axis AA at an angle θ. The inclined portion 3360 may then be completely behind the patient's ears so that the likelihood of the side portion 3350a, 3350b intersecting either ear is significantly reduced.

In one example, the angle θ is between 0° and 60°. In one example, the angle θ is between 10° and 55°. In one example, the angle θ is between 20° and 50°. In one example, the angle θ is between 30° and 45°. In one example, the angle θ is approximately 40°.

The extender 3358a, 3358b serves to change the angle of the side portions 3350a, 3350b relative to the patient's ear. The generally horizontal portion 3359 disposes each side portion 3350a, 3350b away from the respective tab 3320 so that the side portion 3350a, 3350b does not need to extend as far to the patient's occiput (e.g., as compared to the example in FIG. 53). Additionally, the angle of the side portion 3350a, 3350b relative to the Frankfort Horizontal FFH in FIG. 55 is greater than the same angle in FIG. 53. In other words, the side portion 3350a, 3350b extends more in the inferior direction than the posterior direction, as compared to the side portion of FIG. 53. A greater component of force provided by the rear strap 3304 may be directed in the inferior/superior direction. A smaller total force, as compared to the example of FIG. 53, may be used to provide the same engagement force on the pad 3354. In other words, the patient may tighten the rear strap 3304 less against their head in order to achieve the necessary force vector in the inferior/superior direction to hook the pad 3354 into the occiput.

Extending the generally horizontal portion 3359 beyond or substantially beyond the patient's ears further reduces the likelihood that the side portion 3350a, 3350b contacts either of the patient's ears. By extending the generally horizontal portion 3359 beyond or substantially beyond the patient's ears, the inclined portion 3360 extends further beyond the patient's ears so the first portion 3350a, 3350b is entirely behind and spaced apart from the patient's ears. In the previous example (see e.g., FIGS. 53 and 54), the side portions 3350a, 3350b could slide against the patient's head and cause the rear strap 3304 to pinch the respective ear. In this example, the extender completely spaces the side portion 3350a, 3350b from the respective ear, so that even minor translations of the side portion 3350a, 3350b will not result in the respective ear being pinched.

In certain forms, the extender 3358a, 3358b may be adjustable. For example, the third material may allow for minor adjustments, while still maintaining its general shape. The patient may be able to change the angle between the generally horizontal portion 3359 and the inclined portion 3360. This allows the patient to adjust the position of the side portion 3350a, 3350b based on the size of the patient's head. For example, the tab 3320 may be positioned more superior on a patient with a longer head. Thus, the patient may be able to increase the angle between the generally horizontal portion 3359 and the inclined portion 3360 in order to direct the side portion 3350a, 3350b toward the inferior region of the patient's head (e.g., toward the occiput). Once the inclined portion 3360 is set to a desired position, it remains generally rigid or semi-rigid and substantially maintains its shape when the rear strap 3304 is tightened.

In the illustrated example of FIGS. 55 and 56, the positioning and stabilizing structure 3300 may not include lower straps. In other words, the positioning and stabilizing structure 3300 may not include straps that extend along the patient's cheek (e.g., over the masseter muscle) and between the pad 3354 and/or side portion 3350 and the plenum chamber 3200. In other examples, the positioning and stabilizing structure 3300 may include lower straps.

In the illustrated examples of FIGS. 55 and 56, the positioning and stabilizing structure 3300 may not include bottom straps and/or top straps. In other words, the positioning and stabilizing structure 3300 may not include straps that extend below the patient's chin (e.g., below the mental protuberance). The positioning and stabilizing structure 3300 also may not include straps that extend toward the crown of the patient's head (e.g., along the parietal bone toward the control plane). In other examples, the positioning and stabilizing structure 3300 may include top straps and/or bottom straps.

As shown in FIGS. 57 and 58, the seal-forming structure 3100 may include an under the nose mask 3100*a* and mouth seal 3100*b*, as opposed to just a nose mask 3100*a* of FIGS. 53-56. The under the nose mask 3100*a* and mouth seal 3100*b* may be formed as a single piece, or they may be individual pieces that are coupled together as described above (see e.g., FIGS. 51-52*b*). The positioning and stabilizing structure 3300 used with the seal forming structure 3100 of FIGS. 57 and 58 may be similar to the positioning and stabilizing structure 3300 of FIGS. 53-56, and only some similarities and differences are described.

In one form, the under the nose mask 3100*a* includes the side strap 3302*a* and the mouth seal 3100*b* includes the side strap 3302*b*. The side strap 3302*b* extends from proximate the patient's mouth in a direction generally parallel to the Frankfort Horizontal FFH. The side strap 3302*b* extends along the patient's cheek and neck, and is disposed entirely below the patient's ears. Thus, the side straps 3302*a*, 3302*b* and the rear strap 3304 define a perimeter around each of the patient's ears, but do not contact the ears.

In certain forms, the side strap 3302*b* is disposed further inferior than the pad 3354. The side strap 3302*b* may be movable relative to the pad 3354, which may lead to similar problems for the seal-forming structure 3100 (e.g., the side strap 3302*b* moves relative to the patient's head, causing the seal-forming structure 3100 to become too loose). In order to limit this movement, a connection strap 3362 may be used to connect the pad 3354 to the side strap 3302*b*. The connection strap 3362 provides a rigid engagement between the pad 3354 and the side strap 3302*b* and limits relative movement between the two. Specifically, the side strap 3302*b* is limited from moving because the pad 3354 is hooked against the patient's occiput.

In certain forms the connection strap 3362 is disposed centrally along the patient's neck, while the patient is wearing the patient interface 3000. In the illustrated example, the connection strap 3362 is constructed from the first material (e.g., textile). The side strap 3302*b* and the connection strap 3362 may be constructed from a single piece of material. In other examples, the connection strap 3362 may be constructed from the second material, and may be formed as a one-piece construction with the pad 3354. In this example, the connection strap 3362 may provide additional gripping against the patient to prevent movement of the positioning and stabilizing structure 3300. In other examples, the connection strap 3362 is coupled to the side strap 3302*b* and the pad 3354, and may be formed from any material.

In the illustrated examples of FIGS. 57 and 58, the positioning and stabilizing structure 3300 may not include bottom straps and/or top straps. In other words, the positioning and stabilizing structure 3300 may not include straps that extend below the patient's chin (e.g., below the mental protuberance). The positioning and stabilizing structure 3300 also may not include straps that extend toward the crown of the patient's head (e.g., along the parietal bone toward the control plane). In other examples, the positioning and stabilizing structure 3300 may include top straps and/or bottom straps.

As shown in FIG. 59, some examples of the seal-forming structure 3100 with an under the nose mask 3100*a* and mouth seal 3100*b* may not utilize the side strap 3302*b*. The rear strap 3304 may provide a sufficient force to maintain the seal-forming structure 3100 in the therapeutically effective position. Specifically, the pad 3304 may maintain the seal-forming structure 3100 in the appropriate position, without necessitating the side strap 3302*b* or the connection strap 3362. This may provide more comfort for the patient, because the positioning and stabilizing structure 3300 would not pass over the Sternocleidomastoid muscle STE (see e.g., FIG. 14) of the patient. The side strap 3302*b* may be omitted whether or not the extender 3358 is used.

In the illustrated example of FIG. 59, the positioning and stabilizing structure 3300 may not include lower straps. In other words, the positioning and stabilizing structure 3300 may not include straps that extend along the patient's cheek (e.g., over the masseter muscle) and between the pad 3354 and/or side portion 3350 and the plenum chamber 3200. In other examples, the positioning and stabilizing structure 3300 may include lower straps.

In the illustrated examples of FIG. 59, the positioning and stabilizing structure 3300 may not include bottom straps and/or top straps. In other words, the positioning and stabilizing structure 3300 may not include straps that extend below the patient's chin (e.g., below the mental protuberance). The positioning and stabilizing structure 3300 also may not include straps that extend toward the crown of the patient's head (e.g., along the parietal bone toward the control plane). In other examples, the positioning and stabilizing structure 3300 may include top straps and/or bottom straps As shown in FIG. 60, the tab 3320, in certain forms of the positioning and stabilizing structure 3300, is an eyelet or loop 3320 that selectively receives the rear strap 3304 (e.g., 3350*a*, 3350*b*). The rear strap 3304 is therefore removably coupled to the loop 3320, and may be disconnected in order to assist the patient in donning and doffing the patient interface 3000.

In one form, one of the side portions 3350*a*, 3350*b* is threaded through the loop 3320 and doubled back on itself in order to allow the first magnetic section 3316 to couple to the second magnetic section 3318. The second magnetic section 3318 may be larger (i.e., include a larger area on the side portion 3350*a*, 3350*b*) than the first magnetic section 3316, so that the first magnetic section 3316 can couple to the second magnetic section 3318 in a variety of positions (e.g., corresponding with a different tightness). Alternatively, the first and second magnetic sections 3316, 3318 may be replaced with Velcro, or any similar fastener.

In certain forms, only one of the tabs 3320 defines a loop. In other words, the rear strap 3304 may be permanently coupled to one of the tabs 3320 (e.g., the right side portion 3350*b*) and may be removably coupled to the other tab 3320 (e.g., the left side portion 3350*a*). The rear strap 3304 may be formed as a one-piece construction (e.g., from one piece of textile) with the tab 3320 that it is permanently coupled to.

As shown in FIG. 61, one extender 3358*a* is threaded through the loop 3320 and doubled back on itself in order to allow a first engagement section 3366 to couple to a second engagement section 3368. The second engagement section

3368 may be larger (i.e., include a larger area on the rear strap 3304) than the first engagement section 3366, so that the first engagement section 3366 can couple to the second engagement section 3368 in a variety of positions (e.g., corresponding with a different tightness). In the illustrated example, the first and second engagement sections 3366, 3368 are magnetic sections, although in other examples, other engagement mechanisms may be used (e.g., Velcro). The first and second engagement sections 3366, 3368 may be disposed on the generally horizontal portion 3359, so that engagement between the engagement sections 3366, 3368 affects the position of the side portions 3350a, 3350b with respect to the tabs 3320, but not the angle with respect to the Frankfort Horizontal FFH.

In certain forms, only one of the tabs 3320 defines a loop. In other words, the one extender 3358b may be permanently coupled to one of the tabs 3320 (e.g., the right tab 3320) and the other extender 3358a may be removably coupled to the other tab 3320 (e.g., the left loop 3320).

In certain forms, the side portions 3350a, 3350b are permanently coupled to the respective extenders 3358a, 3358b. The distance between the pad 3354 and the extenders 3358 remains substantially constant. An adjustment of the rear strap 3304 by the patient may be restricted to the extender(s) 3358a, 3358b.

As shown in FIG. 62, the extender 3358a includes a loop 3380 on the inclined portion. The side portion 3350a may be threaded through the loop 3380 and doubled back on itself in order to removably couple the side portion 3350a to the respective extender 3358a. The first magnetic section 3316 and the second magnetic section 3318 are used to removably coupled the side portion 3350a to the extender 3358a.

In certain examples, the extender 3358a is also removably coupled to the loop 3320 (see e.g., FIG. 61). The patient may selectively use the extender 3358a as necessary (e.g., based on a size of the patient's head, the required force, etc.). When the extender 3358a is not necessary, the patient may couple the side portion 3350a to the loop as shown in FIG. 59.

In certain forms, only one of the tabs 3320 defines a loop. In other words, the one extender 3358b may be permanently coupled to one of the tabs 3320 (e.g., the left tab 3320) and the other extender 3358a may be removably coupled to the other tab 3320 (e.g., the right loop 3320). The extender 3358a may be formed as a one-piece construction with the tab 3320 that it is permanently coupled to (e.g., from one piece of textile).

Similarly, the only one of the extenders 3358a, 3358b may define a loop 3380. In other words, the one extender 3358b may be permanently coupled to one of the side portions 3350b (e.g., the right tab 3320) and the other extender 3358a may be removably coupled to the other side portion 3350a (e.g., the left loop 3320). The patient may only be able to make adjustments to the rear strap 3304 on one side (e.g., the left side).

As shown in FIGS. 63 and 64, the pad 3354 may be adjustable in order to conform to the patient's head. Specifically, a length of the pad 3354 is adjustable by the patient in order to tighten or loosen the pad 3354 against the patient's head.

As shown in FIG. 63, the pad 3354 includes a side portion 3354a and a second section 3354b that are coupled together using a buckle 3370 (e.g., a ladder lock buckle). The side portion 3354a and the second section 3354b are configured to overlap one another. The second section 3354b is movable relative to the side portion 3354a, in order to determine the length that overlaps. A useable length of the pad 3354 corresponds to a total length of the first and second sections 3354a, 3354b that is exposed to and/or contacts the patient. The first and second sections 3354a, 3354b are threaded through the buckle 3370, and are retained in their desired position. For example, the patient may adjust the length of the second section 3354b threaded through the buckle 3370 so that the pad 3354 is comfortable and in a secured position against their head.

As shown in FIG. 64, the pad 3354 may include a side portion 3354a with a plurality of apertures 3374, and a second section 3354b with a plurality of projections 3378. Each aperture 3374 is configured to receive one of the projections 3378. The side portion 3354a is selectively positioned along the length of the second section 3354b so that at least one of the apertures 3374 may engage one of the projections 3378. Each aperture 3374 may receive any one of the projections 3378 depending on the desired length of the pad 3354. The patient may select the appropriate relative position between the first and second sections 3354a, 3354b, so that the pad 3354 is secured to the patient's head.

In certain forms, the pad 3354 may be the only means of adjusting the length of the rear strap 3304 (e.g., via the buckle 3370, via the apertures 3374 and projections 3378, via magnets, or via a similar mechanism). The patient may loosen the pad 3354 (e.g., the side portion 3354a relative to the second section 3354b) in order to don and doff the patient interface 3000.

In certain forms, the pad 3354 may be adjustable in addition to the side portion 3350a, 3350b and/or the extenders 3358a, 3358b. Together, these different forms of adjustment may allow the patient to make smaller, more finite, adjustments in order to secure the pad 3354 against the patient's occiput in an ideal position.

5.3.3.3 Full-Face Mask Specific Anchor

As described above, some forms of the positioning and stabilizing structure 3300 used in a nasal mask (see e.g., FIGS. 53-56) may also be used in a full-face mask (see e.g., FIGS. 57-59). Additionally, positioning and stabilizing structures may be designed specifically for full-face masks in order to better assist in sealing around the patient's nares and mouth.

As illustrated in FIGS. 65 and 65-1, one form of positioning and stabilizing structure 7000 may include headgear straps 7002 having a substantially X-shape. The positioning and stabilizing structure 7000 may include a rear strap or neck pad 7004, which is configured to contact a posterior portion of the patient's head. For example, the rear strap 7004 may overlay the patient's occipital bone and/or the trapezius muscle.

In some forms, the rear strap 7004 may be constructed from a stiff and/or at least partially rigid material. For example, the rear strap 7004 may be constructed from a stiff, laminate material, which may be unable to significantly stretch. The stiffness or rigidity may assist in anchoring the positioning and stabilizing structure to the posterior of the patient's head. Additionally, the material may be soft in order to maximize patient comfort.

With continued reference to FIGS. 65 and 65-1, four straps may extend from the rear strap 7004. A pair of upper straps 7008 may extend from a superior portion of the rear strap 7004, and a pair of lower straps 7012 may extend from an inferior portion of the rear strap 7004. In some forms, the pair of upper straps 7008 may be shorter than the pair of lower straps 7012. In other examples, they may be the same size, or the upper straps 7008 may be longer than the lower straps 7012.

Each strap 7008, 7012 may include a connector region 7016. In the illustrated example, the connector regions 7016 are hook tabs (e.g., Velcro), although other types of connections may be used (e.g., magnets, mechanical snaps, etc.). Each respective strap 7008, 7012 may be folded onto itself so that the connector region 7016 contacts a portion of the positioning and stabilizing structure 3300 (e.g., the same strap 7008, 7012). The straps 7008, 7012 may be constructed at least partially from a loop material that the hook tabs 7016 removably engage. The patient may removably select where to position each connector region 7016 in order to adjust the length of the respective strap, and therefore the sealing force applied by the seal-forming structure 3100.

In some forms, the pair of upper straps 7008 may be constructed from a stiff and/or at least partially rigid material. For example, the upper straps 7008 may be constructed from a stiff, laminate material, which may be unable to significantly stretch. In some forms, the rear strap 7004 and the upper straps 7008 may be constructed from the same material, although different materials may be used.

In some forms, the lower straps 7012 may be constructed from an elastic material. For example, the lower straps 7012 may be constructed from a high stretch laminate material, which may be capable of stretching.

As shown in FIG. 65, each upper and lower strap 7008, 7012 may be individually connected to the rear strap 7004. For example, each upper and lower strap 7008, 7012 may be independently stitched to the rear strap 7004. Some forms of the rear strap 7004 may include an X-shape so that the stitching of each strap 7008, 7012 are spaced apart from adjacent stitching. In other examples, different connection techniques may be used, like ultrasonic welding. In other examples, the upper straps 7008 may be integrally formed with the rear strap 7004 so that stitching or other connection techniques may not be necessary (e.g., because they are formed from the same material and may be cut from the same sheet of material).

As shown in FIG. 65-1, the rear strap 7004 may include more rounded edges than the rear strap 7004 of FIG. 65. This may allow the upper and lower strap 7008, 7012 on each side (e.g., the left side or the right side) to be more closely positioned relative to one another. A single, continuous stitch (or other connection technique) may be used to connect the left upper and lower straps 7008, 7012 to the rear strap 7004. Additionally, a single, continuous stitch (or other connection technique) may be used to connect the right upper and lower straps 7008, 7012 to the rear strap 7004. In some forms, the continuous stitch on each side may be curved and follow the perimeter of the rear strap 7004.

In the illustrated examples of FIGS. 65 and 65-1, the headgear straps 7002 may not include bottom straps and/or top straps. In other words, the headgear straps 7002 do not include straps that extend below the patient's chin (e.g., below the mental protuberance). The headgear straps 7002 also do not include straps that extend toward the crown of the patient's head (e.g., along the parietal bone toward the control plane). In other examples, the headgear straps 7002 may include top straps and/or bottom straps.

As shown in FIG. 66, the positioning and stabilizing structure 7000 may be used with the plenum chamber 3200. The illustrated plenum chamber 3200 is a full-face plenum chamber 3200, although the positioning and stabilizing structure 7000 could be used with a nasal plenum chamber 3200.

In some forms, the headgear straps 7002 may connect to the remainder of the patient interface 3000 in a substantially similar way as the straps in FIG. 57 (or any other previous example). For example, the hollow tubes 3334 may include at least one tab 3320 that can removably receive a portion of the headgear straps 7002. For example, each upper strap 7008 may be threaded through a tab 3320 in order to connect the headgear straps 7002 to the hollow tubes 3334. As described above, the upper straps 7008 may include connector regions 7016, which may be threaded through the tab 3320 and folded back in order to connect to the same upper strap 7008. The connector region 7016 may connect closer to the rear strap 7004 along the respective upper strap 7008 in order to shorten the length of the upper strap 7008 and provide a greater tensile force.

In some forms, the tabs 3320 of FIG. 66 may be more superior than the tabs 3320 in FIG. 55 or 57. In other words, the tabs 3320 in FIG. 66 may be disposed closer to the decoupling structure 3500 than the tabs 3320 in FIG. 55 or 57. As a result of the more superior tabs 3320, the upper straps 7008 may extend in the posterior direction parallel to the line $L_2$ that is tangent to a helix H of the patient's ear without the use of an extender 3358 (although the upper straps 7008 may also extend along a different line). This may allow the upper straps 7008 to produce the same force vector as the side portions 3350a, 3350b (e.g., directed along the angle measured from the axis AA) and be spaced apart from the patient's ears so that the likelihood of the upper straps 7008 intersecting either ear is significantly reduced. In other words, the upper straps 7008 may connect in a similar way to the side portion 3350a in FIG. 53, but the higher tab 3320 may allow for a smaller angle (i.e., more vertically directed force) without the upper straps 7008 contacting the patient's ear. Just like in FIG. 57, the patient may not have to tighten the upper straps 7008 as much when the angle θ is smaller (e.g., because a greater component of the force is directed in the superior-inferior direction so that the rear strap 7004 is pulled into the patient's occiput). This may promote patient comfort while wearing the headgear straps 7002 (e.g., because the tensile force is directly applied from the tabs 3320 without the use of the extender 3358).

With continued reference to FIG. 66, the lower straps 7012 may be connected to the plenum chamber 3200 in order to provide a posterior directed force vector for maintaining the seal-forming structure 3100 in the sealed position. As described above, the lower straps 7012 may be longer than the upper straps 7008 in order to reach from the posterior portion of the patient's head (e.g., where the rear strap 7004 rests) and the plenum chamber 3200. In the illustrated example, each lower strap 7012 may connect to a clip 7020 that directly connects to the plenum chamber 3200. In some forms, the clip 7020 may include a magnet to magnetically connect to the plenum chamber 3200 (although other types of connections, like mechanical fasteners, may be used). The lower straps 7012 may be threaded through the respective clips 7020 in a similar way as the upper straps 7008 are threaded through the tabs 3320. The connector regions 7016 of the lower straps 7012 may be selectively connected along the surface of the same lower strap 7012 in order to adjust the tensile force. The clips 7020 may be disconnected from the plenum chamber 3200 so that the headgear straps 7002 can be more easily removed from the patient's head without needed to alter the position of the connector regions 7016. In other examples, the lower straps 7012 may be permanently connected to the plenum chamber. The stetchable material of the lower straps 7012 may allow the headgear straps 7002 to be removed without disconnecting the lower straps 7012 (or the clips 7020) from the plenum chamber 3200.

In some forms, the angle of the upper straps 7008 and the absence of a connection strap (see e.g., FIG. 58) may allow the rear strap 7004 to sit higher on the patient's head (e.g., closer to the otobasion inferior). This may improve patient comfort because the lower straps 7012 may sit higher on the patient's face.

As shown in FIGS. 67 and 68, an alternate example of a positioning and stabilizing structure 8000 and headgear straps 8002 may be connected to the plenum chamber 3200. The headgear straps 8002 may be similar to the headgear straps 7002, and only some similarities and differences are described below.

As shown in FIG. 67, the headgear straps 8002 may include a rear strap 8004, which may be larger than the rear strap 7004. For example, the rear strap 8004 may include a central portion 8005 and a pair of lower portions 8006, which may be formed as dog legs. Thus, the rear strap 8004 may more closely approximate an X-shape than the rear-portion 7004 of FIG. 65. The shape may allow the rear strap 8004 to sit higher on the patient's head. For example, the central portion 8005 alone may be narrower than the rear strap 7004. The central portion 8005 may still contact the occipital bone, but may contact less of the trapezius muscle, which may decrease irritation and uncomfortableness during use. Additionally, the lower portions 8006 may extend around the sides of the patient's neck, which may disperse the load from a centralized location at the back of the patient's head (e.g., substantially on the trapezius muscle). The dog leg design of the lower portions 8006 may promote additional patient comfort.

As shown in FIG. 68, the hollow tubes 3334 may curve more rearward than the hollow tubes 3334 of FIG. 66. The tabs 3320 may be aligned with the apex axis AA. This allow the tabs 3334 to be lower on the hollow tubes 3334 (e.g., more inferior than the tabs 3320 of FIG. 66). Thus, upper straps 8008 may not need an extender 3358 in order to be positioned substantially parallel to the line $L_2$. The upper straps 8008 may be able to achieve the same force vector as the upper straps 7008 being more superior. Because the tabs 3320 are positioned more in the posterior direction, the upper straps 8008 may connect proximate or onto the rear strap 8004 (e.g., via connector regions, not shown).

The lower straps 8012 may extend from the lower portions 8006 and connect to the plenum chamber 3200 in a similar manner as described for the lower straps 7012. Tightening the lower straps 8012 may apply tension to the lower portions 8006, which may not be substantially in contact with a posterior portion of the patient's head (e.g., the lower portions 8006 may not substantially contact the patient's trapezius muscle). This may be beneficial for patient comfort because the dog legged shape of the lower portions 8006 may direct the force away from a sensitive area, while still providing the necessary retention and anchoring force.

In the illustrated examples of FIGS. 67 and 68, the headgear straps 8002 may not include bottom straps and/or top straps. In other words, the headgear straps 8002 do not include straps that extend below the patient's chin (e.g., below the mental protuberance). The headgear straps 8002 also do not include straps that extend toward the crown of the patient's head (e.g., along the parietal bone toward the control plane). In other examples, the headgear straps 8002 may include top straps and/or bottom straps.

As shown in FIGS. 69 and 70, an alternate example of a positioning and stabilizing structure 9000 and headgear straps 9002 may be connected to the plenum chamber 3200. The headgear straps 9002 may be similar to the headgear straps 7002, and only some similarities and differences are described below.

As shown in FIG. 69, the headgear straps 9002 may include a rear strap 9004 with a top portion 9005, a bottom portion 9006, and a pair of side portions 9007 that connect the top portion 9005 to the bottom portion 9006. The top portion 9005 may sit on the patient's head entirely above the trapezius muscle (e.g., entirely overlaying the occipital bone). The bottom portion 9006 may sit on the patient's head entirely below the occipital bone (e.g., overlaying the trapezius muscle). The side portions 9007 may be inclined or dog legged between the top and bottom portions 9005, 9006. In some forms, the top portion 9005 and/or the bottom portion 9006 may sit horizontally against the patient's head, and the side portions 9007 may have a larger radius relative to at least one of these straps than the radius of the lower portion 8006 relative to the central portion 8005 (see e.g., FIG. 67).

As shown in FIG. 70, the hollow tubes 3334 may curve more rearward than the hollow tubes 3334 of FIG. 66. The tabs 3320 may be aligned with the apex axis AA. This allow the tabs 3334 to be lower on the hollow tubes 3334 (e.g., more inferior than the tabs 3320 of FIG. 66). Thus, upper straps 9008 may not need an extender 3358 in order to be positioned substantially parallel to the line $L_2$. The upper straps 9008 may be able to achieve the same force vector as the upper straps 7008 being more superior. Because the tabs 3320 are positioned more in the posterior direction, the upper straps 9008 may connect proximate or onto the rear strap 9004 (e.g., via connector regions, not shown).

The lower straps 9012 may extend from the lower portion 9006 and connect to the plenum chamber 3200 in a similar manner as described for the lower straps 7012. Tightening the lower straps 9012 may apply tension to the lower portion 9006, which may assist in anchoring the lower portion 9006 to the posterior region of the patient's head. Tightening the upper straps 9008 may apply tension to the upper portion 9005, which may assist in anchoring the upper portion 9005 to the posterior region of the patient's head. Because the upper and lower portions 9005, 9006 are spaced apart from one another, the total force may be spread out along the posterior region of the patient's head, which may promote comfort.

In the illustrated examples of FIGS. 69 and 70, the headgear straps 9002 may not include bottom straps and/or top straps. In other words, the headgear straps 9002 do not include straps that extend below the patient's chin (e.g., below the mental protuberance). The headgear straps 9002 also do not include straps that extend toward the crown of the patient's head (e.g., along the parietal bone toward the control plane). In other example, the headgear straps 9002 may include either top straps or bottom straps.

As shown in FIGS. 71 and 72, an alternate example of a positioning and stabilizing structure 10000 and headgear straps 10002 may be connected to the plenum chamber 3200. The headgear straps 10002 may be similar to the headgear straps 7002, and only some similarities and differences are described below.

As shown in FIG. 71, the headgear straps 10002 may include a rear strap 10004 with a central portion 10005 and a pair of side portions 10006 connected the central portion 10005. The central portion 10005 may include a larger surface area than the rear strap 7004 and may sit higher on the patient's head (e.g., may overlay little to none of the trapezius muscle). The side portions 10006 may extend in a lateral and interior direction from the central portion 10005, and may not substantially overlay the trapezius muscle.

In some forms, the central portion 10005 may include openings or slots 10024. The slots 10024 may be disposed proximate an outer perimeter of the central portion 10005. The slots 10024 may also be disposed proximate to a superior end of the central portion 10005.

As shown in FIG. 72, upper straps 10008 may be integrally formed with the hollow tubes 3334. In other words, the hollow tubes 3334 may not include tabs 3320, and the upper straps 10008 may be directly connected to the hollow tubes 3334 approximately where the tabs could be.

As shown in FIG. 72, the upper straps 10008 may be formed from a rigid material and may include a similar shape as an extender (see e.g., extenders 3358a, 3358b in FIG. 56). For example, each upper strap 10008 may include a substantially horizontal portion 10028 and an inclined portion 10032, which may be included at substantially the same angle as the inclined portion 3360. The upper straps 10008 may therefore extend substantially parallel to line $L_2$, and may provide a force along substantially the same vector. In other examples, the upper straps 10008 may be removably connected to the hollow tubes 3334 (e.g., like in FIG. 57).

Returning to FIG. 71, the upper straps 10008 may be removably connected to the rear strap 10004. For example, the upper straps 10008 may be connected to the central portion 10005 through the slots 10024. Each upper strap 10008 may be threaded through the respective slot 10024, and may be folded over itself in order to adjust its length and the applied tension.

The lower straps 10012 may extend from the lower portions 10006 and connect to the plenum chamber 3200 in a similar manner as described for the lower straps 7012. Tightening the lower straps 10012 may apply tension to the lower portions 10006, which may not be substantially in contact with a posterior portion of the patient's head (e.g., the lower portions 10006 may not substantially contact the patient's trapezius muscle). This may be beneficial for patient comfort because the dog legged shape of the lower portions 10006 may direct the force away from a sensitive area, while still providing the necessary retention and anchoring force. Additionally, the superior sitting central portion 10005 (e.g., having substantially no overlap with the trapezius muscle) may further reduce the load on the nape of the patient's neck, which may result in improved patient comfort.

In the illustrated examples of FIGS. 71 and 72, the headgear straps 10002 may not include bottom straps and/or top straps. In other words, the headgear straps 10002 do not include straps that extend below the patient's chin (e.g., below the mental protuberance). The headgear straps 10002 also do not include straps that extend toward the crown of the patient's head (e.g., along the parietal bone toward the control plane). In other examples, the headgear straps 10002 may include top straps and/or bottom straps.

As shown in FIGS. 73 and 74, an alternate example of a positioning and stabilizing structure 11000 and headgear straps 11002 may be connected to the plenum chamber 3200. The headgear straps 11002 may be similar to the headgear straps 7002, and only some similarities and differences are described below.

As shown in FIG. 73, the headgear straps 11002 may include a rear strap 11004 which may include a larger surface area than the rear strap 7004 and may sit higher on the patient's head (e.g., may overlay little to none of the trapezius muscle). For example, the rear strap 11004 may sit at approximately the same height as the rear strap 10004.

As shown in FIG. 74, the hollow tubes 3334 may curve more rearward than the hollow tubes 3334 of FIG. 66. This may dispose the tabs 3320 more posterior than the tabs 3320 of FIG. 66. Additionally, the hollow tubes 3334 may not curve as much in the rearward direction as the hollow tubes 3334 of FIG. 70. This may dispose the tabs 3320 more anterior than the tabs 3320 of FIG. 70. Based on this positioning, the upper straps 11008 connected to the tabs 3320 may extend along an angle greater than the angle θ. For example, the upper straps 11008 may extend along the angle φ, or may extend along a different angle. The upper straps 11008 may still extend along an angle that will not intersect the patient's ears and cause discomfort.

As shown in FIGS. 73 and 74, lower straps 11012 may be connected to the rear strap 11004 and the plenum chamber 3200 using a similar technique as described above. In some forms, the lower straps 11012 may be a single strap connected inferior to the rear strap 11004. The lower strap 11012 may be long enough to extend from one side of the plenum chamber 3200, around a patient's head, and to the other side of the plenum chamber 3200.

In some forms, the headgear straps 11002 may include top straps 11036, which may extend over the crown of the patient's head. For example, each top strap 11036 may overlay the parietal bone. The top straps 11036 may be fixed to the rear strap 11004 (e.g., via stitching, ultrasonic welding, being integrally formed, etc.), and may removably connected to the hollow tubes 3334 proximate to the decoupling structure 3500 using tabs (not shown) similar to tabs 3320.

In use, the patient may be able to adjust three sets of force vectors, which may provide the patient with more control to adjust the headgear straps 11002 to their specific head. Additionally, the various force vectors created by adjusting the headgear strap 11002 may allow the rear strap 11004 to sit higher on the patient's head (e.g., in order to overlay less of the trapezius muscle), which may improve patient comfort. Raising the rear strap 11004 may also raise the lower straps 11012 (or lower strap 11012), which may also improve patient comfort.

In the illustrated examples of FIGS. 73 and 74, the headgear straps 11002 may not include bottom straps. In other words, the headgear straps 11002 do not include straps that extend below the patient's chin (e.g., below the mental protuberance). In other examples, the headgear straps 11002 may include bottom straps and/or may not include top straps 11036.

As shown in FIGS. 75-76, an alternate example of a positioning and stabilizing structure 12000 and headgear straps 12002 may be connected to the plenum chamber 3200. The headgear straps 12002 may be similar to the headgear straps 7002, and only some similarities and differences are described below.

As shown in FIG. 75, the headgear straps 12002 may include a rear strap 12004 which may include a larger surface area than the rear strap 7004. The rear strap 12004 may include a substantially triangular shape. In some forms, the superior end of the rear strap 12004 may sit substantially horizontally against the patient's head, and may converge toward a point at the inferior end.

In some forms, the rear strap 12004 may be constructed from an elastic or stretchy material. For example, the rear strap 12004 may be constructed from a textile material that can elastically deform. The textile material may be soft and/or promote patient comfort. The rear strap 12004 may be under tension (e.g., pre-tensioned) before being donned by the patient. This may assist the rear strap 12004 in sitting higher on the patient's head. For example, the rear strap 12004 may overlay the occipital bone and may not substantially contact the trapezius muscle.

In some forms, the inferior portion of the rear strap 12004 may converge at an angle α between approximately 1° and approximately 180°. In some forms, the inferior portion of the rear strap 12004 may converge at an angle α between approximately 50° and approximately 175°. In some forms, the inferior portion of the rear strap 12004 may converge at an angle α between approximately 90° and approximately 160°. In some forms, the inferior portion of the rear strap 12004 may converge at an angle α between approximately 110° and approximately 150°. In some forms, the inferior portion of the rear strap 12004 may converge at an angle α between approximately 120° and approximately 140°. In some forms, the inferior portion of the rear strap 12004 may converge at an angle α that is approximately 130°.

With continued reference to FIG. 75, the headgear straps 12002 may include a pair of upper straps 12008. In the illustrated example, the upper straps may be connected to the rear strap 12004, and may be constructed from a different material than the rear strap 12004. For example, the pair of upper straps 12008 may be constructed from a stiffened or semi-rigidized material. The upper straps 12008 may include a rigid or semi-rigid material covered with a textile material, or a textile material used to construct the upper straps 12008 may be rigidized or stiffened so that it less extensible than the rear strap 12004.

In some forms, the upper straps 12008 may be connected to the rear strap 12004 using one of the connection techniques described above. For example, the upper straps 12008 may be stitched to the rear strap along the surfaces forming the angle α. In other words, at least a portion of the upper straps 12008 may be more inferior on the patient's head than the rear strap 12004. The increased stiffness of the upper straps 12008 (e.g., compared to the rear strap 12004) may assist in limiting the rear strap 12004 (or the headgear straps 12002 as a whole) from pulling down.

In certain forms, the upper straps 12008 may be connected to one another proximate to the vertex of angle α. In other forms, the upper straps 12008 may be formed from a single piece of material so that the pair of upper straps 12008 are not joined together.

In some forms, the upper straps 12008 may converge at an angle β between approximately 1° and approximately 180°. In some forms, the upper straps 12008 may converge at an angle β between approximately 50° and approximately 175°. In some forms, the upper straps 12008 may converge at an angle β between approximately 90° and approximately 170°. In some forms, the upper straps 12008 may converge at an angle β between approximately 110° and approximately 165°. In some forms, the upper straps 12008 may converge at an angle β between approximately 140° and approximately 160°. In some forms, the upper straps 12008 may converge at an angle β that is approximately 150°. For example, the upper straps 12008 may be positioned so that the angle β is larger than the angle α, although in other examples the angle β and the angle α may be substantially equal.

With continued reference to FIG. 75, the headgear straps 12004 may include a pair of lower straps 12012. In the illustrated example, the lower straps 12012 may be connected to the upper straps 12008 and may be constructed from a different material than the upper straps 12008. For example, the pair of lower straps 12012 may be constructed from an elastic or stretchable material (e.g., the same material as the rear strap 12004). The lower straps 12012 may include a textile material. The lower straps 12012 may be under tension (e.g., pre-tensioned) before being worn by the patient (e.g., similar to the rear strap 12004).

In some forms, the stretchability of the lower straps 12012 may improve patient comfort by conforming to the patient's face during dynamic movements (e.g., turning the head from side to side).

In some forms, the upper straps 12008 may be connected to the lower straps 12012 using one of the connection techniques described above. For example, the lower straps 12012 may be stitched to the upper straps 12008 along the surfaces forming the angle β. In other words, at least a portion of the lower straps 12012 may be more inferior on the patient's head than the upper straps 12008. The pre-tension of the lower straps 12012 may assist in limiting the upper straps 12008 (or the headgear straps 12002 as a whole) from pulling down.

In some forms, the upper strap 12008 and the lower strap 12012 on the same side of the headgear straps 12002 (e.g., the left or right) may be angled relative to one another. In some forms, the angle ψ may be between approximately 1° and approximately 90°. In some forms, the angle ψ may be between approximately 10° and approximately 80°. In some forms, the angle ψ may be between approximately 25° and approximately 75°. In some forms, the angle ψ may be between approximately 40° and approximately 60°. In some forms, the angle ψ may be approximately 50°.

As shown in FIG. 75-1, an alternate version of the headgear straps 12002-1 may be used with the patient interface 3000. The headgear straps 12002-1 may be substantially similar to the headgear straps 12002.

In some forms, the rear strap 12004-1 may be constructed from a stiffened or rigid material, which may be the same as the material of the upper straps 12008-1. The upper straps 12008-1 and the rear strap 12004-1 may be connected together using one of the above listed techniques, or may be formed together as a single piece.

The lower straps 12012-1 may be connected to the upper straps 14008-1 in a similar way as the as the upper straps 12008 are connected to the lower straps 12012. In the illustrated example, the lower straps 12012-1 may also be constructed from an elastic or stretchable material.

In some forms, the upper strap 12008-1 and the lower strap 12012-1 on the same side of the headgear straps 12002-1 (e.g., the left or right) may be angled relative to one another. In some forms, the angle ω may be between approximately 1° and approximately 90°. In some forms, the angle ω may be between approximately 10° and approximately 80°. In some forms, the angle ω may be between approximately 25° and approximately 75°. In some forms, the angle ω may be between approximately 30° and approximately 50°. In some forms, the angle ω may be approximately 40°.

As shown in FIG. 76, the hollow tubes 3334 may curve more rearward than the hollow tubes 3334 of FIG. 66. The tabs 3320 may be aligned with the apex axis AA. This allow the tabs 3334 to be lower on the hollow tubes 3334 (e.g., more inferior than the tabs 3320 of FIG. 66). Thus, upper straps 14008 may not need an extender 3358 in order to be positioned substantially parallel to the line $L_2$. The upper straps 14008 may be able to achieve the same force vector as the upper straps 7008 being more superior. Because the tabs 3320 are positioned more in the posterior direction, the upper straps 14008 may connect proximate or onto the rear strap 14004 (e.g., via connector regions, not shown).

The lower straps 12012 may connect to the plenum chamber 3200 in a similar manner as described for the lower straps 7012. Tightening the lower straps 12012 may apply tension to the lower straps 12012, and therefore the rear strap 14004.

The shape of the headgear straps 14002 may promote patient comfort because the straps rest higher on the patient's head. For example, the rear strap 14004 may rest on the occipital bone, and the large surface area may help to secure the rear strap to the patient's head. Additionally, the angle β of the upper straps 14008 may assist in anchoring the headgear straps 14002 to the patient's head (e.g., because of the material and its location), while not providing uncomfortable pressure on the patient's neck.

In the illustrated examples of FIGS. 75-76, the headgear straps 12002 may not include bottom straps and/or top straps. In other words, the headgear straps 12002 do not include straps that extend below the patient's chin (e.g., below the mental protuberance). The headgear straps 12002 also do not include straps that extend toward the crown of the patient's head (e.g., along the parietal bone toward the control plane). In other examples, the headgear straps 12002 may include top straps and/or bottom straps.

5.3.3.4 Removable Straps

As shown in FIG. 77, the positioning and stabilizing structure 13000 may include removable arms 13004. The removable arms 13004 may be constructed from a rigid material or a semi-rigid material (e.g., plastic) in order to maintain its shape. In some forms, a patient may slightly bend the arm 13004 in order to adjust its angle.

The arm 13004 may include a first end with a clip 13008, which may be biased toward a closed position. The patient may pull the clip 13008 to provide sufficient space to fit around the tab 3320 of the hollow tube 3334. The clip 13008 may then return to its biased position in order to clap against the tab 3320 and secure the arm 13004 to the hollow tub 3334.

In some forms, the clip 13008 may be smaller than the tab 3320. This may allow the clip 13008 to move within the tab 3320, while remaining connected to the tab 3320. The clip 13008 may also rotate within the tab 3320 as a result of the application of tension. The position and/or angle within the tab 3320 may depend on the size of the patient's head, which may allow the arm 13004 to be used with different sized patients.

In certain forms, the clip 13008 may have a range of translational motion between approximately 1 mm and approximately 1000 mm. In certain forms, the clip 13008 may have a range of translational motion between approximately 5 mm and approximately 100 mm. In certain forms, the clip 13008 may have a range of translational motion between approximately 10 mm and approximately 75 mm. In certain forms, the clip 13008 may have a range of translational motion between approximately 30 mm and approximately 50 mm.

A second end of the arm 13004, opposite the clip 13008, may include a loop 13012. A strap (e.g., a lower strap, not shown) may be threaded through the loop 13012 and adjusted to change the tension. The strap may be a single strap that extends between both arms 13004, or may be a pair of straps connected to a rear strap. For example, the strap may be similar to the rear strap 3304 of FIG. 56.

In some forms, the loop 13012 may be curved and may be wider than the strap. This may allow the strap to slide within the loop 13012 and adjust to an ideal position for a given patient. In this way, the clip 13008 and the loop 13012 of each arm 13004 may allow for slight adjustments so that the positioning and stabilizing structure 13000 may better fit an individual patient, thereby promoting comfort and patient compliance.

In some forms, the arm 13004 may be inclined between the clip 13008 and the loop 13012. For example, the arms 13004 may be shaped similarly to the extenders 3358*a*, 3358*b* of FIG. 56. In some forms, the clip 13008 may be connected to the hollow tube 3334 substantially parallel to the Frankfort horizontal, while in use. The arm 13004 may incline so that the loop 13012 is angled approximately 30° with respect to the Frankfort horizontal.

In some forms, the arms 13004 may include at least one bendable section 13038. A patient may adjust internal arm angles but moving one or more of the bendable sections 13038. The bendable sections 13038 may allow patient to customize the shape of each arm 13004 in order to better fit an individual patient.

In some forms, the arm 13004 may be covered with a soft material in order to further promote patient comfort. For example, a textile sleeve (not shown), may be positioned around the arm 13004. The sleeve may sleeve the clip 13008 and the loop 13012 exposed. The sleeve may also be either removable or permanently connected to the arm 13004.

As shown in FIGS. 78 and 79, the arm 13004 may contact a side of the patient's head, and may extend beyond the patient's ears. This may help reduce likelihood that any strap contacts the patient's ear and causes irritation. The arm 13004 may be connected to the side portion 3350*a* and the pad 3354, which may anchor the patient interface 3000 to the patient's head as described above. The arms 13004 may be used with either a nasal cushion (see e.g., FIG. 78) or a full-face cushion (see e.g., FIG. 79). In other examples, the arms 13004 may be used without the side portion 3350*a* and the pad 3354.

In the illustrated example of FIGS. 78 and 79, the patient interface 3000 may not include lower straps. In other words, the patient interface 3000 may not include straps that extend along the patient's cheek (e.g., over the masseter muscle) and between the pad 3354 and/or side portion 3350 and the plenum chamber 3200. In other examples, the patient interface 3000 may include lower straps.

In the illustrated examples of FIGS. 78 and 79, the patient interface 3000 may not include bottom straps and/or top straps. In other words, the patient interface 3000 may not include straps that extend below the patient's chin (e.g., below the mental protuberance). The patient interface 3000 also may not include straps that extend toward the crown of the patient's head (e.g., along the parietal bone toward the control plane). In other examples, the patient interface 3000 may include top straps and/or bottom straps.

As shown in FIGS. 80-82, an alternate form of a positioning and stabilizing structure 14000 may include removable arms 14004. The removable arms 14004 may be constructed from a rigid material or a semi-rigid material (e.g., plastic) in order to maintain its shape. In some forms, a patient may slightly bend the arm 14004 in order to adjust its angle. The arms 14004 may be substantially similar to the arms 13004, and only some similarities and differences are described below.

As shown in FIGS. 80 and 80-1, the first end of the arm 14004 may include a clip 14008, which may removably connect to a tab 3320 of the hollow tubes 3334. Like the clip 13008 in FIG. 77, the clip 14008 in FIG. 78 may include a locked position when the clip 14008 will clamp down on the tab 3320. Unlike the clip 13008, the clip 14008 may be rotatable relative to the rest of the arm 14004. For example, the first end of the arm 14008 may include a post 14009. The clip 14008 may be coupled to the post 14009 and may be rotatable relative to the post 14009. In some forms, the clip 14008 may be freely rotatable about the post 14009. In some forms, the clip 14008 may be biased toward the locked position and may have to overcome the bias to rotate toward an open position.

In some forms, the arm 14004 may include a lock 14010 disposed proximate to the first end. The lock 14010 may include a protrusion 14011 that selectively contacts the clip 14008. The protrusion 14011 may limit rotation of the clip 14008 about the post 14009. For example, the patient may engage the protrusion 14011 with the clip 14008 when the arm 14004 is connected to the tab 3320. This may limit the rotational movement of the clip 14008 about the post 14009, and limit the occurrence of the clip 14008 accidentally disengaging (e.g., while the patient is sleeping) from the tab 3320. The patient may manually move the protrusion 14011 and/or the clip 14008 so that the two are no longer in contact. This may allow the clip 14008 to more freely move so that the patient can disconnect the arm 14004 from the hollow tube 3334 (e.g., and use a different positioning and stabilizing structure).

As shown in FIG. 81, the lock 14010 may be formed as one piece with the post 14009 and/or the clip 14008. For example, the lock 14010 may be overmolded with either the post 14009 and/or the clip 14008, so that the lock 14010 is not completely separable from the arm 14004. In other examples, the lock 14010 may be connected to the post 14009 and/or the clip using a fastener (e.g., a mechanical fastener). For example, the post 14009 and the lock 14010 may be formed together and connected to the arm 14004. They may allow rotation of the clip 14008 about the post while also limiting the total movement of the clip 14008.

With continued reference to FIG. 81, the arm 14004 may curve between the first end and a second end. Unlike the second end of the arm 13004 that includes a loop 13012, the second end of the arm 14004 may include a tapered end 14012. The tapered end 14012 may have a curved surface and may have a smaller width than the remainder of the arm 14012.

In some forms, the arm 14004 may be resemble the arms of eyeglasses. For example, the arms 14004 may contact the patient's head superior to the patient's ears, and may curve around the patient's ears in the inferior and posterior direction. The arms 14004 may remain on the side of the patient's head, and my not extend to a posterior region of the patient's head (e.g., may not overlay the occipital bone or the trapezius muscle).

As shown in FIG. 82, a sleeve 14040 may be connected to the arm 14004. The tapered end 14012 of the arm 14004 may be inserted into the sleeve 14040. The curvature and tapering of the arm 14040 may assist in sliding the sleeve 14040 along the length of the arm 14004 in order to limit bunching or snagging of the sleeve 14040. In some examples, the sleeve 14040 may be constructed from a comfortable and/or compliant material so that it can adjust to the shape of the arm 14004. This material may be a textile, which may be comfortable against the patient's face.

As shown in FIGS. 83 and 84, the arm 14004 may contact a side of the patient's head, and may extend beyond the patient's ears. The arms 14004 may rest against the patient's head like eyeglasses. The arms 14004 may be usable without the need for additional straps (e.g., top straps, bottom straps, lower straps, upper straps, etc.) and may be able to support the seal-forming structure 3100 in a sealing position. The arms 14004 may be used with either a nasal cushion (see e.g., FIG. 83) or a full-face cushion (see e.g., FIG. 84). In other examples, the arms 14004 may be used with any combination of straps described above.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes 3404, for example, about 20 to about 80 holes 3404, or about 40 to about 60 holes 3404, or about 45 to about 55 holes 3404.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure 3500, for example, a swivel or a ball and socket.

As shown in FIG. 46, the decoupling structure 3500 is inserted through the first inlet port 3208. The decoupling structure 3500 retains the flap 3338 in the open position, and prevents the flap 3338 from moving to the closed position.

In certain forms, the decoupling structure 3500 is moveable from the first inlet port 3208 to a third inlet port 3209 on the plenum chamber 3200 that is spaced apart from the first inlet port 3208. The flap 3207 of the first inlet port 3208 is then free to move. For example, when pressurized air is supplied through the decoupling structure 3500 and the second inlet port 3336, the force of the air is greater than the bias (e.g., mechanical, magnetic, etc.) of the flap 3207. The flap 3207 moves to the closed position and substantially prevents air from escaping through the first inlet port 3208. Unlike the second inlet port 3336, the third inlet port 3209 does not include a flap.

5.3.6 Plug

As shown in FIG. 46, one form of the patient interface 3000 includes a plug 3550. The plug 3550 is inserted through one of the ports 3208, 3336 to substantially prevent airflow through the port 3208, 3336. For example, the plug 3550 may be coupled to the port 3208, 3336 when not receiving the decoupling structure 3500.

In certain forms, the plug 3550 may be used with ports 3208, 3336 that include a valve 3206, 3339. The plug 3550 retains the valve 3206, 3339 in the open position, while providing the seal itself.

5.3.7 Connection Port

Connection port 3600 allows for connection to the air circuit 4170.

5.3.8 Forehead Support

In one form, the patient interface 3000 includes a forehead support 3700. In another form, the patient interface 3000 does not include a forehead support 3700.

5.3.9 Anti-Asphyxia Valve

In one form, the patient interface 3000 includes an anti-asphyxia valve. (AAV) (e.g., flap 3207 and flap 3338).

As shown in FIG. 46, certain forms of the flap 3207, 3338 proximate the first and/or second ports 3208, 3336 respectively act as AAV 3206, 3339 when a decoupling structure 3500 is not coupled to the respective port 3208, 3336. The decoupling structure 3500 may include an additional AAV 3206, 3339 to allow airflow through the port that the decoupling structure 3500 is coupled to.

In certain forms, an AAV (not shown) may be included on the decoupling structure 3500 and either the plenum chamber 3200 or the positioning and stabilizing structure 3300 may not include the respective flap 3207, 3338 (see e.g., FIG. 47a). The plug 3550 is inserted into the port 3208, 3336 that does not include the decoupling structure 3500.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to pressurize a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010. The external housing 4010 may be formed in two parts, an upper portion 4012 and a lower portion 4014. Furthermore, the external housing 4010 may include one or more panel(s) 4015. The RPT device 4000 may comprise a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124, and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016. The pneumatic block 4020 may include one or more pneumatic components 4100.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas 4180, e.g. oxygen, is delivered to one or more points in the pneumatic path, such as upstream of the pneumatic block 4020, to the air circuit 4170, and/or to the patient interface 3000.

5.6 Humidifier

5.6.1 Humidifier Overview

In one form of the present technology there is provided a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir, a humidifier inlet to receive a flow of air, and a humidifier outlet to deliver a humidified flow of air. In some forms, an inlet and an outlet of the humidifier reservoir may be the humidifier inlet and the humidifier outlet respectively. The humidifier 5000 may further comprise a humidifier base, which may be adapted to receive the humidifier reservoir and comprise a heating element.

5.7 Breathing Waveforms

FIG. 42 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak−0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g., atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g., the humidity in the room where a patient is sleeping. Such ambient humidity may be different to the humidity outside the room where a patient is sleeping.

In another example, ambient pressure may be the pressure immediately surrounding or external to the body.

In certain forms, ambient noise (e.g., acoustic) may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g., from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC® (included in the range of products sold under this trademark), manufactured by DuPont. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

Textile: A flexible material made from interlaced fibers using techniques that include, but are not limited to weaving, knitting, crocheting, or braiding. Specific types of textiles may include fabrics, which are produced specific techniques (e.g., weaving and knitting).

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Anatomy 5.8.3.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.8.3.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g., about 360 degrees. In certain forms an elbow may be removable from a mating component, e.g., via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g., outer) surface, and a separate non-face-contacting (e.g., underside or inner) surface. In another example, a structure may comprise a first surface and a second surface.

To facilitate describing the shape of the three-dimensional structures and the surfaces, we first consider a cross-section through a surface of the structure at a point, p. See FIG. 17 to FIG. 21, which illustrate examples of cross-sections at point p on a surface, and the resulting plane curves. FIGS. 17 to 21 also illustrate an outward normal vector at p. The outward normal vector at p points away from the surface. In some examples we describe the surface from the point of view of an imaginary small person standing upright on the surface.

5.8.5.1 Curvature in One Dimension

The curvature of a plane curve at p may be described as having a sign (e.g., positive, negative) and a magnitude (e.g., 1/radius of a circle that just touches the curve at p).

Positive curvature: If the curve at p turns towards the outward normal, the curvature at that point will be taken to be positive (if the imaginary small person leaves the point p they must walk uphill). See FIG. 17 (relatively large positive curvature compared to FIG. 18) and FIG. 18 (relatively small positive curvature compared to FIG. 17). Such curves are often referred to as concave.

Zero curvature: If the curve at p is a straight line, the curvature will be taken to be zero (if the imaginary small person leaves the point p, they can walk on a level, neither up nor down). See FIG. 19.

Negative curvature: If the curve at p turns away from the outward normal, the curvature in that direction at that point will be taken to be negative (if the imaginary small person leaves the point p they must walk downhill). See FIG. 20 (relatively small negative curvature compared to FIG. 21) and FIG. 21 (relatively large negative curvature compared to FIG. 20). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g., relatively small. The plane curves in FIGS. 17 to 21 could be examples of such multiple cross-sections at a particular point.

Principal curvatures and directions: The directions of the normal planes where the curvature of the curve takes its maximum and minimum values are called the principal directions. In the examples of FIG. 17 to FIG. 21, the maximum curvature occurs in FIG. 17, and the minimum occurs in FIG. 21, hence FIG. 17 and FIG. 21 are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g., both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 32. A typical human right ear comprises a helix, which is a right-hand helix, see FIG. 33. FIG. 34 shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g., FIG. 31), or alternatively by a left-hand rule (FIG. 30).

Osculating plane: The plane containing the unit tangent vector and the unit principal normal vector. See FIGS. 30 and 31.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g., a gently sloping helical path). A space curve which deviates a relatively large amount from the osculating plane will have a relatively large magnitude of torsion (e.g., a steeply sloping helical path). With reference to FIG. 34, since T2>T1, the magnitude of the torsion near the top coils of the helix of FIG. 34 is greater than the magnitude of the torsion of the bottom coils of the helix of FIG. 34

With reference to the right-hand rule of FIG. 31, a space curve turning towards the direction of the right-hand binormal may be considered as having a right-hand positive torsion (e.g., a right-hand helix as shown in FIG. 34). A space curve turning away from the direction of the right-hand binormal may be considered as having a right-hand negative torsion (e.g., a left-hand helix).

Equivalently, and with reference to a left-hand rule (see FIG. 30), a space curve turning towards the direction of the left-hand binormal may be considered as having a left-hand positive torsion (e.g., a left-hand helix). Hence left-hand positive is equivalent to right-hand negative. See FIG. 35.

5.8.5.4 Holes

A surface may have a one-dimensional hole, e.g. a hole bounded by a plane curve or by a space curve. Thin structures (e.g., a membrane) with a hole, may be described as having a one-dimensional hole. See for example the one dimensional hole in the surface of structure shown in FIG. 24, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 27 and the example cross-sections therethrough in FIG. 28 and FIG. 29, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 26, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means +/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 Reference Signs List

| | |
|---|---|
| patient | 1000 |
| bed partner | 1100 |
| patient interface | 3000 |
| seal-forming structure | 3100 |
| nose mask | 3100a |
| mouth seal | 3100b |
| textile material | 3101 |
| hollow sealing tube | 3104 |
| holes | 3108 |
| retention mechanism | 3112 |
| first magnetic portion | 3114 |
| first clip structure | 3116 |
| first clip | 3116a |
| second clip | 3116b |
| gasket | 3116c |
| detachment mechanism | 3118 |
| inner surface | 3130 |
| insert | 3134 |
| magnetic thread | 3140 |
| magnetic thread | 3142 |
| tab | 3144 |
| recess | 3146 |
| nose opening | 3152a |
| mouth opening | 3152b |
| plenum chamber | 3200 |
| textile cover | 3204 |
| outer surface | 3204a |
| valve | 3206 |
| flap | 3207 |
| first inlet port | 3208 |
| third inlet port | 3209 |

| | |
|---|---|
| second magnetic portion | 3210 |
| third magnetic portion | 3212 |
| second clip structure | 3216 |
| first end | 3240 |
| second end | 3241 |
| conduit | 3242 |
| positioning and stabilizing structure | 3300 |
| side strap | 3302 |
| side strap | 3302b |
| rear strap | 3304 |
| top strap | 3306 |
| seal end | 3308 |
| first magnetic section | 3316 |
| second magnetic section | 3318 |
| tab | 3320 |
| headgear | 3324 |
| ear pieces | 3326 |
| transition | 3328 |
| hollow tubes | 3334 |
| connector | 3335 |
| second inlet port | 3336 |
| flap | 3338 |
| valve | 3339 |
| inner surface | 3342 |
| intermediate section | 3346 |
| first material | 3348 |
| second material | 3349 |
| side portion | 3350 |
| left side portion | 3350a |
| right side portion | 3350b |
| pad | 3354 |
| left side portion | 3354a |
| right second section | 3354b |
| extenders | 3358 |
| left extender | 3358a |
| right extender | 3358b |
| horizontal portion | 3359 |
| inclined portion | 3360 |
| third material | 3361 |
| connection strap | 3362 |
| first engagement section | 3366 |
| second engagement section | 3368 |
| buckle | 3370 |
| aperture | 3374 |
| projection | 3378 |
| loop | 3380 |
| vent | 3400 |
| holes | 3404 |
| decoupling structure | 3500 |
| plug | 3550 |
| connection port | 3600 |
| forehead support | 3700 |
| ISO | 3744 |
| RPT device | 4000 |
| external housing | 4010 |
| upper portion | 4012 |
| portion | 4014 |
| panels | 4015 |
| chassis | 4016 |
| handle | 4018 |
| pneumatic block | 4020 |
| pneumatic components | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| supplementary gas | 4180 |
| electrical components | 4200 |
| PCBA | 4202 |
| electrical power supply | 4210 |
| input devices | 4220 |
| central controller | 4230 |
| transducer | 4270 |
| humidifier | 5000 |
| positioning and stabilizing structure | 7000 |
| headgear straps | 7002 |
| rear strap | 7004 |
| upper strap | 7008 |
| lower strap | 7012 |
| connector region | 7016 |
| clip | 7020 |
| positioning and stabilizing structure | 8000 |
| headgear straps | 8002 |
| rear strap | 8004 |
| central portion | 8005 |
| lower portion | 8006 |
| upper strap | 8008 |
| lower strap | 8012 |
| connector region | 8016 |
| clip | 8020 |
| positioning and stabilizing structure | 9000 |
| headgear straps | 9002 |
| rear strap | 9004 |
| top portion | 9005 |
| bottom portion | 9006 |
| side portion | 9007 |
| upper strap | 9008 |
| lower strap | 9012 |
| connector region | 9016 |
| clip | 9020 |
| positioning and stabilizing structure | 10000 |
| headgear straps | 10002 |
| rear strap | 10004 |
| central portion | 10005 |
| side portion | 10006 |
| upper strap | 10008 |
| lower strap | 10012 |
| connector region | 10016 |
| clip | 10020 |
| slot | 10024 |
| positioning and stabilizing structure | 11000 |
| headgear straps | 11002 |
| rear strap | 11004 |
| upper strap | 11008 |
| lower strap | 11012 |
| connector region | 11016 |
| clip | 11020 |
| top strap | 11036 |
| positioning and stabilizing structure | 12000 |
| headgear straps | 12002 |
| rear strap | 12004 |
| upper strap | 12008 |
| lower strap | 12012 |
| connector region | 12016 |
| clip | 12020 |
| positioning and stabilizing structure | 12000-1 |
| headgear straps | 12002-1 |
| rear strap | 12004-1 |
| upper strap | 12008-1 |
| lower strap | 12012-1 |
| connector region | 12016-1 |
| clip | 12020-1 |
| positioning and stabilizing structure | 13000 |
| removable arm | 13004 |
| clip | 13008 |
| loop | 13012 |
| bendable section | 13038 |
| positioning and stabilizing structure | 14000 |
| removable arm | 14004 |
| clip | 14008 |
| post | 14009 |
| lock | 14010 |
| protrusion | 14011 |
| tapered end | 14012 |
| sleeve | 14040 |

What is claimed is:

1. A patient interface comprising:
a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;

a seal-forming structure constructed and arranged to form a seal with a region of a patient's face surrounding an entrance to a patient's airways for sealed delivery of a flow of air at the therapeutic pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use;

a positioning and stabilizing structure to provide a force to hold a seal-forming structure in a therapeutically effective position on a patient's head, the positioning and stabilizing structure comprising:

a gas delivery tube formed as a continuous structure to receive the flow of air from a connection port on top of the patient's head and to deliver the flow of air to the entrance of the patient's airways via the seal-forming structure, the gas delivery tube including a pair of tabs constructed and arranged to contact, in use, at least a region of the patient's head superior to an otobasion superior of the patient's head, wherein each tab of the pair of tabs having an opening with an opening length;

a pair of removable arms removably coupled to the tabs, each removable arm constructed and arranged, in use, to extend in a posterior and inferior direction, each removable arm comprising:

a first end including a clip configured to be removable from one tab of the pair of tabs, wherein the clip includes a clip length that is less than the opening length, wherein the clip is configured to move along the clip length and/or pivot within the opening in order to adjust a force vector, and a second end opposite to the first end; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breathe from ambient through their mouth in the absence of a flow of pressurised air through the plenum chamber inlet port, or the patient interface is configured to leave the patient's mouth uncovered; and wherein each removable arm of the pair of removable arms includes at least one bendable segment configured to allow positional adjustment between the first end and the second end to impart adjustment of a force vector, and wherein each bendable segment includes a plurality of bendable sections that are independently adjustable to adjust internal arm angles by moving one or more of the plurality of bendable sections.

2. The patient interface of claim 1, further comprising a rear strap connected to the second end of each removable arm of the pair of removable arms.

3. The patient interface of claim 2, wherein the rear strap is configured to be arranged to extend in a posterior and inferior direction on the patient's head in order to contact, in use, an occiput of the patient's head, the rear strap constructed from a first material and a second material, the first material arranged to contact, in use, a temporal region of the patient's head, and the second material arranged to contact, in use, the occiput of the patient's head.

4. The patient interface of claim 3, wherein the first material is textile and wherein the second material is silicone.

5. The patient interface of claim 2, wherein the second end of each removable arm of the pair of removable arms comprises a slot, and wherein the rear strap is received within each slot.

6. The patient interface of claim 5, wherein a width of the rear strap is less than a width of the slot, the rear strap configured to move within the slot and adjust a force vector.

7. The patient interface of claim 5, wherein each slot is curved and has a width greater than a width of the rear strap.

8. The patient interface of claim 5, wherein each slot is curved to have a negative curvature with respect to the first end of the removable arm.

9. The patient interface of claim 2, wherein each removable arm is configured to position the rear strap to extend in a posterior and inferior direction in use.

10. The patient interface of claim 1, wherein the second end of each removable arm of the pair of removable arms comprises a slot.

11. The patient interface of claim 10, wherein the slots are arcuate.

12. The patient interface of claim 1, wherein the opening length of each tab of the pair of tabs is between approximately 30 mm and approximately 50 mm.

13. The patient interface of claim 1, wherein each removable arm curves between the first end and the second end.

14. The patient interface of claim 1, wherein the second end is configured to contact the patient's head approximately 30° below the Frankfort horizontal.

15. The patient interface of claim 1, wherein each clip is biased toward a closed position, and wherein the clip is movable to an opening position in order to connect to the respective tab.

* * * * *